US007744898B2

(12) United States Patent
Chisari

(10) Patent No.: US 7,744,898 B2
(45) Date of Patent: Jun. 29, 2010

(54) PEPTIDES FOR INDUCING CYTOTOXIC T LYMPHOCYTE RESPONSES TO HEPATITIS B VIRUS

(75) Inventor: Francis V. Chisari, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 21 days.

(21) Appl. No.: 11/221,470

(22) Filed: Sep. 8, 2005

(65) Prior Publication Data
US 2006/0051746 A1 Mar. 9, 2006

Related U.S. Application Data

(60) Continuation of application No. 10/359,431, filed on Feb. 5, 2003, now abandoned, which is a division of application No. 08/591,502, filed as application No. PCT/US94/08685 on Aug. 1, 1994, now Pat. No. 6,607,727, which is a continuation-in-part of application No. 08/100,870, filed on Aug. 2, 1993, now abandoned, which is a continuation-in-part of application No. 07/935,898, filed on Aug. 26, 1992, now abandoned, which is a continuation-in-part of application No. 07/749,540, filed on Aug. 26, 1991, now abandoned.

(51) Int. Cl.
A61K 39/29 (2006.01)
C07K 14/02 (2006.01)
C07K 7/06 (2006.01)
C07K 4/02 (2006.01)

(52) U.S. Cl. .............................. 424/189.1; 424/196.11; 424/227.1; 530/328; 530/300

(58) Field of Classification Search ................ 424/450, 424/189.1, 277.1; 514/12; 530/350; 435/5
See application file for complete search history.

(56) References Cited

U.S. PATENT DOCUMENTS

| 3,645,852 A | 2/1972 | Axen et al. |
| 4,235,877 A | 11/1980 | Fullerton |
| 4,428,941 A | 1/1984 | Galibert et al. |
| 4,487,715 A | 12/1984 | Nitecki et al. |
| 4,559,230 A | 12/1985 | David et al. |
| 4,599,231 A | 7/1986 | Milich et al. |
| 4,659,569 A | 4/1987 | Mitsuhashi et al. |
| 4,818,527 A | 4/1989 | Thornton et al. |
| 4,882,145 A | 11/1989 | Thornton et al. |
| 4,935,235 A | 6/1990 | Rutter et al. |
| 5,017,558 A | 5/1991 | Vyas |
| 5,019,386 A | 5/1991 | Machida et al. |
| 5,039,522 A | 8/1991 | Neurath |
| 5,100,662 A | 3/1992 | Bolcsak et al. |
| 5,133,961 A | 7/1992 | Ellis et al. |
| 5,143,726 A | 9/1992 | Thornton et al. |
| 5,158,769 A | 10/1992 | Neurath et al. |
| 5,780,036 A | 7/1998 | Chisari |
| 5,788,969 A | 8/1998 | Chisari |
| 5,840,303 A | 11/1998 | Chisari |
| 5,932,224 A | 8/1999 | Chisari |
| 6,037,135 A | 3/2000 | Kubo et al. |
| 6,235,288 B1 | 5/2001 | Chisari |
| 6,322,789 B1 | 11/2001 | Vitiello et al. |
| 6,419,931 B1 * | 7/2002 | Vitiello et al. ........... 424/201.1 |
| 6,607,727 B1 | 8/2003 | Chisari et al. |
| 2003/0021809 A1 | 1/2003 | Chisari |
| 2003/0171538 A1 | 9/2003 | Chisari |

FOREIGN PATENT DOCUMENTS

| EP | 105 481 A1 | 4/1984 |
| EP | 013 828 B1 | 3/1987 |
| EP | 271 302 | 12/1987 |
| EP | 293 201 | 11/1988 |
| EP | 326 111 | 1/1989 |
| EP | 327 369 A2 | 8/1989 |
| EP | 469 281 | 6/1993 |
| EP | 431 327 B1 | 4/1996 |
| EP | 534 615 B1 | 1/2001 |
| GB | 2 034 323 | 6/1980 |
| JP | 60-161999 | 8/1985 |
| JP | 64-025800 | 1/1989 |
| WO | WO 93/03753 | 3/1993 |
| WO | WO 94/19011 A1 | 3/1993 |
| WO | WO 94/03205 | 2/1994 |
| WO | WO 94/20127 A1 | 9/1994 |
| WO | WO 94/25060 A1 | 11/1994 |
| WO | WO 95/03777 A1 | 2/1995 |
| WO | WO 95/04817 A1 | 2/1995 |

OTHER PUBLICATIONS

Moriarty et al (Science 227:429-433, 1984).*
Heathcote et al (Hepatology 30:531-536, 1999).*
DiBrino et al (Journal of Immunology 151 (11): 5930-5935, 1993).*
Depla et al (Journal of Virology 82:435-450, 2008).*
Aggarwal et al. "Oral salmonella: Malaria circumsporozoite recombinants induce specific CD8+ cytotoxic T cells" *J. Exp. Med,* 1990, 172:1083-1090.
Aichele et al "Antiviral cytotoxic T cell response induced by in vivo priming with a free synthetic peptide" *J. Exp. Med,* 1990, 171:1815-1820.
Bertoletti, A. et al. "Natural variants of cytotoxic epitopes are T-cell receptor antagonists for antiviral cytotoxic T cells" *Nature,* Jun. 2, 1994, 369:407-410.

(Continued)

Primary Examiner—Mary E Mosher
(74) Attorney, Agent, or Firm—Saliwanchik, Lloyd & Saliwanchik

(57) ABSTRACT

Peptides are used to define epitopes that stimulate HLA-restricted cytotoxic T lymphocyte activity against hepatitis B virus antigens. The peptides are derived from regions of HBV polymerase, and are particularly useful in treating or preventing HBV infection, including methods for stimulating the immune response of chronically infected individuals to respond to HBV antigens.

22 Claims, 23 Drawing Sheets

OTHER PUBLICATIONS

Bertoletti "HLA class I-restricted human cytotoxic T cells recognize endogenously synthesized hepatitis B nucleocapsid antigen" *Proc. Natl. Acad. Sci.* USA, 1991, 88:10445-10449.
Bessler, W.G. et al. "The synthetic analog of bacterial lipoprotein are potent immunoadjuvants in combination with or covalently linked to antigen" *Prog. Leukocyte Biol.*, 1986, 5:337-344.
Bevan "Stimulating killer cells" *Nature*, 1989, 342:478-479.
Bhatnagar et al. "Immune response to synthetic peptide analogues of hepatitis B surface antigen specific for the determinant" *Proc. Natl. Acad. Sci.* USA, 1982, 79:4400-4404.
Bichko, V. et al. "Subtype ayw variant of hepatitis B virus" *FEBS Letters*, Jun. 1985, 185(1):208-212.
Bowie, J.U. et al. "Deciphering the Message in Protein Sequences: Tolerance to Amino Acid Substitutions" *Science*, Mar. 1990, 247:1306-1310.
Braciale et al. "Class I major histocompatibility complex-restricted cytolytic T lymphocytes recognize a limited number of sites on the influenza hemagglutinin" *Proc. Natl. Acad. Sci.* USA, 1989, 86:277-281.
Buller et al. "Induction of cytotoxic T-cell responses in vivo in absence of CD4 helper cells" *Nature*, 1987, 328:76-79.
Carbone et al. "Induction of cytotoxic T lymphocytes by primary in vitro stimulation with peptides" *J. Exp. Med*, 1988, 167:1767-1779.
Carbone, F.R. and Bevan, M.J. "Induction of Ovalbumin-Specific Cytotoxic T Cells by in Vivo Peptide Immunization" *J. Exp. Med.*, Mar. 1989, 169:603-612.
Cassell et al. "Linked recognition of helper and cytotoxic antigenic determinants for the generation of cytotoxic T lymphocytes" *Ann. N.Y. Acad. Sci*, 1991, pp. 51-60.
Celis et al. "Recognition of hepatitis B surface antigen by human T lymphocytes" *J. Immunol*, 1988, 140:1808-1815.
Chisari et al. "Hepatitis B virus structure and biology" *Microbial Pathogenesis*, 1989, 6:311-325.
Collins, D.S. et al. "Processing of Exogenous Liposome-Encapsulated Antigens In Vivo Generates Class I MHC-Restricted T Cell Responses" *J. Immunology*, 1992, 148:3336-3341.
De Magistris, M.T. et al. "Antigen analog-major histocompatibility complexes act as antagonists of the T cell receptor" *Cell*, Feb. 21, 1992, 68(4):625-634.
Deres et al. "In vivo priming of virus-specific cytotoxic T lymphocytes with synthetic lipopeptide vaccine" *Nature*, 1989, 342:561-564.
Falk et al. "Allele-specific motifs revealed by sequencing of self-peptides eluted from MHC molecules" *Nature*, 1991, 351:290-296.
Ferrari et al. "Identification of immunodominant T cell epitopes of the hepatitis B virus nucleocapsid antigen" *J. Clin. Invest*, 1991, 88:214-222.
Fujii et al. "Peptide chemistry 1983" published 1984 by Protein Research Foundation (OSAKA), pp. 215-220.
Galibert et al. "Nucleotide sequence of the hepatitis B virus genome (subtype ayw) cloned in *E. Coli*" *Nature*, 1979, 281:646-650.
Golvano et al. "Polarity of immunogens: Implications for vaccine design" *Eur. J. Immunol*, 1990, 20:2363-2366.
Gotch et al. "Recognition of influenza A matrix protein by HLA-A2-restricted cytotoxic T lymphocytes" *J. Exp. Med*, 1988, 163:2045-2057.
Gotch et al. "Cytotoxic T lymphocytes recognize a fragment of influenza virus matrix protein in associate with HLA-A2" *Nature*, 1987, 326:881-882.
Greenstein, J.L. et al. "A Universal T Cell Epitope-Containing Peptide From Hepatitis B Surface Antigen can Enhance Antibody Specific for HIV gp120" *J. Immunology*, 1992, 148:3970-3977.
Guilhot et al. "Hepatitis B virus (HBV)-specific cytotoxic T-cell response in humans: Production of target cells by stable expression of HBV-encoded proteins in immortalized human B-cell lines" *J. Virol*, 1992, 66:2670-2678.
Hayashi et al. "Studies on peptides CLXVI. Solid-phase synthesis and immunological properties of fragment peptides related to human hepatitis B virus surface antigen (HBsAg) and its pres-S2 gene" *Chem. Pharm. Bull.*, 1988, 32:4993-4994.

Hilleman, M.R. "Comparative Biology and Pathogenesis of AIDS and Hepatitis B Viruses: Related but Different" *AIDS Res. and Human Retroviruses*, 1994, 10(11):1409-1419.
Hopp, T.P. "Immunogenicity of a synthetic HBsAg peptide: enhancement by conjugate to a fatty acid carrier" *Mol. Immunol.*, 1984, 21:13-16.
Ishioka et al. "Induction of class I MHC-restricted, peptide-specific cytolytic T lymphocytes by peptide priming in vivo" *J. Immunol*, 1989, 143:1094-1100.
Ishioka et al. "Class I MHC-restricted, peptide-specific cytotoxic T lymphocytes generated by peptide priming in vivo" *Vaccines 90*, Cold Spring Harbor Press pp. 7-11, 1990.
Jameson, S.C. et al. "Clone-specific T cell receptor antagonists of major histocompatibility complex class I-restricted cytotoxic T cells" *J. Exp. Med.*, Jun. 1, 1993, 177(6):1541-1550.
Kast et al. "Protection against lethal Sendai virus infection by in vivo priming of virus-specific cytotoxic T lymphocytes with a free synthetic peptide" *Proc. Natl. Acad. Sci.* USA, 1991, 88:2283-2287.
Klavinskis et al. "Molecularly engineered vaccine which expresses an immunodominant T-cell epitope induces cytotoxic T lymphocytes that confer protection for lethal virus infection" *J. Viral*, 1989, 63:4311-4316.
Kumar, V. et al. "Amino acid variations at a single residue in an autoimmune peptide profoundly affect its properties: T-cell activation, major histocompatibility complex binding, and ability to block experimental allergic encephalomyelitis" *Proc. Natl. Acad. Sci.* USA, Feb. 1990, 87:1337-1341.
Lee, K.K. et al. "Cross-Reactive and Strain-Specific Antipeptide Antibodies to *Pseudomonas aeruginosa* PAK and PAO Pili" *Infection and Immunity*, Sep. 1990, 58(9):2727-2732.
Lerner et al. "Chemically synthesized peptides predicted form the nucleotide sequence of the hepatitis B virus genome elicit antibodies reactive with the native envelope protein of Dane particles" *Proc. Natl. Acad. Sci*, USA, 1981, 78:3403-3407.
Lewin, R. "When Does Homology Mean Something Else?" *Science*, 1987, 237:1570.
Mack et al. "Hepatitis B virus particles contain a polypeptide encoded by the largest open reading frame: A putative reverse transcriptase" *J. Virology*, 1988, 62:4786-4790.
Melief et al. "Cooperation between subclasses of T lymphocytes in the in vitro generation of cytotoxicity against a mutant H-2K difference an analysis with anti-lyt antisera" *Eur. J. Immunol*, 1979, 9:7-12.
Milich et al. "Immunogenetics and cellular correlates of the immune response to hepatitis B surface antigen determinants" *Adv. Hepatitis Res*, Masson, NY, NY USA, 1984, 91-109.
Milich et al. "Comparative immunogenicity of hepatitis B virus core and E antigens" *J. Immunol*, 1988, 141:3617-3624.
Milich et al. "Immune response to hepatitis B virus core antigen (HBcAg): LOcalization of T cell recognition sites within HBcAg/HBeAg" *J. Immunol.*, 1987, 139:1223-1231.
Milich et al. "Antibody production to the nucleocapsid and envelope of the hepatitis B virus primed by a single synthetic T cell site" *Nature*, 1987, 329:547-549.
Milich et al. "Hepatitis B synthetic immunogen comprised of nucleocapsid T-cell sites and an envelope B-cell epitope" *Proc. Natl. Acad. Sci.* USA, 1988, 85:1610-1614.
Milich "T- and B-cell recognition of hepatitis B viral antigens" *Immunol. Today*, 1988, 9:380-386.
Mondelli et al. "Definition of hepatitis B virus (HBV)-specific target antigens recognized by cytotoxic T cells in acute HBV infection" *Clin. Exp. Immunol*, 1987, 68:242-250.
Mondelli et al. "Specificity of T lymphocyte cytotoxicity to autologous hepatocytes in chronic hepatitis B virus infection: Evidence that T cells are directed against HBV core antigen expressed on hepatocytes" *J. Immunol*, 1982, 129:2773-2778.
Moore et al. "Introduction of soluble protein into the class I pathway of antigen processing and presentation" *Cell*, 1988, 54:777-785.
Moriyama et al. "Immunobiology and pathogenesis of hepatocellular injury in hepatitis B virus transgenic mice" *Science*, 1990, 248:361-364.

Nayersina, R. et al. "HLA A2 Restricted Cytotoxic T Lymphocyte Responses to Multiple Hepatitis B Surface Antigen Epitopes during Hepatitis B Virus Infection" *J. Immunology*, May 1993, 150(10):4659-4671.

Neurath at el. "Specificity of antibodies elicited by a synthetic peptide having a sequence in common with a fragment of a virus protein—The hepatitis B surface antigen" *Dev. Biol. Stand*, 1983, 54:103-112.

Parker, K.C. et al. "Peptide Binding to HLA-A2 and HLA-B27 Isolated from *Escherichia coil*." *J. Biol. Chem.*, Mar. 1992, 267(8):5451-5459.

Pasek, M. et al. "Hepatitis B virus genes and their expression in *E. coli*" *Nature*, Dec. 1979, 282:575-579.

Penna et al. "Cytotoxic T lymphocytes recognize an HLA-A2-restricted epitope within the hepatitis B virus nucleocapsid antigen" *J. Exp. Med.*, 1991, 174:1565-1570.

Penna et al. "Hepatitis B virus (HBV-specific cytotoxic T cell (CTL) response in humans: Characterization of HLA class II-restricted CTLs that recognize endogenously synthesized HBV envelope antigens" *J. Virol*, 1992, 66:1193-1198.

Reddy, R. et al. "In Vivo Cytotoxic T Lymphocyte Induction with Soluble Proteins Administered in Liposomes" *J. Immunology*, Mar. 1992, 148(5):1585-1589.

Reeck, G.R. et al. "'Homology' in Proteins and Nucleic Acids: A Terminology Muddle and a Way out of It" *Cell*, Aug. 1987, 50:667.

Rehermann et al. "The cytotoxic T lymphocyte response to multiple hepatitis B virus polymerase epitopes during and after acute viral hepatitis" *J. Exp. Med.*, Mar. 1, 1995, 181(3):1047-1058.

Roitt, I. et al. Immunology (third ed.), Mosby, St. Louis, p. 4.14, 1993.

Rotzschke et al. "Isolation and analysis of naturally processed viral peptides as recognized by cytotoxic T cells" *Nature*, 1990, 348:252-254.

Ruppert, J. et al. "Prominent role of secondary anchor residues in peptide binding to HLA-A2.1 molecules" *Cell*, 1993, 74(5):929-937.

Sarobe et al. "Induction of antibodies against peptide hapten does not require covalent linkage between hapten & class II presentable T helper peptide" *Eur. J. Immunol*, 21:1555-1558.

Schumacher et al. "Peptide selection by MHC class I molecules" *Nature*, 1991, 350:703-706.

Sprent et al. "Properties of purified T cell subsets" *J. Exp. Med*, 1985, 162:2068-2088.

Tam et al. "Vaccine engineering: enhancement of immunogenicity of synthetic peptide vaccines related to hepatitis in chemically defined models consisting of T- and B-cell epitopes" *Proc. Natl. Acad. Sci. USA*, 1989, 86:9084-9088.

Tong, S. et al. "Active Hepatitis B Virus Replication in the Presence of Anti-HBe is Associated with Viral Variants Containing an Inactive Pre-C Region" *Virology*, 1990, 176:596-603.

Townsend et al. "The epitopes of influenza nucleoprotein recognized by cytotoxic T lymphocytes can be defined with short synthetic peptides" *Cell*, 1986, 44:959-968.

Van Bleek et al. "Isolation of an endogenously processed immunodominant viral peptide from the class IH-2$K^b$ molecule" *Nature*, 1990, 348:213-216.

Vitiello, A. et al. "Development of a Lipopeptide-based Therapeutic Vaccine to Treat Chronic HBV Infection" *J. Clin. Invest.*, Jan. 1995, 95:341-349.

Von Boehmer et al. "Autonomously proliferating K/D-restricted cytolytic T cell clones" *Eur. J. Immunol*, 1983, 13:176-179.

Von Boehmer et al. "Distinct Ir genes for helper and killer cells in the cytotoxic response to H-Y antigen" *J. Exp. Med*, 1979, 150:1134-1142.

Von Boehmer et al. "Lyt-2 T cell-Independent functions of Lyt-2+ cells stimulated with antigen or concanavalin A" *J. Immunol*, 1984, 133:59-64.

Wakita et al. "Gamma-interferon production response to hepatitis B core protein & synthetic peptides in patients with chronic hepatitis B virus infection" *Digestion*, 1990, 47:149-155.

Watari, E. et al. "A synthetic peptide induces long-term protection from lethal infection with herpes simplex virus 2" *J. Exp. Med.*, 1987, 165:459-470.

Widmer et al. "Antigen-driven helper cell-independent cloned cytolytic T lymphocytes" *Nature*, 1981, 294:750-752.

Yssel, H. et al. "T Cell Activation-Inducing Epitopes of the House Dust Mite Allergen *Der p I*" *J. Immunology*, Feb. 1992, 148(3):738-745.

Zinkernagel et al. "The lymphoreticular system in triggering virus plus self-specific cytotoxic T cells: Evidence for T help" *J. Exp. Med*, 1978, 147:897-911.

Bertoletti, A. et al. "Definition of a minimal optimal cytotoxic T-cell epitope within the hepatitis B virus nucleocapsid protein," *Virology*, 1993, 67(4):2376-2380.

* cited by examiner

FIG. 3A
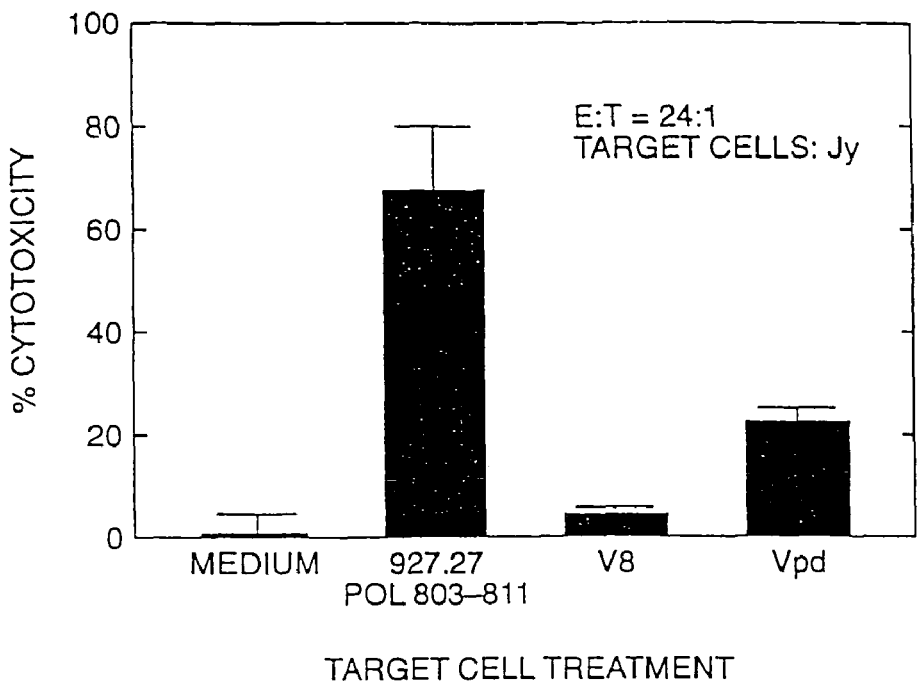
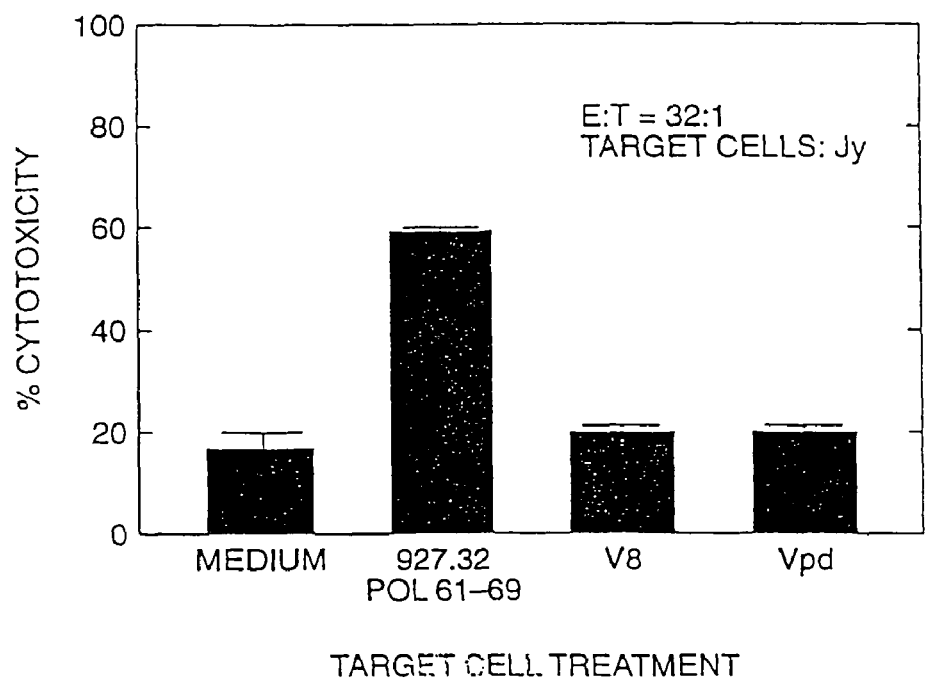
FIG. 3B

FIG. 4A

| | | | |
|---|---|---|---|
| 39 | MPLSYQHFRKLLLLDD--EA | GPLEEELPRLADEGLNRRVA | EDLNLGNLNVSIPWTHKVGN |
| 40 | MPLSYQHFRKLLLLD???EA | GPLEEELPRLADEGLNRRVA | EDLNLGNLNVSIPWTHKVGN |
| 41 | MPLSYQHFRKLLLLDD--EA | GPLEEELPRLADEGLNRRVA | EDLNLGNLNVSIPWTHKVGN |
| 42 | MPLSYQHFRKLLLLDD--EA | GPLEEELPRLADEGLNRRVA | EDLNLGNLNVSIPWTHKVGN |
| 43 | MPLSYQHFRKLLLLDD--EA | GPLEEELPRLADEGLNRRVA | EDLNLGNLNVSIPWTHKVGN |
| 44 | MPLSYQHFRKLLLLDD--EA | GPLEEELPRLADEGLNRRVA | EDLNLGNLNVSIPWTHKVGN |
| 45 | MPLSYQHFRKLLLLDD--EA | GPLEEELPRLADEDLNRRVA | EDLNLGNLNVSIPWTHKVGN |
| 46 | MPLSYQHFRKLLLLDDGTEA | GPLEEELPRLADADLNRRVA | EDLNLGNPNVSIPWTHKVGN |
| 47 | MPLSYQHFRKLLLLDE--EA | GPLEEELPRLADEGLNRRVA | EDLNLGNLNVSIPWTHKVGN |
| 48 | MPLSYQHFRKLLLLDD--EA | GPLEEELPRLADEGLNRRVA | EDLNLGNLNVSIPWTHKVGN |
| 49 | MPLSYQHFRKLLLLDD--EA | GPLEEELPHLADEGLNRRVA | EDLNLGNLNVSIPWTHKVGN |
| 50 | MPLSYQHFRKLLLLDD--EA | GPLEEELPRLADEGLNRPVA | EDLNLGNLNVSIPWTHKVGN |
| 51 | MPLSYQHFRKLLLLDDGTEA | GPLEEELPRLADADLNRRVA | EDLNLGNLNVSIPWTHKVGN |
| 52 | MPLSYQHFRKLLLLDDGTEA | GPLEEELPRLADADLHRRVA | EDLNLGNLNVSIPWTHKVGN |
| 53 | MPLSYQHFRKLLLLDD--EA | GPLEEELPRLADEGLNRRVA | EDLNLGNLNVSIPWTHKVGN |
| 54 | MPLSYQHFRRLLLLDD--EA | GPLEEELPRLADEGLNRRVA | EDLNLGNLNVSIPWTHKVGN |
| 55 | MPLSYQHFRRLLLLDD--EA | GPLEEELPRLADEGLNRRVA | EDLNLGNLNVSIPWTHKVGN |
| 56 | MPLSYQHFRRLLLLDD--EA | GPLEEELPRLADEGLNRRVA | EDLNLGNLNVSIPWTHKVGN |
| 57 | MPLSYQHFRRLLLLDD--EA | GPLEEELPRLPDQGLNRRVA | EDLNLGNLNVSIPWTHKVGN |
| 58 | MPLSYQHFRRLLLLHD--EA | GPLEEELPrLaDegLnrrVA | EDLNLGNlNVSIPWTHKVGN |
| 158 | MPLSYQHFRkLllLddGTEA | GPLEEELPrLaDeglnrrVA | EDlNlGNlNVSIPWTHKVGN |

FIG. 4B

```
    61
39  FTGLYSSTVPVFNPEWQTPS  FPHIHLQEDIINRCQQYVGP  LTVNEKRRLKLIMPARFYPN
40  FTGLYSSTVPVFNPEWQTPS  FPHIHLQEDIINRCQQYVGP  LTVNEKRRLKLIMPARFYPN
41  FTGLYSSTVPIFNPESQTPS  FPNIHLQEDIINRCQQYVGP  LTVNEKRRLKLIMPARFYPN
42  FTGLYSSTVPVLNPESQTPS  FPNIHLQEDIINRCQQYVGP  LTVNEKRRLKLIMPARFYPN
43  FTGLYSSTVPVFNPEWQTPS  FPHIHLQEDIINRCQQYVGP  LTVNEKRRLKLIMPARFYPN
44  FTGLYSSTVPVFNPEWQTPS  FPHIHLQEDIINRCQQYVGP  LTVNEKRRLKLIMPARFYPN
45  FTGLYSSTVPVFNPEWQTPS  FPHIHLQEDIINRCQQYVGP  LTVNEKRRLKLIMPARFYPK
46  FTGLYSSTVPIFNPEWQTPS  FPKIHLQEDIINRCQQYVGP  LTVNEKRRLKLIMPARFYPT
47  FTGLYSSTVPVFNPEWQTPS  FPDIHLQEDIVDRCKQFVGP  LTVNENRRLKLIMPARFYPN
48  FTGLYSSTVPVFNPEWQTPS  FPDIHLQEDIVDRCKQFVGP  LTVNENRRLKLIMPARFYPN
49  FTGLYSSTVPCFNPKWQTPS  FPDIHLQEDIINKCKQFVGP  LTVNEKRRLKLIMPARFYPN
50  FTGLYSSTVPSFNPQWQTPS  FPDIHLQEDIINRCEQFVGP  LTVNENRRLKLIMPARFYPN
51  FTGLYSSTVPSFNPKWQTPS  FPKIHLQEDIINRCQQFVGP  LTVNEKRRLKLIMPARFYPT
52  FTGLYSSTAPIFNPEWQTPS  FPKIHLQEDIINRCQQFVGP  LTVNEKRRLKLIMPARFYPT
53  FTGLYSSTVPIFNPEWQTPS  FPHIHLQEDIINRCQQYVGP  LTVNEKRRLKLIMPARFYPN
54  FTGLYSSTVPVFNPDWKTPS  FPNIHLHQDIIKKCEQFVGP  LTVNEKRRLQLIMPARFYPK
55  FTGLYSSTVPVFNPHWKTPS  FPNIHLHQDIIKKCEQFVGP  LTVNEKRRLQLIMPARFYPN
56  FTGLYSSTVPVFNPHWKTPS  FPNIHLHQDIIKKCEQFVGP  LTVNEKRRLQLIMPARFYPK
57  FTGFYSSTVPVFNPHWETPS  FPNIHLHQDIIKKCEQFVGP  LTVNEKRRLQLIMPARFYPN
58  FTGFYSSTVPVFNPHWKTPS  FPNIHLHQDIIKKCEQFVGP  LTVNEKRRLKLIMPARFYPN
158 FTGlYSSTvPvfNPewqTPS  FP.IHLqeDIinrCqQfVGP  LTVNekRRLkLIMPARFYPn
```

FIG. 4C

```
    121
39  LTKYLPLDKGIKPYYPEHAV  NHYFKTRHYLHTLWKAGILY  KRETTRSASFCGSPYSWEQE
40  LTKYLPLDKGIKPYYPEHAV  NHYFKTRHYLHTLWKAGILY  KRETTRSASFCGSPYSWEQE
41  LTKYLPLDKGIKPYYPEHAV  NHYFKTRHYLHTLWKAGILY  KRETTRSASFCGSPYSWEQE
42  LTKYLPLDKGIKPYYPEHAV  NHYFKTRHYLHTLWKAGILY  KRETTRSASFCGSPYSWEQE
43  LTKYLPLDKGIKPYYPEHAV  NHYFKTRHYLHTLWKAGILY  KRETTRSASFCGSPYSWEQE
44  LTKYLPLDKGIKPYYPEHAV  NHYFKTRHYLHTLWKAGILY  KRETTRSASFCGSPYSWEQE
45  LTKYLPLDKGIKPYYPEHAV  NHYFKTRHYLHTLWKAGILY  KRETTRSASFCGSPYSWEQE
46  HTKYLPLDKGIKPYYPDQVV  NHYFQTRHYLHTLWKAGILY  KRETTRSASFCGSPYSWEQE
47  VTKYLPLDKGIKPYYPEHVV  NHYFQTRHYLHTLWKAGILY  KRESTHSASFCGSPYSWEQD
48  VTKYLPLDKGIKPYYPEYVV  NHYFQTRHYLHTLWKAGILY  KRETTRSASFCGSPYSWEQD
49  VTKYLPLDKGIKPYYPEHVV  NHYFQTRHYLHTLWKAGILY  KRETTRSASFCGSPYSWEQD
50  VTKYLPLDKGIKPYYPEHVV  NHYFQTRHYLHTLWKAGILY  KRETTRSASFCGSPYSWEQD
51  HTKYLPLDKGIKPYYPDQVV  NHYFQTRHYLHTLWKAGILY  KRETTRSASFCGSPYSWEQE
52  HTKYLPLDKGIKPYYPDQVV  NHYFQTRHYLHTLWKAGILY  KRETTHSASFCGSPYSWEQD
53  LTKYLPLDKGIKPYYPEYAV  NHYFKTRHYLHTLWKAGILY  KRETTHSASFCGSPYSWEQE
54  VTKYLPLDKGIKPYYPEHLV  NHYFQTRHYLHTLWKAGILY  KRETTHSASFCGSPYSWEQD
55  VTKYLPLDKGIKPYYPEYLV  NHYFQTRHYLHTLWKAGILY  KRETTHSASFCGSPYSWEQE
56  VTKYLPLDKGIKPYYPEHLV  NHYFQTRHYLHTLWKAGILY  KRETTHSASFCGSPYSWEQD
57  VTKYLPLDKGIKPYYPEHLV  NHYFQTRHYLHTLWKAGILY  KRETTHSASFCGSPYSWEQD
58  VTKYLPLDKGIKPYYPEHLV  NHYFQTRHYLHTLWKAGILY  KRETTHSASFCGSPYSWEQE
158 .TKYLPLDKGIKPYYPeh.v  NHYFqTRHYLHTLWKAGILY  KREtTrSASFCGSPYSWEQe
```

FIG. 4D

```
    181
39  LQHGRLVFQTSTRHGDESFC SQSSGILSRSPVGPCVRSQL KQSRLGLQPQQGSMARGKSG
40  LQHGRLVFQTSTRHGDESFC SQSSGILSRSPVGPCVRSQL KQSRLGLQPQQGSLARGKSG
41  LRHGRLVFQTSTRHGDESFC SQSSGILSRSPVGPCVRSQL KQSRLGLQPQQGSLARGKSG
42  LQHGRLVFQTSTRHGDESFC SQSSGILSRSPVGPCVRSQL KQSRLGLQPQQGSLARGNQG
43  LQHGRLVFQTSTRHGDESFC SQSSGILSRSPVGPCVRSQL KQSRLGLQPQQGSLARGKSG
44  LQHGRLVFQTSTRHGDESFC SQSSGILSRSPVGPCVRSQL TQSRLGLQPQQGSLARGKSG
45  LQHGRLVFQTSTRHGDESFC SQSSGILSRSPVGPCVRSQL KQSRLGLQPQQGSLARGKSG
46  LQH------SQRHGDESFC  SQPSGIPSRSSVGPCIRSQL NKSRLGLQPHQGPLASSQPG
47  LQHGRLVFQTSKRHGDKSFC PQSPGILPRSSVGPCIQSQL RKSRLGPQPTQGQLAGRPQG
48  LQHGRLVFQTSKRHGDKSFC PQSSGILPRSSVGPCIQSQL RKSRLGPQPEQGQLAGRQQG
49  LQHGRLVLQTSTRHGDKSFR PQSSGILSRSPVGPCIQSQL RQSRLGPQPTQGQLAGLQQG
50  LQHGRLVLQTSTRHGDKSFR PQSSGILSRSPVGPCIQSQL RQSRLGPQPTQGQLAGLQQG
51  LQHGRLVIKTSQRHGDKSFR SQPSGILSRSPVGPCIQSQL KQSRLGLQPHQGPLASSQPG
52  LQHGRLVIKTSCRHGDESFC SQSSGILSRSSVGPCIRSQL KQSRLGLQPRQGRLASSQPS
53  LQHGRLVFQTSTRHGDESFC SQSSGILSRSPVGPCVRSQL KQSRLGLQPQQGSLARGKSG
54  LQHG----------AESFH  QQSSGILSRPPVGSSLQSKH RKSRLGLQSQQGHLARRQQG
55  LQHG----------AESFH  QQSSGILSRPPVGSSLQSKH RKSRLGLQSQQGHLARRQQG
56  LQHG----------AESFH  QQSSGILSRPPVGSSLQSKH RKSRLGLQSQQGHLARRQQG
57  LQHG----------AESIH  QQSSGILSRPPVGSSLQSKH RKSRLGLQSQQGHLARRQQG
58  LQHG----------AESFH  QQSSGILSRPPVGSSLQSKH RKSRLGLQSQQGHLARRQQG
158 LqHGRLVfqTStRHGdeSFc sQssGilsRspvGpc.rsql .qSRLGlQpQqG.lAr.qqg
```

FIG. 4E

```
      241
 39   RSGSIRARVHPTTRRSFGVE   PSGSGHIDNSASSTSSCLHQ   SAVRKTAYSHLSTSKRQSSS
 40   RSGSIRARVHPTTRRSFGVE   PSGSGHIDNSASSTSSCLHQ   SAVRKTAYSHLSTSKRQSSS
 41   RSGRLRARVHPTTRRSFGVE   PSGSGHIDNSASSASSCFHQ   SAVRKTAYSHLSTSKRQSSS
 42   RSGSIWARVHSTTRRSFGVE   PSGSGHIDNSASSASSCLYQ   SAVRKTAYSHLSTSKRQSSS
 43   RSGSIRARVHPTTRRSFGVE   PAGSGRIDNRASSTSSCLHQ   SAVRKTAYSHLSTSKRQSSS
 44   RSGSIRARVPPTTRRSFGVE   PSGSGHIDNRASSTSSCLHQ   SAVRKTAYSHLSTSKRQSSS
 45   RSGSIRARVPPTTRRSFGVE   PSGSGHIDNRASSTSSCLHQ   SAVRKTAYSHLSTSKRQSSS
 46   RSGSIRARAHPSTRRYFGVE   PSGSGHIDHSVNNSSSCLHQ   SAVRKAAYSHLSTSKRQSSS
 47   GSGSIRARIHPSPWGTVGVE   PSGSGHTHICASSSSSCLHQ   SAVRTAAYSPISTSKGHSSS
 48   GSGSIRARVHPSPWGTVGVE   PSGSGPTHNCASSSSSCLHQ   SAVRKAAYSLIPTSKGHSSS
 49   GSGSIRAGIHSTPWGTVGVE   PSSSGHTHNCANSSSSCLHQ   SAVRKEAYSPVSTSKRHSSS
 50   GSGSIRAGIHSTPWGTVGVE   PSSSGHTHNCANSSSSCLHQ   SAVRKEAYSPVSTSKRHSSS
 51   RSGSIRARVHPSTRRCFGVE   PSGSGHVDPSVNNSSSCLHQ   SAVRKAAYSHLSTSKRQSSS
 52   RSGSIRAKAHPSTRRYFGVE   PSGSGHIDHSVNNSSSCLHQ   SAVRKAAYSHLSTSKRQSSS
 53   RSGSIWSRVHPTTRRPFGVE   PSGSGHIDNTASSTSSCLHQ   SAVRKTAYSHLSTSKRQSSS
 54   RSWSIRAGFHPTARRPFGVE   PSGSGHTTNFASKSASCLHQ   SPVRKAAYPAVSTFEKHSSS
 55   RSWSIRAGIHPTTRRPFGVE   PSGSGHTRNVASKSASCLYQ   SPVRKAAYPAVSTFEKHSSS
 56   RSWSIRAGFHPTARRPFGVE   PSGSGHTTNFASKSASCLHQ   SPVRKAAYPSVSTFERHSSS
 57   WSWSIRAGTHPTARRPFGVE   PSGSGHTTHRASKSASCLYQ   SPDRKATYPSVSTFERHSSS
 58   RSWSIRAGFHPTARRSFGVE   PSGSGHTTYRASKSASCLYQ   SPVRKAAYPSVSTFEKHSSS
158   rSgsirarvhpttrr.fGVE   PsgSGhidn.asssssSClhq  SavRkaaYshlsTskrqSSS
```

FIG. 4F

```
    301
39  GHAVEFHNIPPSSARSQSEG  PIFSCWWLQFRNSKPCSDYC  LTHIVNLLEDWGPCTEHGEH
40  GHAVELHNIPPSSARPQSEG  PILSCWWLQFRNSKPCSDYC  LTHIVNLLEDWGPCTEHGEH
41  GHAVELHNIPPSSARSQSEG  PIFSCWWLQFRNSKPCSDYC  LTHIVNLLEDWGPCTEHGEH
42  GHAVELHNIPPSSCARSQSEG PISSCWWLQFRNSEPCSDYC  LTHIVNLLEDWGPCTEHGEH
43  GHAVELHNIPPSSARPQSEG  PILSCWWLQFRNSKPCSDYC  LTHIVNLLEDWGPCTEHGEH
44  GHAVELHHISPSPARSQSEG  PIFSSWWLQFRNSKPCSDYC  LTHIVNLLEDWGPCTEHGEH
45  GHAVELHHISPSPARSQSEG  PIFSSWWLQFRNSKPCCDYC  LTHIVNLLEDWGPCTEHGEH
46  GHAVEFHCLAPSSAGSQSQG  SVSSCWWLQFRNSKPCSEYC  LSHLVNLIEDWGPCDDHGEH
47  GHAVELHHFPPNSSRSQSQG  SVLSCWWLQFRNSKPCSEYC  LSHIVNLIEDWGPCAEHGEH
48  GHAVELHHFPPNSSRSRSQG  PVLSCWWLQFRNSKPCSEYC  LCHIVNLIEDWGPCTEHGEH
49  GNAVELHHVPPNSSRSQSQG  SVLSCWWLQFRNSKPCSEHC  LFHIVNLIDDWGPCAEHGEH
50  GHAVELHHVPPNSSRSQSQG  SVLSCWWLQFRNSKPCSEHC  LFHIVNLIEDWGPCAEHGEH
51  GHAVEFHCLPPSSARPQSQG  SVFSCWWLQFRNSKPCSEYC  LSHLVNLREDRGPCDEHGEH
52  GHAVEFHCLPPNSAGSQSQG  SVSSCWWLQFRNSKPCSEYC  LSHLVNLREDWGPCDEHGEH
53  GHAVELHNIPPSSARSQSEG  PIFSCWWLQFRNSKPCSDYC  LTHIVNLLEDWGPCTEHGEH
54  GHAVEFHNLPPNSARSQSER  PVFPCWWLQFRNSKPCSDYC  LSHLVNLLEDWGPCAEHGEH
55  GHAVELHNLPPNSARSQSER  PVFPCWWLQFRNSKPCSDYC  LSHLVNLLEDWGPCAEHGEH
56  GHAVELHNLPPNSARSQSER  PVFPCWWLQFRNSKPCSDYC  LSLIVNLLEDWGPCAEHGEH
57  GRAVELHNFPPNSARSQSER  PIFPCWWLQFRNSKPCSDYC  LSLIVNLLEDWGPCDEYGEH
58  GHAVELHNLPPNSARSQSER  PVFPCWWLQFRNSKPCSDYC  LSLIVNLREDWGPCTEHGEH
158 GhAVElHn.pPnsarsqSeg  pvfscWWLQFRNSkPCsdyC  L.hiVNLleDwGPCtehGEH
```

FIG. 4G

```
    361
39  NIRIPRTPARVTGGVFLVDK NPHNTTESRLVVDFSQFSRG STHVSWPKFAVPNLQSLTNL
40  NIRIPRTPARVTGGVFLVDK NPHNTTESTLVVDFSQFSRG STHVSWPKFAVPNLQSLTNL
41  NIRIPRTPARVTGGVFLVDK NPHNTTESRLVVDFSQFSRG STHVSWPKFAVPNLQSLTNL
42  NIRIPRTPARVTGGVFLVDK NPHNTTESRLVVDFSQFSRG STHVSWPKFAVPNLQSLTNL
43  NIRIPRTPARVTGGVFLVDK NPHNTTESRLVVDFSQFSRG STHVSWPKFAVPNLQSLTNL
44  NIRIPRTPARVTGGVFLVDK NPHNTTESRLVVDFSQFSRG STHVSWPKFAVPNLQSLTNL
45  NIRIPRTPARVTGGVFLVDK NPHNTAESRLVVDFSQFSRG STHVSWPKFAVPNLQSLTNL
46  HIRIPRTPARVTGGVFLVDK NPHNTTESRLVVDFSQFSRG ITRVSWPKFAVPNLQSLTNL
47  RIRTPRTPARVTGGVFLVDK NPHNTTESRLVVDFSQFSRG NTRVSWPKFAVPNLQSLTNL
48  RIRTPRTPARVTGGVFLVDK NPHNTTESRLVVDFSQFSRG NTRVSWPKFAVPNLQSLTNL
49  RIRTPRTPARVTGGVFLVDK NPHNTTESRLVVDFSQFSRG NTRVSWPKFAVPNLQSLTNL
50  RIRTPRTPARVTGGVFLVDK NPHNTTESRLVVDFSQFSRG NTRVSWPKFAVPNLQSLTNL
51  HIRIPRTPARVTGGVFLVDK NPHNTTESRLVVDFSQFSRG ITRVSWPKFAIPNLQSLTNL
52  HIRIPRTPARVTGGVFLVDK NPHNTAESRLVVDFSQFSRG ISRVSWPKFAVPNLQSLTNL
53  NIRIPRTPARVTGGVFLVDK NPHNTTESRLVVDFSQFSRG STHVSWPKFAVPNLQSLTNL
54  HIRIPRTPARVTGGVFLVDK NPHNTAESRLVVDFSQFSRG NYRVSWPKFAVPNLQSLTNL
55  HIRIPRTPARVTGGVFLVDK NPHNTAESRLVVDFSQFSRG NYRVSWPKFAVPNLQSLTNL
56  HIRIPRTPSRVTGGVFLVDK NPHNTAESRLVVDFSQFSRG NYRVSWPKFAVPNLQSLTNL
57  HIRIPRTPARVTGGVFLVDK NPHNTAESRLVVDFSQFSRG NYRVSWPKFAVPNLQSLTNL
58  HIRIPRTPARVTGGVFLVDK NPHNTAESRLVVDFSQFSRG NYRVSWPKFAVPNLQSLTNL
158 .IRiPRTPaRVTGGVFLVDK NPHNTtESrLVVDFSQFSRG .trVSWPKFAvPNLQSLTNL
```

FIG. 4H

```
     421
39   LSSNLSWLSLDVSAAFYHIP   LHPAAMPHLLVGSSGLPRYV   ARLSSTSRNINHQHGAMQDL
40   LSSNLSWLSLDVSAAFYHIP   LHPAAMPHLLVGSSGLPRYV   VCLSSTSKNINIYQHGTMQDL
41   LSSNLSWLSLDVSAAFYHIP   LHPAAMPHLLVGSSGLPRYV   ARLSSTSRNINYQHGTMQDL
42   LSSNLSWLSLDVSAAFYHIP   LHPAAMPHLLVGSSGLPRYV   ARLSSTSRNINYQHGTMQDL
43   LSSNLSWLSLDVSAAFYHIP   LHPAAMPHLLVGSSGLPRYV   ARLSSTSRNINYQHGTMQDL
44   LSSNLSWLSLDVSAAFYHIP   LHPAAMPHLLVGSSGLPRYV   ARLSSTSRNINHQHGTMQDL
45   LSSNLSWLSLDVSAAFYHIP   LHPAAMPHLLVGSSGLPRYV   ARLSSTSRNINHQHGTMQDL
46   LSSNLSWLSLDVSAAFYHIP   LHPAAMPHLLIGSSGLPRYV   ARLSSNSRINNNQYGTMQDL
47   LSSNLSWLSLDVSAAFYHLP   LHPAAMPHLLVGSSGLSRYV   ARLSSNSRIINHQHGTMQDL
48   LSSNLSWLSLDVSAAFYHLP   LHPAAMPHLLVGSSGLSRYV   ARLSSNSRIINNQYGTMQNL
49   LSSDLSWLSLDVSAAFYHIP   LHPAAMPHLLVGSSGLSRYV   ARLSSNSRIINHQHRTMQNL
50   LSSDLSWLSLDVSAAFYHIP   LHPAAMPHLLVGSSGLSRYV   ARLSSNSRIINHQHRTMQNL
51   LSSNLSWLSLDVSAAFYHLP   LHPAAMPHLLIGSSGLSRYV   ARLSSNSRINNNQYGTMQNL
52   LSSNLSWLSLDVSAAFYHLP   LHPAAMPHLLVGSSGLSRYV   ARLSSNSRINNNQYGTMQNL
53   LSSNLSWLSLDVSAAFYHIP   LHPAAMPHLLVGSSGLPRYV   ARLSSTSRNINYQHGTMQNL
54   LSSNLSWLSLDVSAAFYHLP   LHPAAMPHLLVGSSGLPRYV   ARLSSNSRILNNQHGTMPDL
55   LSSNLSWLSLDVSAAFYHLP   LHPAAMPHLLVGSSGLSRYV   ARLSSNSRIFNYQHGTMQNL
56   LSSNLSWLSLDVSAAFYHLP   LHPAAMPHLLVGSSGLSRYV   ARLSSNSRILNHQHGTMPNL
57   LSSNLSWLSLDVSAGFYHLP   LHPAAMPHLLVGSSGVSRYV   ARLSSNSRNNNNQYGTMQNL
58   LSSNLSWLSLDVSAAFYHLP   LHPAAMPHLLVGSSGLSRYV   ARLSSNSRIFNNQHGTMQNL
158  LSSnLSWLSLDVSAaFYHiP   LHPAAMPHLLvGSSGlsRYV   arLSSnSriiN.QhgtMqnL
```

FIG. 4I

```
     481
39   HDSCSRNLYVSLLLLYKTFG  RKLHLYSHPIILGFRKIPMG  VGLSPFLLAQFTSAICSVVR
40   HDSCSRNLYVSLFLLYKTFG  RKLHLYSHPIILGFRKIPMG  VGLSPFLLAQFTSAICSVVR
41   HDSCSRNLYVSLLLLYKTFG  RKLHLYSHPIILGFRKIPMG  VGLSPFLLAQFTSAICSVVR
42   HDCSRNLYVSLLLLYKTFG   RKLHLYSHPIILGFRKIPMG  VGLSPFLLAQFTSAICSVVR
43   HDSCSRNLYVSLLLLYKTFG  RKLHLYSHPIILGFRKIPMG  GGLSPFLLAQFTSAICSVVR
44   HDSCSRNLYVSLLLLYKTFG  RKLHLYSHPIILGFRKIPMG  GGLSPFLLAQFTSAICSVVR
45   HDSCSRNLYVSLLLLYKTFG  RKLHLYSHPIILGFRKIPMG  GGLSPFLLAQFTSAICSVVR
46   HDSCSRQL
47   HNSCSRNLYVSIMLLYKTYG  WKLHLYSHPIILGFRKIPMG  VGLSPFLLAQFTSAICSVVR
48   HNSCSRNLYVSIMLLYKTYG  WKLHLYSHPIILGFRKIPMG  VGLSPFLLAQFTSAICSVVR
49   HDSCSRNLYVSIMLLYKTYG  RKLHLYSHPIILGFRKIPMG  VGLSPFLLAQFTSAICSVVR
50   HDSCSRNLYVSIMLLYKTYG  RKLHLYSHPIILGFRKIPMG  VGLSPFLLAQFTSAICSVVR
51   HDSCSRQLYVSIMLLYKTYG  WKLHLYSHPIVLGFRKIPMG  VGLSPFLLAQFTSAICSVVR
52   HDSCSRNLYVSIMLLYKTYG  WKLHLYSHPIVLGFRKIPMG  VGLSPFLLAQFTSAICSVVR
53   HDSCSRNLYVSLLLLYKTFG  RKLHLYSHPIILGFRKIPMG  VGLSPFLLAQFTSAICSVVR
54   HDYCSRNLYVSLLLLYQTFG  RKLHLYSHPIILGFRKIPMG  VGLSPFLLAQFTSAICSVVR
55   HDSCSRNLYVSLLLLYQTFG  RKLHLYSHPIILGFRKIPMG  VGLSPFLLAQFTSAICSVVR
56   HDSCSRNLYVSLLLLYQTFG  RKLHLYSHPIILGFRKIPMG  VGLSPFLLAQFTSAICSVVR
57   HDSCSRNLYVSIMLLYQNFG  WKLHLYSHPIVLGFRKIPMG  VGLSPFLLAQFTSAICSVVR
58   HDSCSRQLYVSLLLLYQTFG  RKLHLYSHPIILGFRKIPMG  VGLSPFLLAQFTSAICSVVR
158  HdsCSRnLyVSLlllYktfG  rKLHLYSHPIiLGFRKIPMG  vGLSPFLLAQFTSAICSVVR
```

FIG. 4J

```
     541
39   RAFPHCLAFSYMDDVVLGAK  SVQHLESLFTSITNFLLSLG  IHLNPNKTKRWGYSLNFMGY
40   RAFPHCLAFSYMDDVVLGAK  SVQHLESLFTSITNFLLSLG  IHLNPNKTKRWGYSLNFMGY
41   RAFPHCLAFSYMDDVVLGAK  SVQHLESLFTSITNFLLSLG  IHLNPHKTKRWGYSLNFMGY
42   RAFPHCLAFSYMDDVVLGAK  SVQHLESLFTSITNFLLSLG  IHLNPNKTKRWGYSLNFMGY
43   RAFPHCLAFSYMDDVVLGAK  SVQHLESLFTSITNFLLSLG  IHLNPNKTKRWGYSLNFMGY
44   RAFPHCLAFSYMDDVVLGAK  SVQHLESLFTSITNFLLSLG  IHLNPNKTKRWGYSLNFMGY
45   RAFPHCLAFSYMDDVVLGAK  SVQHLESLFTSITNFLLSLG  IHLNPNKTKRWGYSLNFMGY
47   RAFPHCLAFSYMDDVVLGAK  SVQHLESLYAAVTNFLLSLG  IHLNPNKTKRWGYSLNFMGY
48   RAFPHCLAFSYMDDMVLGAK  SVQHLESLYAAVTNFLLSLG  IHLNPNKTKRWGYSLNFMGY
49   RAFPHCLAFSYMDDVVLGAK  SVQHLESLYAAVTNFLLSLG  IHLNPQKTKRWGYSLNFMGY
50   RAFPHCLAFSYMDDVVLGAK  SVQHLESLYAAVTNFLLSLG  IHLNPQKTKRWGYSLNFMGY
51   RAFPHCLAFSYMDDVVLGAK  SVQHREFLYTAVTNFLLSLG  IHLNPNKTKRWGYSLNFMGY
52   RAFPHCLAFSYMDDVVLGAK  SVQHRESLYTAVTNFLLSLG  IHLNPNKTKRWGYSLNFMGY
53   RAFPHCLAFSYMDDVVLGAK  SVQHLESLFTSITNFLLSLG  IHLNPNKTKRWGYSLNFMGY
54   RAFPHCLAFSYMDDVVLGAK  SVQHLESLFTAVTNFLLSLG  IHLNPNKTKRWGYSLNFMGY
55   RAFPHCLAFSYMDDVVLGAK  SVQHLESLFTAVTNFLLSLG  IHLNPNKTKRWGYSLHFMGY
56   RAFPHCLAFSYMDDVVLGAK  SVQHLESLFTAVTNFLLSLG  IHLNPNKTKRWGYSLHFMGY
57   RAFPHCLAFSYMDDVVLGAK  SVQHLESLFTAVTNFLLSLG  IHLNPNKTKRWGYSLNFMGY
58   RAFPHCLAFSYMDDVVLGAK  SVQHlEsLFTAVTNFLLSLG  IHLNPNKTKRWGYSLNFMGY
158  RAFPHCLAFSYMDDvVLGAK  SVQHlEsLftavTNFLLSLG  IHLNPnKTKRWGYSLnFMGY
```

FIG. 4K

```
     601
 39  VIGSWGTLPQEHIVLKLKQC  FRKLPVNSPIDWKVCQRIVG  LLGFAAPFTQCGYPALMPLY
 40  VIGCWGTLPQEHIVLKIKQC  FRKLPVNRPIDWKVCQRIVG  LLGFAAPFTQCGYPALMPLY
 41  VIGSWGTLPQEHIVLKLKQC  FRKLPVNRPIDWKVCQRIVG  LLGFAAPFTQCGYPALMPLY
 42  VIGSWGTLPQEHIVLKIKQC  FRKLPVNRPIDWKVCQRIVG  LLGFAAPFTQCGYPALMPLY
 43  VIGCWGTLPQEHIVLKIKQC  FRKLPVNRPIDWKVCQRIVG  LLGFAAPFTQCGYPALMPLY
 44  VIGSWGTLPQEHIVLKIKQC  FRKLPVNRPIDWKVCQRIVG  LLGFAAPFTQCGYPALMPLY
 45  VIGSWGTLPQEHIVLKIKQC  FRKLPVNRPIDWKVCQRIVG  LLGFAAPFTQCGYPALMPLY
 47  VIGSWGTWPQDHIVQNFKLC  FRKLPVNRPIDWKVCQRIVG  LLGFAAPFTQCGYPALMPLY
 48  VIGSWGTLPQEHIVQKIMW   FRKLPVNRPIDWKVCQRIVG  LLGFAAPFTQCGYPALMPLY
 49  VIGSWGTLPQEHIVLKIKQC  FRKLPVNRPIDWKVCQRIVG  LLGFAAPFTQCGYPALMPLY
 50  VIGSWGTLPQEHIVLKLKQC  FRKLPVNRPIDWKVCQRIVG  LLGFAAPFTQCGYPALMPLY
 51  VIGSWGTLPQDHIVQKIKHC  FRKLPVNRPIDWKVCQRIVG  LLGFAAPFTQCGYPALMPLY
 52  IIGSWGTLPQDHIVQKIKHC  FRKLPVNRPIDWKVCQRIVG  LLGFAAPFTQCGYPALMPLY
 53  VIGSWGTLPQEHIVQKLKQC  FRKLPVNRPIDWKVCQRIVG  LLGFAAPFTQCGYPALMPLY
 54  VIGCYGSLPQEHIIQKIKEC  FRKLPINRPIDWKVCQRIVG  LLGFAAPFTQCGYPALMPLY
 55  VIGCYGSLPQEHIIQKIKEC  FRKLPVNRPIDWKVCQRIVG  LLGFAAPFTQCGYPALMPLY
 56  VIGCYGSLPQEHIIQKIKEC  FRKLPVNRPIDWKVCQRIVG  LLGFAAPFTQCGYPALMPLY
 57  VIGCYGSLPQDHIVQKIKEC  FRKVPVNRPIDWKVCQRIVG  LLGFAAPFTQCGYPALMPLY
 58  IIGSWGTLPQDHIVQKIKEC  FRKLPVNRPIDWKVCQRIVG  LLGFAAPFTQCGYPALMPLY
158  vIGswGtlPQeHIvqkiKqc  FRKlpvNrPIDWKVCQRiVG  LLGFAAPFTQCGYPALMPLY
```

FIG. 4L

```
    661
39  ACIQSKQAFTFSPTYKAFLC  KQYLNLYPVARQRSGLCQVF  ADATPTGWGLAIGHRRMRGT
40  ACIQSKQAFTFSPTYKAFLC  KQYLNLYPVARQRSGLCQVF  ADATPTGWGLAIGHRRMRGT
41  ACIQSKQAFTFSPTYKAFLC  QQYLHLYPVARQRSGLCQVF  ADATPTGWGLAIGHRRMRGT
42  ACIQSKQAFTFSPTYKAFLC  KQYLHLYPVARQRSGLCQVF  ADATPTGWGLAIGQSRMRGT
43  ACIQSKQAFTFSPTYKAFLC  KQYLNLYPVARQRSGLCQVF  ADATPTGWGLAIGHSRMRGP
44  ACIQSKQAFTFSPTYKAFLC  KQYLHLYPVAR-RTALCQVF  ADATPTGWGLAIGHRRMRGT
45  ACIQSKQAFTFSPTYKAFLC  KQYLHLYPVAR-RTALCQVF  ADATPTGWGLAIGHRRMRCT
47  ACIQSKQAFTFSPTYKAFLS  KQYMTLYPVARQRSGLCQVF  ADATPTGWGLAIGHQRMRGT
48  ACIQAKQAFTFSPTYKAFLT  KQYLNLYPVARQRPGLCQVF  ADATPTGWGLAIGHQRMRGT
49  ACIQAKQAFTFSPTYKAFLN  KQYLNLYPVARQRPGLCQVF  ADATPTGWGLAIGHQRMRGT
50  ACIQAKQAFTFSPTYKAFLT  KQYLNLYPVARQRPGLCQVF  ADATPTGWGLAIGHQRMRGT
51  ACIQAKQAFTFSPTYKAFLS  KQYMNLYPVARQRSGLCQVF  ADATPTGWGLAIGHRRMRGT
52  ACIQAKQAFTFSPTYKAFLC  KQYMNLYPVARQRSGLCQVF  ADATPTGWGLAIGHRRMRGT
53  ACIQSKQAFTFSPTYKAFLC  KQYLNLYPVARQRPGLCQVF  ADATPTGWGLVMGHQRMRGT
54  ACIQSKQAFTFSPTYKAFLC  KQYLNLYPVARQRPGLCQVF  ADATPTGWGLVMGHQRMRGT
55  ACIQSKQAFTFSPTYKAFLC  KQYLNLYPVAGQRPGLCQVF  ADATPTGWGLVMGHQRMRGT
56  ACIQSKQAFTFSPTYKAFLC  KQYLNLYPVARQRPGLCQVF  ADATPTGWGLAMGHQRMRGT
57  ACIQFKQAFTFSPTYKAFLC  KQYLNLYPVARQRPGLCQVF  ADATPTGWGLGMGHQRMRGT
58  ACIQAKQAFTFSPTYKAFLS  KQYLNLYPVARQRPGLCQVF  ADATPTGWGLAIGNQRMRGT
158 ACIQsKQAFTFSPTYKAFLc  kQYlnLyPVArQRpglCQVF  ADATPTGWGLaiGhqrMRGt
```

FIG. 4M

```
      721
 39   FVAPLPIHTAELLAACFARS    RSGAKLIGTDNSVVLSRKYT    SFPWLLGCAANWILRGTSFV
 40   FVAPLPIHTAELLAACFARS    RSGAKLIGTDNSVVLSRKYT    SFPWLLGCAANWILRGTSFV
 41   FVVPLPIHTAELLAACFARS    RSGAKLIGTDNSVVLSRKYT    SFPWLLGCAANWILRGTSFV
 42   FVAPLPIHTAELLAACFARD    RSGAKLIGTDNSVVLSRKYT    SFPWLLGCAANWILRGTSFV
 43   LWLLCRSILRNS
 44   FVAPLPIHTAELLAACFARS    RSGAKLIGTDNSVVLSRKYT    SFPWLLGCAANWILRGTYFV
 45   FVAPLPIHTAELLAACFARS    RSGAKLIGTDNSVVLSRKYT    SFPWLLGCAANWILRGTYFV
 47   FVSPLPIHTAELLAACFARS    RSGANLIGTDNSVVLSRKYT    SFPWLLGCAANWILRGTSFV
 48   FVSPLPIHTAELLAACFARS    RSGAKLIGTDNSVVLSRKYT    SFPWLLGCAANWILRGTSFV
 49   FVSPLPIHTVELLAACFARS    RSGAKLIGTDNSVVLSRKYT    SFPWLLGCAANWILRGTSFV
 50   FVSPLPIHTAELLAACFARS    RSGAKLIGTDNSVVLSRKYT    SFPWLLGCAANWILRGTSFV
 51   FVAPLPIHTAELLAACFARS    RSGAKLIGTDNSVVLSRKYT    SFPWLLGCAANWILRGTSFV
 52   FVAPLPIHTAELLAACFARS    RSGANLIGTDNSVVLSRKYT    SFPWLLGCTANWILRGTSFV
 53   FVAPLPIHTAELLAACFARS    RSGAKLIGTDNSVVLSRKYT    SFPWLLGCAANWILRGTSFV
 54   FSAPLPIHTAELLAACFARS    RSGAKLIGTDNSVVLSRKYT    SFPWLLGCAANWILRGTSFV
 55   FLARLPIHTAELLAACFARS    RSGANIIGTDNSVVLSRKYT    SYPWLLGCAANWILRGTSFV
 56   FSAPLPIHTAELLAACFARS    RSGANILGTDNSVVLSRKYT    SFPWLLGCAANWILRGTSFV
 57   FSAPLPIHTAELLAACFARS    RSGANILGTDNSVVLSRKYT    SFPWLLGCTANWILRGTSFV
 58   IVAPLPIHTAELLAACFARS    RSGAKLIGTDNSVVLSRKYT    SFPWLLGCAANWILRGTSFV
158   fvaplpihtaellaacfars    RSGAkligTDNSVVLSRKYT    SfPWLLGCAaNWILRGTsFV
```

FIG. 4N

```
    781
39  YVPSALNPADDPSRGRLGLY  RPLLLLPFRPTTGRTSLYAV  SPSVPSHLPDRVHFASPLHV
40  YVPSALNPADDPSRGRLGLY  RPLLHLPFRPTTGRTSLYAV  SPSVPSHLPDRVHFPSPLHV
41  YVPSALNPADDPSRGRLGLY  RPLLSLPFQPTTGRTSLYAV  SPSVPSHLPDRVHFASPLHV
42  YVPSALNPADDPSRGRLGLY  RPLLHLPFRPTTGRASLYAV  SPSVPSHLPVRVHFASPLHV
43                                              
44  YVPSALNPADDPSRGRLGLI  RPLLHLRFRPTTGRTSLYAV  SPSVPSHLPDRVHFASPLHV
45  YVPSALNPADDPSRGRLGLI  RPLLHLRFRPTTGRTSLYAV  SPSVPSHLPDRVHFASPLHV
46                                              
47  YVPSALNPADDPSRGRLGLY  RPLLRLPYRPTTGRTSLYAD  SPSVPSHLPDRVHFASPLHV
48  YVPSALNPADDPSRGRLGLY  RPLLRLLYRPTTGRTSLYAD  SPSVPSHLPDRVHFASPLHV
49  YVPSALNPADDPSRGRLGLY  RPLLRLPYRPTTGRTSLYAV  SPSVPSHLPDRVHFASPLHV
50  YVPSALNPADDPSRGRLGLY  RPLLRLPYRPTTGRTSLYAD  SPSVPSRLPDRVHFASPLHV
51  YVPSALNPADDPSRGRLGLY  RPLLRLRLPFRPTTGRTSLYAV  SPSVPSHLPVRVHFASPLHV
52  YVPSALNPADDPSRGRLGLS  RPLLRLPFQPTTGRTSLYAV  SPSVPSHLPDRVHFASPLHV
53  YVPSALNPADDPSRGRLGLS  RPLLHLPFRPTTGRTSLYAD  SPSVPSHLPDRVHFASPLHV
54  YVPSALNPADDPSRGRLGLY  RPLLRLPFRPTTGRTSLYAD  SPSVPSHLPDRVHFASPLHV
55  YVPSALNPADDPSRGRLGLS  RPLLRLPFRPTTGRTSLYAD  SPSVPSHLPDRVHFASPLHV
56  YVPSALNPADDPSRGRLGLS  RPLLRLPFRPTTGRTSLYAD  SPSVPSHLPDLVHFASPLHV
57  YVPSALNPADDPSRGRLGLS  RPLLCLPFRPTTGRTSLYAD  SPSVPSHLPDRVHFASPLHV
58  YVPSALNPADDPSRGRLGLS  RPLLRLPFQPTTGRTSLYAV  SPSVPSHLPVRVHFASPLHI

158 YVPSALNPADDPSRGRLGLy  RPLLrLpfrPTTGRtSLYAV  SPSVPShlPdrVHFaSPLHV
```

FIG. 40

| | |
|---|---|
| 39 | 841 |
| 40 | AWRPP |
| 41 | AWRPP |
| 42 | AWRPP |
| 44 | AWRPP |
| 45 | AWRPP |
| 47 | AWRPP |
| 48 | AWRPP |
| 49 | AWRPP |
| 50 | AWRPP |
| 51 | AWRPP |
| 52 | AWRPP |
| 53 | AWRPP |
| 54 | AWRPP |
| 55 | AWRPP |
| 56 | AWRPP |
| 57 | AWRPP |
| 58 | AWRPP |
| 158 | AWRPP |

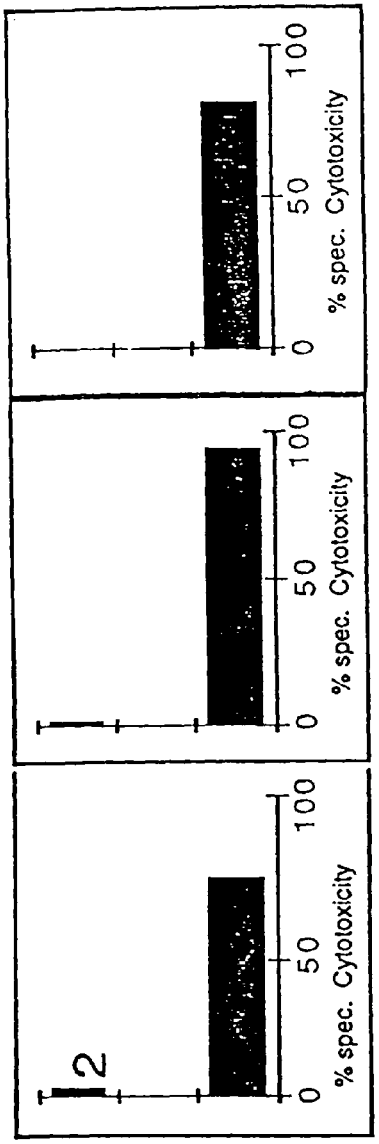
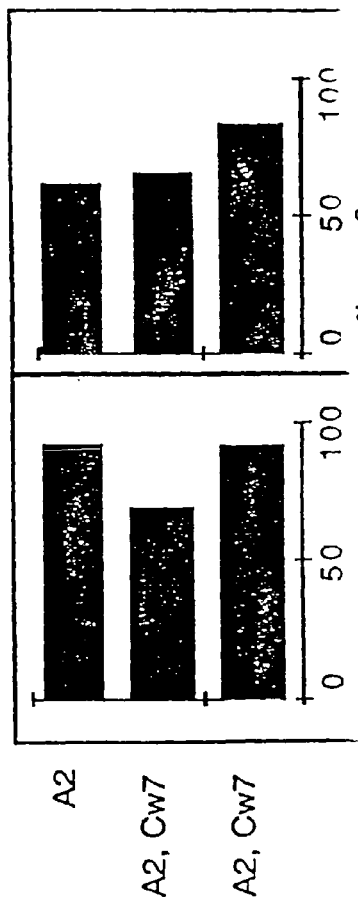
FIG. 8

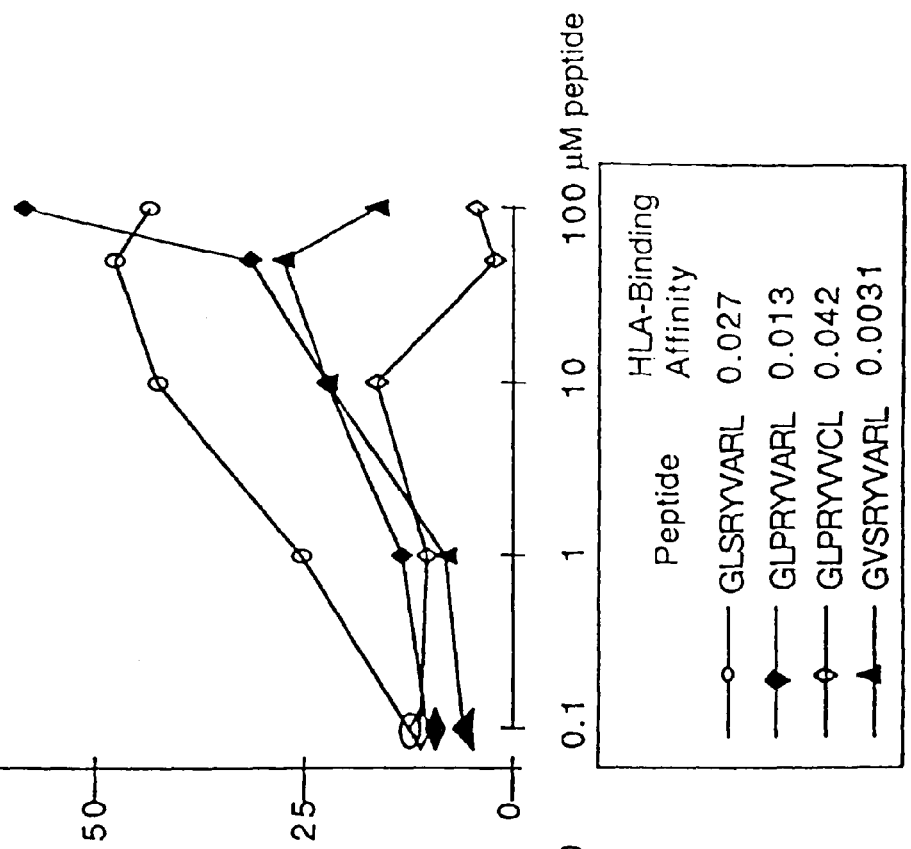
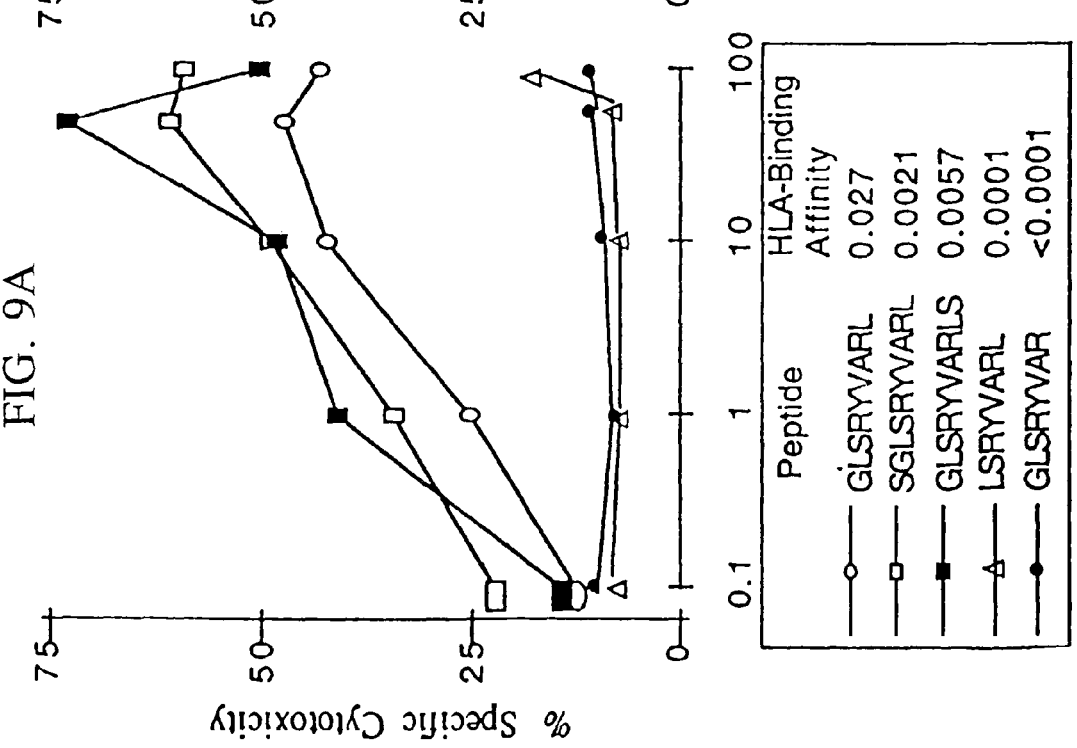
FIG. 9A
FIG. 9B

PEPTIDES FOR INDUCING CYTOTOXIC T LYMPHOCYTE RESPONSES TO HEPATITIS B VIRUS

RELATED APPLICATIONS

The present application is a continuation of U.S. Ser. No. 10/359,431, filed Feb. 5, 2003 now abandoned, which is a divisional of U.S. Ser. No. 08/591,502, filed May 20, 1996, now U.S. Pat. No. 6,607,727, which is the National Stage of International Application Number PCT/US94/08685, filed Aug. 1, 1994, which is a continuation-in-part application of U.S. Ser. No. 08/100,870, filed Aug. 2, 1993 and now abandoned, which is a continuation-in-part of U.S. Ser. No. 07/935,898, filed Aug. 26, 1992 and now abandoned, which is a continuation-in-part of U.S. Ser. No. 07/749,540, filed Aug. 26, 1991 and now abandoned, the disclosures of which are incorporated herein by reference.

GOVERNMENT SUPPORT

This invention was made with government support under Contract No. AI20001 by the National Institutes of Health. The government has certain rights in this invention.

BACKGROUND OF THE INVENTION

Cytotoxic T lymphocytes (CTLs) play an essential role in fighting cells infected with viruses, intracellular bacteria and parasites, and tumor cells. They do so by direct cytotoxicity and by providing specific and nonspecific help to other immunocytes such as macrophages, B cells, and other T cells. Infected cells or tumor cells process antigen through intracellular events involving proteases. The processed antigen is presented on the cellular surface in the form of peptides bound to HLA class I molecules to T cell receptors on CTLs. MHC class I molecules can also bind exogenous peptides and present them to CTLs without intracellular processing.

At the present time it is difficult to accurately predict from the sequence of an antigenic protein how the protein will be processed and which peptide portions will bind HLA class I molecules and be presented to CTLs. Binding motifs have been predicted for some HLA class I molecules based on sequence analysis of peptides eluted from these molecules (Falk et al., *Nature* 351:290 (1991)). Further, of the peptides that are processed and do bind to HLA class I, which ones will contain CTL-recognizable epitopes is not yet predictable.

Hepatitis B Virus ("HBV") is a non-lytic virus which has currently infected approximately 250 million people worldwide. HBV infection in adults typically leads to an acute disease in the majority of cases, and to a chronic disease state in a minority of patients. This ratio of acute to chronic is reversed when the infection occurs close to the time of birth. There is an increased incidence of hepatocellular carcinoma in chronic HBV infection. A small percentage of individuals who are infected with HBV in adulthood develop fulminant hepatitis associated with a strong immune response with high lethality.

While there is no effective treatment for HBV infection, vaccines have been developed in recent years to prevent HBV infection. The vaccines employ either HBV surface antigen (HBsAg) purified from the plasma of chronic HBV carriers, or HBsAg produced by recombinant DNA technology. Synthetic HBsAg peptide-based vaccines have also been proposed. See, for example, U.S. Pat. Nos. 4,599,230 and 4,599,231. The anti-HBsAg vaccines, however, afford protection in only about 90% of immunized individuals. Those who are unimmunized, or immunized but unprotected, provide a significant reservoir of potential infection.

The contribution of CTLs to immunity to HBV antigens has been difficult to assess. Chisari et al. (*Microbial Pathogen.* 6:31 (1989)) have suggested that liver cell injury may be mediated by an HLA-Class I restricted, $CD8^+$ cytotoxic T cell response to HBV encoded antigens. Class I major histocompatibility (MHC)-restricted cytotoxic T lymphocyte responses have been identified for a variety of other viruses, such as influenza. For example, Townsend et al., *Cell* 44:959 (1986) reported that epitopes of an influenza virus nucleoprotein recognized by cytotoxic T lymphocytes could be defined by synthetic peptides. In attempting to define the cytotoxic T lymphocyte response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). Moriyama et al., *Science* 248:361-364 (1990), have reported that the HBV major envelope antigen is expressed at the hepatocyte surface in a form recognizable by envelope-specific antibodies and by MHC class I-restricted, $CD8^+$ cytotoxic T lymphocytes.

As there is a large reservoir of individuals chronically infected with HBV, it would be desirable to stimulate the immune response of these individuals to respond to appropriate HBV antigens and thereby eliminate their infection. It would also be desirable to prevent the evolution to a chronic HBV infection in individuals suffering from an acute phase infection. Further, as the presently approved HBV vaccines do not elicit protective immunity in about 10% of immunized individuals, it would be desirable to elicit more effective immunity, such as by increasing or diversifying the immunogenicity of the vaccines. Quite surprisingly, the present invention fulfills these and other related needs.

SUMMARY OF THE INVENTION

The present invention provides peptides which induce MHC class I restricted cytotoxic T lymphocyte responses against HBV antigen. The peptides of interest are derived from the sequence of the HBV polymerase protein. In certain embodiments the CTL inducing peptide will have the sequence of HBpol-4-13 (Ser-Tyr-Gln-His-Phe-Arg-Lys-Leu-Leu-Leu) [Seq ID No. 12]; HBpol61-69 (Gly-Leu-Tyr-Ser-Ser-Thr-Val-Pro-Val) [Seq ID No. 1]; HBpol108-116 (Arg-Leu-Lys-Leu-Ile-Met-Pro-Ala-Arg) [Seq ID No. 13]; HBpol139-147 (Val-Val-Asn-His-Tyr-Phe-Gln-Thr-Arg) [Seq ID No. 14]; HBpol151-160 (His-Thr-Leu-Trp-Lys-Ala-Gly-Ile-Leu-Tyr) [Seq ID No. 15]; HBpol152-161 (Thr-Leu-Trp-Lys-Ala-Gly-Ile-Leu-Tyr-Lys) [Seq ID No. 16]; HBpol 455-463 (Gly-Leu-Ser-Arg-Tyr-Val-Ala-Arg-Leu) [Seq ID No. 2]; HBpol505-514 (Leu-Tyr-Ser-His-Pro-Ile-Ile-Leu-Gly-Phe) [Seq ID No. 17]; HBpol551-559 (Tyr-Met-Asp-Asp-Val-Val-Leu-Gly-Ala) [Seq ID No. 18]; HBpol575-583 (Phe-Leu-Leu-Ser-Leu-Gly-Ile-His-Leu) [Seq ID No. 19]; HBpol655-663 (Ala-Leu-Met-Pro-Leu-Tyr-Ala-Cys-Ile) [Seq ID No. 20]; HBpol748-757 (Gly-Thr-Asp-Asn-Ser-Val-Val-Leu-Ser-Arg) [Seq ID No. 21]; HBpol758-766 (Lys-Tyr-Thr-Ser-Phe-Pro-Trp-Leu-Leu) [Seq ID No. 22]; HBpol773-782 (Ile-Leu-Arg-Gly-Thr-Ser-Phe-Val-Tyr-Val) [Seq ID No. 3]; HBpol803-811 (Ser-Leu-Tyr-Ala-Asp-Ser-Pro-Ser-Val) [Seq ID No. 4]; and HBpol816-824 (Phe-Leu-Leu-Ser-Leu-Gly-Ile-His-Leu) [Seq ID No. 5]; or will have a sequence substantially homologous to one of the foregoing sequences. The peptide can be optionally flanked and/or modified at one or both of the N- and C-termini, as desired. Conservative substitutions, deletions and additions may be made at non-critical residue positions within the selected peptide without substantially adversely affecting its biological activity.

In the various peptide embodiments it will be understood that the peptides can be polymerized, each to itself to form larger homopolymers, or with different peptides to form heteropolymers. In some instances peptides will be combined in a composition as an admixture and will not be linked. The peptide can also be conjugated to a lipid-containing molecules capable of enhancing a T lymphocyte response, or to a different peptide which induces a T-helper cell response, for example.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective cytotoxic T cell responses against HBpol epitopes. For treating these infections it may be particularly desirable to combine the peptides which induce MHC class I restricted cytotoxic T lymphocyte responses against HBV antigen with other peptides or proteins that induce immune response to other HBV antigens, such as HBV envelope or core. To treat individuals with chronic or carrier state infections the compositions may be administered in repeated dosages over a prolonged period of time, as necessary, to resolve or substantially mitigate the infection and/or shedding of virus.

Vaccine compositions for preventing HBV infection, particularly chronic HBV infection, are also provided. The vaccine compositions comprise an immunogenically effective amount of a HBV polymerase peptide mentioned above which induces a MHC class I restricted cytotoxic T lymphocyte response, such as HLA-A2, -A1, -A3, A-11, and/or -A24, and will typically further comprise an adjuvant, e.g., incomplete Freund's adjuvant or aluminum hydroxide. To achieve enhanced protection against HBV, the vaccine can further comprise components which elicit a protective antibody response to other HBV antigen, such as envelope (surface) antigen.

In yet other embodiments the invention relates to methods for diagnosis, where the peptides of the invention are used to determine the presence of lymphocytes in an individual which are capable of a cytotoxic T cell response to HBV polymerase antigen. The absence of such cells determines whether the individual of interest is susceptible to developing chronic HBV infection. Typically the lymphocytes are peripheral blood lymphocytes and the individual of interest is suffering from an acute HBV infection.

BRIEF DESCRIPTION OF THE DRAWINGS

FIGS. 3A and 3B show that the CTL response to polymerase peptide 803-811 can recognize cells pulsed with peptide and endogenously synthesized polymerase (Vpol), whereas the CTL response to polymerase peptide 61-69 only recognized cells pulsed with the 61-69 peptide.

FIG. 4A-4O show the aligned amino acid sequences of 20 cloned HBV polymerase proteins (SEQ ID NOS:45-64); line 158 is a consensus sequence (SEQ ID NO:11) where capital letters represent 100% consensus, lower case letters represent >50% consensus, and "." is <50% consensus.

FIG. 8 shows HLA-restriction of epitope Pol455-463. Pol455-463-specific lines from patient A-1 and A-2, generated by stimulation with Pol455-463 peptide, were tested against allogeneic partly HLA-matched EBV-B cells prepulsed overnight with 10 µg/ml of the same peptide. Sharing HLA class I at other loci did not render target cells susceptible to lysis. Cytotoxicity was measured at E:T of 50:1 in a 4 hr $^{51}$Cr-release assay.

FIGS. 9A and 9B show recognition of truncated, elongated (SEQ ID NOS:2, 39, 40, 65, and 66) (a) or variant peptides (SEQ ID NOS:2, 38, 43, and 41) (b) by Pol455-463 specific CTL-lines, generated by weekly stimulation of PBMC from patient A-1 with peptide Pol455-463 for 4 weeks. Cytotoxicity was measured at E:T of 50:1 in a 4 hr $^{51}$Cr-release assay against JY-EBV cells prepulsed with varying amounts of the same peptide overnight.

DESCRIPTION OF THE SPECIFIC EMBODIMENTS

Figure 1:
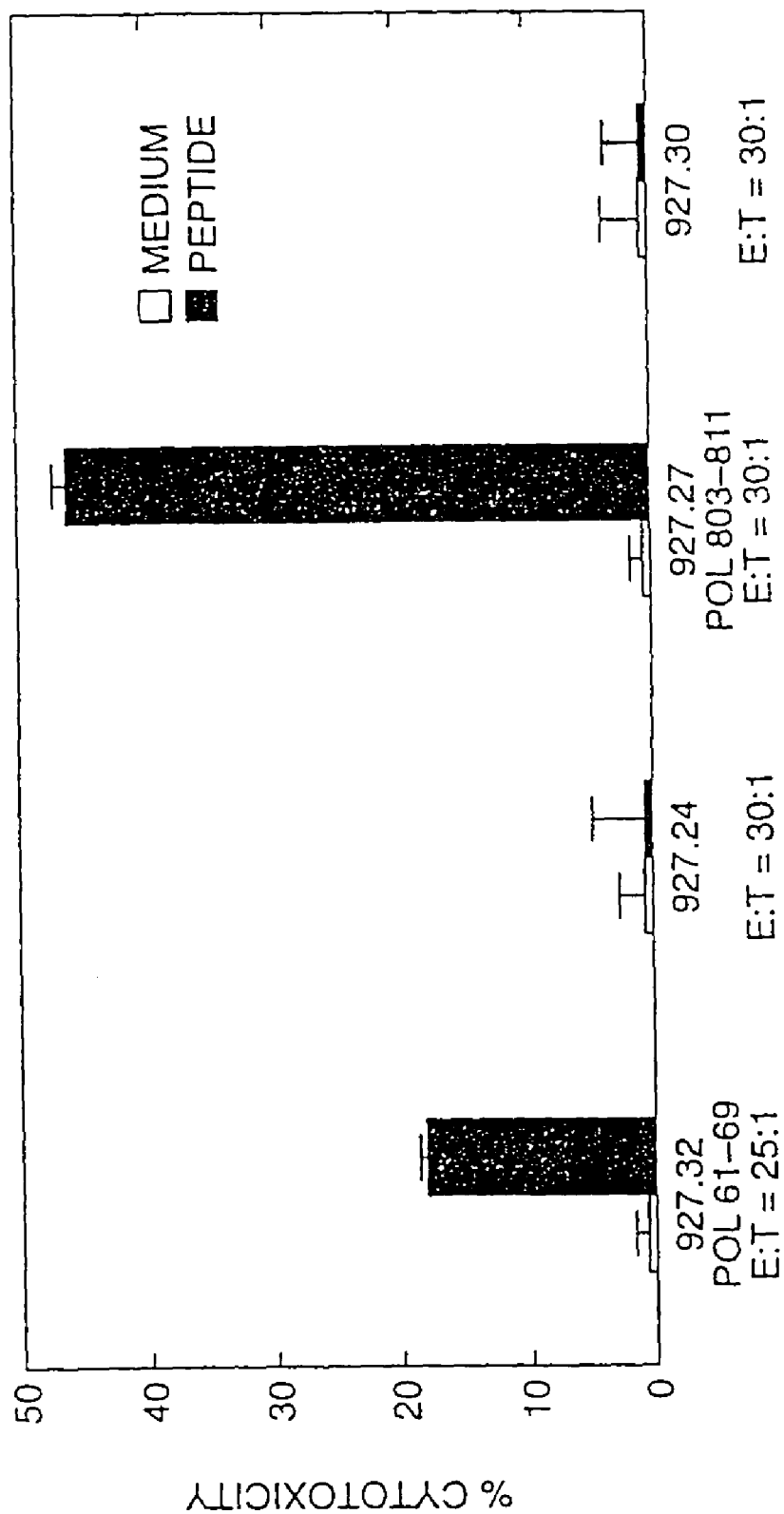
FIG. 1 shows the CTL response to two polymerase peptides that contain the HLA-A2 motif in a patient using target cells pulsed with peptide that match only at HLA-A2.

The present invention provides peptides derived from HBV polymerase proteins for use in compositions and methods for the treatment, prevention and diagnosis of HBV infection. The peptides stimulate MHC HLA-class I restricted cytotoxic T lymphocyte responses against HBV infected cells. The stimulated cytotoxic T lymphocytes are able to kill the infected cells or inhibit viral replication and thus interrupt or substantially prevent infection, including chronic HBV infection. A peptide effective in eliciting a cytotoxic T cell response may also be combined with an immunogen capable of eliciting a T-helper response.

The peptides employed in the invention are derived from the sequence of the HBV polymerase protein (HBpol), particularly CTL epitopes within HBpol4-13, HBpol61-69, HBpol108-116, HBpol139-147, HBpol151-160, HBpol152-161, HBpol 455-463, HBpol505-514, HBpol551-559, HBpol575-583, HBpol655-663, HBpol748-757, HBpol758-766, HBpol773-782, HBpol803-811, or HBpol816-824, where the numbering is according to Galibert et al., supra.

By HBV cytotoxic T lymphocyte inducing "peptide" or "oligopeptide" of the present invention is meant a chain of at least four HBV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues derived from an HBc sequence. It may be desirable to optimize peptides of the invention to a length of eight to twelve amino acid residues, more preferably nine to eleven, commensurate in size with endogenously processed viral peptides that are bound to MHC class I molecules on the cell surface. See generally, Schumacher et al., *Nature* 350:703-706 (1991); Van Bleek et al., *Nature* 348:213-216 (1990); Rotzschke et al., *Nature* 348:252-254 (1990); and Falk et al., *Nature* 351:290-296 (1991), which are incorporated herein by reference. As set forth in more detail below, usually the peptides will have at least a majority of amino acids which are homologous to a corresponding portion of contiguous residues of the HBV pol sequences herein, and contain a CTL-inducing epitope.

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. By biological activity is meant the ability to bind an appropriate MHC molecule and induce a cytotoxic T lymphocyte response against HBV antigen or antigen mimetic. By a cytotoxic T lymphocyte response is meant a CD8+ T lymphocyte response specific for an HBV antigen of interest, wherein CD8+, MHC class I-restricted T lymphocytes are activated. The activated T lymphocytes secrete lymphokines (e.g., gamma interferon) liberate products (e.g., serine esterases) that inhibit viral replication in infected autologous cells or transfected cells, with or without cell killing.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

The peptides of the invention contain CTL-inducing epitopes derived from various epitopic regions of the HBV polymerase protein. The peptides are from the region of $HBpol_{61-69}$ and include peptides derived from those sequence regions which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring $HBpol_{61-69}$ sequence, where $HBpol_{61-69}$ has the following sequence (for HBV subtype ayw):

[Seq. ID No. 1]
($HBpol_{61-69}$)
Gly-Leu-Tyr-Ser-Ser-Thr-Val-Pro-Val,
and

The peptide embodiments of this $HBpol_{61-69}$ region and the other polymerase peptide regions described herein can be optionally flanked and/or modified at one or both of the N- and C-termini, as desired, by amino acids from HBV sequences, including HBpol, amino acids added to facilitate linking, other N- and C-terminal modifications, linked to carriers, etc., as further described herein. The peptide HBpol61-69 induces a cytotoxic T lymphocyte response which is mediated by at least the MHC class I molecule HLA-A2.

Other HBpol region peptides containing CTL epitopes of the invention comprises the peptide HBpol 455-463, and peptides derived from HBpol455-463 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol455-463 sequence, where HBpol 455-463 has the sequence (for HBV subtype ayw):

(HBpol 455-463)                    [Seq ID No. 2]
Gly-Leu-Ser-Arg-Tyr-Val-Ala-Arg-Leu wherein the selected peptide can be flanked and/or modified at one or both termini as described herein. The peptide HBpol 455-463 induces a cytotoxic T lymphocyte response which is mediated by at least the MHC class I molecule HLA-A2.

Yet other HBpol region peptides containing CTL epitopes of the invention comprises the peptide HBpol 773-782, and peptides derived from HBpol773-782 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol773-782 sequence, where HBpol 773-782 has the sequence (for HBV subtype ayw):

[Seq ID No. 3]
(HBpol 773-782)
Ile-Leu-Arg-Gly-Thr-Ser-Phe-Val-Tyr-Val wherein the selected peptide can be flanked and/or modified at one or both termini as described herein. The peptide HBpol 773-782 induces a cytotoxic T lymphocyte response which is mediated by at least the MHC class I molecule HLA-A2. Other HBpol peptide embodiments of the invention are prepared from the region of HBpol803-811. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol803-811 sequence, where HBpol803-811 has the sequence (for HBV subtype ayw):

(HBpol$_{803-811}$)　　　　　　　　　　　　　　[Seq ID No. 4]
Ser-Leu-Tyr-Ala-Asp-Ser-Pro-Ser-Val, wherein the selected peptide can be flanked and/or modified at one or both termini as described herein. The peptide HBpol 803-811 induces a cytotoxic T lymphocyte response which is mediated by at least the MHC class I molecule HLA-A2.

Other HBpol peptide embodiments of the invention are prepared from the region of HBpol816-824. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol816-824 sequence, where HBpol816-824 has the sequence (for HBV subtype ayw):

(HBpol$_{816-824}$)　　　　　　　　　　　　　　[Seq ID No. 5]
Phe-Leu-Leu-Ser-Leu-Gly-Ile-His-Leu, wherein the selected peptide can be flanked and/or modified at one or both termini as described herein. The peptide HBpol 816-824 induces a cytotoxic T lymphocyte response which is mediated by at least the MHC class I molecule HLA-A2.

Other HBpol peptide embodiments of the invention are prepared from the regions of HBpol4-13, HBpol108-116, HBpol139-147, HBpol151-160, HBpol152-161, HBpol505-514, HBpol551-559, HBpol575-583, HBpol655-663, HBpol748-757, or HBpol758-766. A peptide prepared from one of the aforementioned regions contains at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol sequence, where the HBpol regions have the sequences (for HBV subtype ayw):

HBpol4-13　　　　　　　　　　　　　　　　　　[Seq ID No. 12]
Ser-Tyr-Gln-His-Phe-Arg-Lys-Leu-Leu-Leu HBpol108-116　　　　　　　　　　　　　　　　[Seq ID No. 13]
Arg-Leu-Lys-Leu-Ile-Met-Pro-Ala-Arg HBpol139-147　　　　　　　　　　　　　　　　[Seq ID No. 14]
Val-Val-Asn-His-Tyr-Phe-Gln-Thr-Arg HBpol151-160　　　　　　　　　　　　　　　　[Seq ID No. 15]
His-Thr-Leu-Trp-Lys-Ala-Gly-Ile-Leu-Tyr HBpol152-161　　　　　　　　　　　　　　　　[Seq ID No. 16]
Thr-Leu-Trp-Lys-Ala-Gly-Ile-Leu-Tyr-Lys HBpol505-514　　　　　　　　　　　　　　　　[Seq ID No. 17]
Leu-Tyr-Ser-His-Pro-Ile-Ile-Leu-Gly-Phe HBpol551-559　　　　　　　　　　　　　　　　[Seq ID No. 18]
Tyr-Met-Asp-Asp-Val-Val-Leu-Gly-Ala HBpol575-583　　　　　　　　　　　　　　　　[Seq ID No. 19]
Phe-Leu-Leu-Ser-Leu-Gly-Ile-His-Leu HBpol655-663　　　　　　　　　　　　　　　　[Seq ID No. 20]
Ala-Leu-Met-Pro-Leu-Tyr-Ala-Cys-Ile HBpol748-757　　　　　　　　　　　　　　　　[Seq ID No. 21]
Gly-Thr-Asp-Asn-Ser-Val-Val-Leu-Ser-Arg HBpol758-766　　　　　　　　　　　　　　　　[Seq ID No. 22]
Lys-Tyr-Thr-Ser-Phe-Pro-Trp-Leu-Leu wherein the selected peptide can be flanked and/or modified at one or both termini as described herein. The peptide HBpol151-160 induces a CTL response which is mediated by at least the MHC class I molecule HLA-A1. The peptides HBpol551-559 and HBpol655-663 induce a CTL response which is mediated by at least the MHC class I molecule HLA-A2. The peptide HBpol575-583 induces a CTL response which is mediated by at least the MHC class I molecule HLA-A2.1. The peptides HBpol108-116, HBpol139-147, HBpol152-161, and HBpol748-757 induce a CTL response which is mediated by at least the MHC class I molecule HLA-A3 (HBpol748-757 appearing to also be restricted by A24). The peptides HBpol4-13, HBpol505-514, and HBpol758-766 induce CTL responses which are mediated by at least the MHC class I molecule HLA-A24.

As mentioned above, additional amino acids can be added to the termini of an oligopeptide or peptide to provide for ease of linking peptides one to another, for coupling to a carrier, support or a larger peptide, for reasons discussed herein, or for modifying the physical or chemical properties of the peptide or oligopeptide, and the like. Amino acids such as tyrosine, cysteine, lysine, glutamic or aspartic acid, and the like, can be introduced at the C- or N-terminus of the peptide or oligopeptide. In addition, the peptide or oligopeptide sequences can differ from the natural sequence by being modified by terminal-NH$_2$ acylation, e.g., acetylation, or thioglycolic acid amidation, terminal-carboxy amidation, e.g., ammonia, methylamine, etc. In some instances these modifications may provide sites for linking to a support or other molecule.

It will be understood that the HBV peptides of the present invention or analogs or homologs thereof which have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, e.g., the addition or deletion of amino acids on either the amino terminal or carboxy terminal end, or both, of peptides derived from the sequences disclosed herein. The peptides may be modified to substantially enhance the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

The peptides employed in the subject invention need not be identical to peptides HBpol4-13 (Ser-Tyr-Gln-His-Phe-Arg-Lys-Leu-Leu-Leu) [Seq ID No. 12]; HBpol61-69 (Gly-Leu-Tyr-Ser-Ser-Thr-Val-Pro-Val) [Seq ID No. 1]; HBpol108-116 (Arg-Leu-Lys-Leu-Ile-Met-Pro-Ala-Arg) [Seq ID No. 13]; HBpol139-147 (Val-Val-Asn-His-Tyr-Phe-Gln-Thr-Arg) [Seq ID No. 14]; HBpol151-160 (His-Thr-Leu-Trp-Lys-Ala-Gly-Ile-Leu-Tyr) [Seq ID No. 15]; HBpol152-161 (Thr-Leu-Trp-Lys-Ala-Gly-Ile-Leu-Tyr-Lys) [Seq ID No. 16]; HBpol 455-463 (Gly-Leu-Ser-Arg-Tyr-Val-Ala-Arg-Leu) [Seq ID No. 2]; HBpol505-514 (Leu-Tyr-Ser-His-Pro-Ile-Ile-Leu-Gly-Phe) [Seq ID No. 17]; HBpol551-559 (Tyr-Met-Asp-Asp-Val-Val-Leu-Gly-Ala) [Seq ID No. 18]; HBpol575-583 (Phe-Leu-Leu-Ser-Leu-Gly-Ile-His-Leu) [Seq ID No. 19]; HBpol655-663 (Ala-Leu-Met-Pro-Leu-Tyr-Ala-Cys-Ile) [Seq ID No. 20]; HBpol748-757 (Gly-Thr-Asp-Asn-Ser-Val-Val-Leu-Ser-Arg) [Seq ID No. 21]; HBpol758-766 (Lys-Tyr-Thr-Ser-Phe-Pro-Trp-Leu-Leu) [Seq ID No. 22]; HBpol773-782 (Ile-Leu-Arg-Gly-Thr-Ser-Phe-Val-Tyr-Val) [Seq ID No. 3]; HBpol803-811 (Ser-Leu-Tyr-Ala-Asp-Ser-Pro-Ser-Val) [Seq ID No. 4]; or HBpol816-824 (Phe-Leu-Leu-Ser-Leu-Gly-Ile-His-Leu) [Seq ID No. 5], so long as the subject compounds are able to provide for cytotoxic T lymphocytic activity against at least one of the four major subtypes of HBV. Although different strains of HBV exist, they each share at least one common envelope determinant, which is designated "a". Each strain also has two other envelope determinants, one of which is either "d" or "y", and the second is either "w" or "r". Thus, there are four possible subtypes of the virus: adw, ayw, adr, and ayr. The cloning, sequencing and expression of HBV are described in GB 2034323, EP 13828, U.S. Pat. No. 4,935,235, and the complete sequence of the HBV envelope region is also described in Galibert et al., *Nature* 281:646 (1979), each of the foregoing being incorporated herein by reference. Amino acid sequences are described in the GenBank-72 database for 20 different HBV strains, including 7 of the adw subtype, 5 of the ayw subtype, 7 of the adr subtype, and 1 strain of the ayr subtype, the GenBank sequences also being incorporated herein by reference.

Therefore, the peptides may be subject to various changes, such as insertions, deletions, and substitutions, either conservative or non-conservative, where such changes provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV cytotoxic T lymphocyte stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. Where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequences identified by the present invention, including the representative peptides listed above, there are residues (or those which are substantially functionally equivalent) which allow the peptide to retain their biological activity, i.e., the ability to stimulate a class I-restricted cytotoxic T-lymphocytic response against HBV infected cells or cells which express HBV antigen. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid steric and charge interference which might disrupt binding.

Peptides which tolerate multiple substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the invention provides methods for identifying other epitopic regions associated with said peptide regions capable of inducing MHC-restricted cytotoxic T lymphocyte responses against HBV. The methods comprise obtaining peripheral blood lymphocytes (PBL) from infected or uninfected individuals and exposing (stimulating) the cells with synthetic peptide or polypeptide fragments derived from a peptide region of HBpol4-13 (Ser-Tyr-Gln-His-Phe-Arg-Lys-Leu-Leu-Leu) [Seq ID No. 12]; HBpol61-69 (Gly-Leu-Tyr-Ser-Ser-Thr-Val-Pro-Val) [Seq ID No. 1]; HBpol108-116 (Arg-Leu-Lys-Leu-Ile-Met-Pro-Ala-Arg) [Seq ID No. 13]; HBpol139-147 (Val-Val-Asn-His-Tyr-Phe-Gln-Thr-Arg) [Seq ID No. 14]; HBpol151-160 (His-Thr-Leu-Trp-Lys-Ala-Gly-Ile-Leu-Tyr) [Seq ID No. 15]; HBpol152-161 (Thr-Leu-Trp-Lys-Ala-Gly-Ile-Leu-Tyr-Lys) [Seq ID No. 16]; HBpol 455-463 (Gly-Leu-Ser-Arg-Tyr-Val-Ala-Arg-Leu) [Seq ID No. 2]; HBpol505-514 (Leu-Tyr-Ser-His-Pro-Ile-Ile-Leu-Gly-Phe) [Seq ID No. 17]; HBpol551-559 (Tyr-Met-Asp-Asp-Val-Val-Leu-Gly-Ala) [Seq ID No. 18]; HBpol575-583 (Phe-Leu-Leu-Ser-Leu-Gly-Ile-His-Leu) [Seq ID No. 19]; HBpol655-663 (Ala-Leu-Met-Pro-Leu-Tyr-Ala-Cys-Ile) [Seq ID No. 20]; HBpol748-757 (Gly-Thr-Asp-Asn-Ser-Val-Val-Leu-Ser-Arg) [Seq ID No. 21]; HBpol758-766 (Lys-Tyr-Thr-Ser-Phe-Pro-Trp-Leu-Leu) [Seq ID No. 22]; HBpol773-782 (Ile-Leu-Arg-Gly-Thr-Ser-Phe-Val-Tyr-Val) [Seq ID No. 3]; HBpol803-811 (Ser-Leu-Tyr-Ala-Asp-Ser-Pro-Ser-Val) [Seq ID No. 4]; or HBpol816-824 (Phe-Leu-Leu-Ser-Leu-Gly-Ile-His-Leu) [Seq ID No. 5]. Pools of overlapping synthetic peptides, each typically about 8 to 20 residues long, preferably 9-12 residues, can be used to stimulate the cells. Active peptides can be selected from pools which induce cytotoxic T lymphocyte activity. The ability of the peptides to induce specific cytotoxic activity is determined by incubating the stimulated PBL with autologous labeled (e.g., $^{51}$Cr) target cells (such as HLA matched macrophages, T cells, fibroblasts or B lymphoblastoid cells) infected or transfected with the HBV subgenomic fragments thereof, such that the targeted antigen is synthesized endogenously by the cell (or the cell is pulsed with the peptide of interest), and measuring specific release of label.

Once a peptide having an epitopic region which stimulates a cytotoxic T lymphocyte response is identified, the MHC restriction element of the response can be determined. This involves incubating the stimulated PBL or short term lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Carbone et al., *J. Exp. Med.* 167:1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HBV proteins would be undesirable in the development of HBV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HBV antigen, e.g., HBpol. Cells having activity are also stimulated with an appropriate T cell mitogen, e.g., phytohemagglutinin (PHA). The restimulated cells are provided with irradiated allogeneic PBLs as an antigen nonspecific source of T cell help, and HBV antigen. To selectively expand the population of cytotoxic T lymphocytes that recognize native HBV antigen and to establish long term lines, PBL from a patient are first stimulated with peptide and recombinant or native HBV antigen, followed by restimulation with HLA-matched B lymphoblastoid cells that stably express the corresponding HBV antigen polypeptide. The cell lines are re-confirmed for the ability to recognize endogenously synthesized antigen using autologous and allogeneic B-lymphoblastoid or other cells transfected or infected with appropriate antigen.

Having identified different peptides of the invention which contribute to inducing anti-HBV cytotoxic T lymphocyte responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g., the HBpol4-13 (Ser-Tyr-Gln-His-Phe-Arg-Lys-Leu-Leu-Leu) [Seq ID No. 12]; HBpol61-69 (Gly-Leu-Tyr-Ser-Ser-Thr-Val-Pro-Val) [Seq ID No. 1]; HBpol108-116 (Arg-Leu-Lys-Leu-Ile-Met-Pro-Ala-Arg) [Seq ID No. 13]; HBpol139-147 Tyr-Phe-Gln-Thr-Arg) [Seq ID No. 14]; HBpol151-160 (His-Thr-Leu-Trp-Lys-Ala-Gly-Ile-Leu-Tyr) [Seq ID No. 15]; HBpol152-161 (Thr-Leu-Trp-Lys-Ala-Gly-Ile-Leu-Tyr-Lys) [Seq ID No. 16]; HBpol 455-463 (Gly-Leu-Ser-Arg-Tyr-Val-Ala-Arg-Leu) [Seq ID No. 2]; HBpol505-514 (Leu-Tyr-Ser-His-Pro-Ile-Ile-Leu-Gly-Phe) [Seq ID No. 17]; HBpol551-559 (Tyr-Met-Asp-Asp-Val-Val-Leu-Gly-Ala) [Seq ID No. 18]; HBpol575-583 (Phe-Leu-Leu-Ser-Leu-Gly-Ile-His-Leu) [Seq ID No. 19]; HBpol655-663 (Ala-Leu-Met-Pro-Leu-Tyr-Ala-Cys-Ile) [Seq ID No. 20]; HBpol748-757 (Gly-Thr-Asp-Asn-Ser-Val-Val-Leu-Ser-Arg) [Seq ID No. 21]; HBpol758-766 (Lys-Tyr-Thr-Ser-Phe-Pro-Trp-Leu-Leu) [Seq ID No. 22]; HBpol773-782 (Ile-Leu-Arg-Gly-Thr-Ser-Phe-Val-Tyr-Val) [Seq ID No. 3]; HBpol803-811 (Ser-Leu-Tyr-Ala-Asp-Ser-Pro-Ser-Val) [Seq ID No. 4]; or HBpol816-824 (Phe-Leu-Leu-Ser-Leu-Gly-Ile-His-Leu) [Seq ID No. 5] peptides, which peptides can be combined in a "cocktail" to provide enhanced immunogenicity for cytotoxic T lymphocyte responses. Moreover, peptides of one region can be combined with peptides of other HBV regions, from the same or different HBV protein, particularly when a second or subsequent peptide has a MHC restriction element different from the first. Other CTL-inducing HBV peptides are described in co-pending application U.S. Ser. No. 07/935,898 and 08/024,120, which are incorporated herein by reference. This composition of peptides can be used to effectively broaden the immunological coverage provided by therapeutic, vaccine or diagnostic methods and compositions of the invention among a diverse population. For example, the different frequencies of HLA alleles among prevalent ethnic groups (caucasian, asian and african blacks) are shown in Table I below. Therapeutic or vaccine compositions of the invention may be formulated to provide potential therapy or immunity to as high a percentage of a population as possible.

TABLE I

HLA ALLELE FREQUENCIES AMONG PREVALENT ETHNIC GROUPS

| HLA Allele | EUC | NAC | AFR | JPN |
|---|---|---|---|---|
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 7.7 | 9.9 | 16.6 | 1.1 |

Abbreviations:
EUC, European Caucasian;
NAC, North American Caucasian;
AFR, African blacks,
JPN, Japanese.
*A28 represents the two alleles Aw68 and Aw69

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, a peptide which contains T helper epitopes, heteropolymers with repeating units are provided. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyl-dithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl)cyclohexane-1-carboxylate (SMCC). It will be understood that linkage should not substantially interfere with either of the linked groups to function as described, e.g., as an HBV cytotoxic T cell determinant, peptide analogs, or T helper determinant.

In another aspect the peptides of the invention can be combined or coupled with other peptides which present HBV T-helper cell epitopes, i.e., epitopes which stimulate T cells that cooperate in the induction of cytotoxic T cells to HBV. The T-helper cells can be either the T-helper 1 or T-helper 2 phenotype, for example. T-helper epitopes from HBV sequences have been identified at HBc1-20, having the sequence: Met-Asp-Ile-Asp-Pro-Tyr-Lys-Glu-Phe-Gly-Ala-Thr-Val-Glu-Leu-Leu-Ser-Phe-Leu-Pro [Seq ID No. 6]. Other T-helper epitopes are provided by peptides from the region HBc50-69, having the sequence Pro-His-His-Tyr-Ala-Leu-Arg-Gln-Ala-Ile-Leu-Cys-Trp-Gly-Glu-Leu-Met-Tyr-Leu-Ala [Seq ID No. 7], and from the region of HBc100-139, including HBc100-119 having the sequence Leu-Leu-Trp-Phe-His-Ile-Ser-Cys-Leu-Thr-Phe-Gly-Arg-Glu-Thr-Val-Ile-Glu-Tyr-Leu [Seq ID No. 8] (where $Ile_{116}$ is Leu in the HBV adw subtype), HBc117-131 having the sequence Glu-Tyr-Leu-Val-Ser-Phe-Gly-Val-Trp-Ile-Arg-Thr-Pro-Pro-Ala [Seq ID No. 9], and peptide HBc120-139 having the sequence Val-Ser-Phe-Gly-Val-Trp-Ile-Arg-Thr-Pro-Pro-Ala-Tyr-Arg-Pro-Pro-Asn-Ala-Pro-Ile [Seq ID No. 10]. See, Ferrari et al., *J. Clin. Invest.* 88:214-222 (1991), and U.S. Pat. No. 4,882,145, each incorporated herein by reference.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341-347 (1986); and Barany and Merrifield, *The Peptides*, Gross and Meienhofer, eds., Academic Press, New York, pp. 1-284 (1979), each of which is incorporated herein by reference.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, whose disclosures are each incorporated herein by reference. Thus, fusion proteins which comprise one or more peptide sequences of the invention can be used to present the HBV cytotoxic T cell determinants. For example, a recombinant polymerase protein of the invention is prepared in which the HBpol amino acid sequence is altered so as to more effectively present epitopes of peptide regions described herein to stimulate a cytotoxic T lymphocyte response. By this means a polypeptide is used which incorporates several T cell epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range from about 1 μg to about 2,000 mg of peptide for a 70 kg patient, with dosages of from about 10 μg to about 100 mg of peptide being more commonly used, followed by booster dosages from about 1 μg to about 1 mg of peptide over weeks to months, depending on a patient's CTL response, as determined by measuring HBV-specific CTL activity in PBLs obtained from the patient. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals, about 90% of whom are capable of resolving the infection naturally. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3-6 months after infection. As individuals may develop chronic HBV infection because of an inadequate (or absent) cytotoxic T lymphocyte response during the acute phase of their infection, it is important to provide an amount of immuno-potentiating peptide in a formulation and mode of administration sufficient to effectively stimulate a cytotoxic T cell response. Thus, for treatment of chronic hepatitis, a representative dose is in the range of about 1 μg to 1,000 mg, preferably about 5 μg to 100 mg for a 70 kg patient per dose. Administration should continue until at least clinical symptoms or laboratory indicators indicate that the HBV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the cytotoxic T-lymphocyte stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified which are capable of priming CTL in vivo against viral antigens, e.g., tripalmitoyl-5-glycerylcysteinly-seryl-serine ($P_3CSS$), which can effectively prime virus specific cytotoxic T lymphocytes when covalently attached to an appropriate peptide. See, Deres et al., *Nature* 342:561-564 (1989), incorporated herein by reference. Peptides of the invention can be coupled to $P_3CSS$, for example, and the lipopeptide administered to an individual to specifically prime a cytotoxic T lymphocyte response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection.

The concentration of cytotoxic T-lymphocyte stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Science,* 17th ed., Mack Publishing Company, Easton, Pa. (1985), which is incorporated herein by reference.

The peptides of the invention may also be administered via liposomes, which serve to target the peptides to a particular tissue, such as lymphoid tissue or HBV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, the mode of administration, the peptide being delivered, the stage of disease being treated, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the cytotoxic T-lymphocyte stimulatory peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, e.g., lecithin for intranasal delivery.

In another aspect the present invention is directed to vaccines which contain as an active ingredient an immunogenically effective amount of a cytotoxic T-lymphocyte stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., keyhole limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HBV antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 μg to about 500 mg per 70 kilogram patient, more commonly from about 50 μg to about 200 mg per 70 kg of body weight. The peptides are administered to individuals of an appropriate HLA type, e.g., for vaccine compositions of peptides from the region of HBpol61-69 [Seq ID No. 1], Gly-Leu-Tyr-Ser-Ser-Thr-Val-Pro-Val; HBpol 455-463 [Seq ID No. 2], Gly-Leu-Ser-Arg-Tyr-Val-Ala-Arg-Leu; HBpol551-559 and HBpol655-663; HBpol 773-782 [Seq ID No. 3], Ile-Leu-Arg-Gly-Thr-Ser-Phe-Val-Tyr-Val; HBpol803-811 [Seq ID No. 4], Ser-Leu-Tyr-Ala-Asp-Ser-Pro-Ser-Val; or HBpol816-824 [Seq ID No. 5], Phe-Leu-Leu-Ser-Leu-Gly-Ile-His-Leu, these will be administered to at least HLA-A2 individuals. For peptides from HBpol151-160, these will be administered to at least HLA-A1 individuals. Vaccines comprising peptides from HBpol575-583 will be administered to at least. HLA-A2.1 individuals. Vaccines comprising peptides from HBpol575-583 will be administered to at least HLA-A2.1 individuals. Vaccines comprising peptides from HBpol108-116, HBpol139-147, HBpol152-161, and HBpol748-757 will be administered to at least HLA-A3 individuals, and/or A24 individuals in the case of HBpol748-757. The peptides HBpol4-13, HBpol505-514, and HBpol758-766 will be administered to at least HLA-A24 individuals.

In some instances it may be desirable to combine the peptide vaccines of the invention with vaccines which induce neutralizing antibody responses to HBV, particularly to HBV envelope and/or core antigens, such as recombinant HBV env- and/or nucleocapside-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each being incorporated herein by reference. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HBV peptides of the invention. Upon introduction into an acutely or chronically HBV-infected host or into a non-infected host, the recombinant vaccinia virus expresses the HBV peptide and thereby elicits a host cytotoxic T lymphocyte response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456-460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy. By ex vivo therapy is meant that therapeutic or immunogenic manipulations are performed outside the body. For example, lymphocytes or other target cells may be removed from a patient and treated with high doses of the subject peptides, providing a stimulatory concentration of peptide in the cell medium far in excess of levels which could be accomplished or tolerated by the patient. Following treatment to stimulate the CTLs, the cells are returned to the host to treat the HBV infection. The host's cells may also be exposed to vectors which carry genes encoding the peptides, as described above. Once transfected with the vectors, the cells may be propagated in vitro or returned to the patient. The cells which are propagated in vitro may be returned to the patient after reaching a predetermined cell density.

In one method, ex vivo CTL responses to a HBV are induced by incubating in tissue culture a patient's CTL precursor cells (CTLp) together with a source of antigen-presenting cells (APC) and the appropriate immunogenic peptide. After an appropriate incubation time (typically 1-4 weeks), in which the CTLp are activated and mature and expand into effector CTL, the cells are infused back into the patient, where they will destroy their specific target cell (an HBV infected cell). To optimize the in vitro conditions for the generation of specific cytotoxic T cells, the culture of stimulator cells is typically maintained in an appropriate serum-free medium. Peripheral blood lymphocytes are conveniently isolated following simple venipuncture or leukapheresis of normal donors or patients and used as the responder cell sources of CTLp. In one embodiment, the appropriate APC are incubated with about 10-100 µM of peptide in serum-free media for 4 hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of the HBV polymerase antigen from which the peptide sequence was derived. Specificity and MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides.

The induction of CTL in vitro requires the specific recognition of peptides that are bound to allele specific MHC class I molecules on APC. Peptide loading of empty major histocompatibility complex molecules on cells allows the induction of primary CTL responses. Since mutant cell lines do not exist for every human MHC allele, it may be advantageous to use a technique to remove endogenous MHC-associated peptides from the surface of APC, followed by loading the resulting empty MHC molecules with the immunogenic peptides of interest. The use of non-transformed, non-infected cells, and preferably, autologous cells of patients as APC is desirable for the design of CTL induction protocols directed towards development of ex vivo CTL therapies. Typically, prior to incubation of the APCs with the CTLp to be activated, an amount of antigenic peptide is added to the APC or stimulator cell culture, of sufficient quantity to become loaded onto the human Class I molecules to be expressed on the surface of the APCs. Resting or precursor CTLs are then incubated in culture with the appropriate APCs for a time period sufficient to activate the CTLs. Preferably, the CTLs are activated in an antigen-specific manner. The ratio of resting or precursor CTLs to APCs may vary from individual to individual and may further depend upon variables such as the amenability of an individual's lymphocytes to culturing conditions and the nature and severity of the disease condition or other condition for which the described treatment modality is used. Preferably, however, the CTL:APC ratio is in the range of about 30:1 to 300:1. The CTL/APC may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged molecules may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$-$5 \times 10^7$ cells used in mice.

Methods of reintroducing cellular components are known in the art and include procedures such as those exemplified in U.S. Pat. No. 4,844,893 to Honsik, et al. and U.S. Pat. No. 4,690,915 to Rosenberg, which are incorporated herein by reference. For example, administration of activated CTLs via intravenous infusion is typically appropriate.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

Example I

HLA-Restricted CTL Response to HBV Polymerase Epitopes

This Example describes the identification of an HLA-A2 restricted CTL response to two HBV polymerase peptides in a patient with acute viral hepatitis. The epitopes are present in amino acid sequences HBpol$_{61-69}$ [Seq ID No. 1] Gly-Leu-Tyr-Ser-Ser-Thr-Val-Pro-Val (GLYSSTVPV) (also designated peptide 927.32) and HBpol$_{803-811}$ [Seq ID No. 4] Ser-Leu-Tyr-Ala-Asp-Ser-Pro-Ser-Val (SLYADSPSV) (also designated peptide 927.27).

The CTL induced by the HBpol peptides were identified in PBMCs from a patient with acute hepatitis according to the procedure set forth in Example VI of pending application U.S. Ser. No. 07/935,898, except that the PMBCs were stimulated with individual peptides rather than peptide mixtures. The resulting CTL lines and/or clones were then tested for the ability to kill HLA-A2 matched target cells that were either pulsed with the peptide or that expressed the corresponding endogenous polymerase antigen (Vpol or EBO-pol). Construction of the vaccinia based Vpol and Epstein-Barr virus based EBO-pol constructs was as described in Example II of U.S. Ser. No. 07/935,898.

Figure 2:
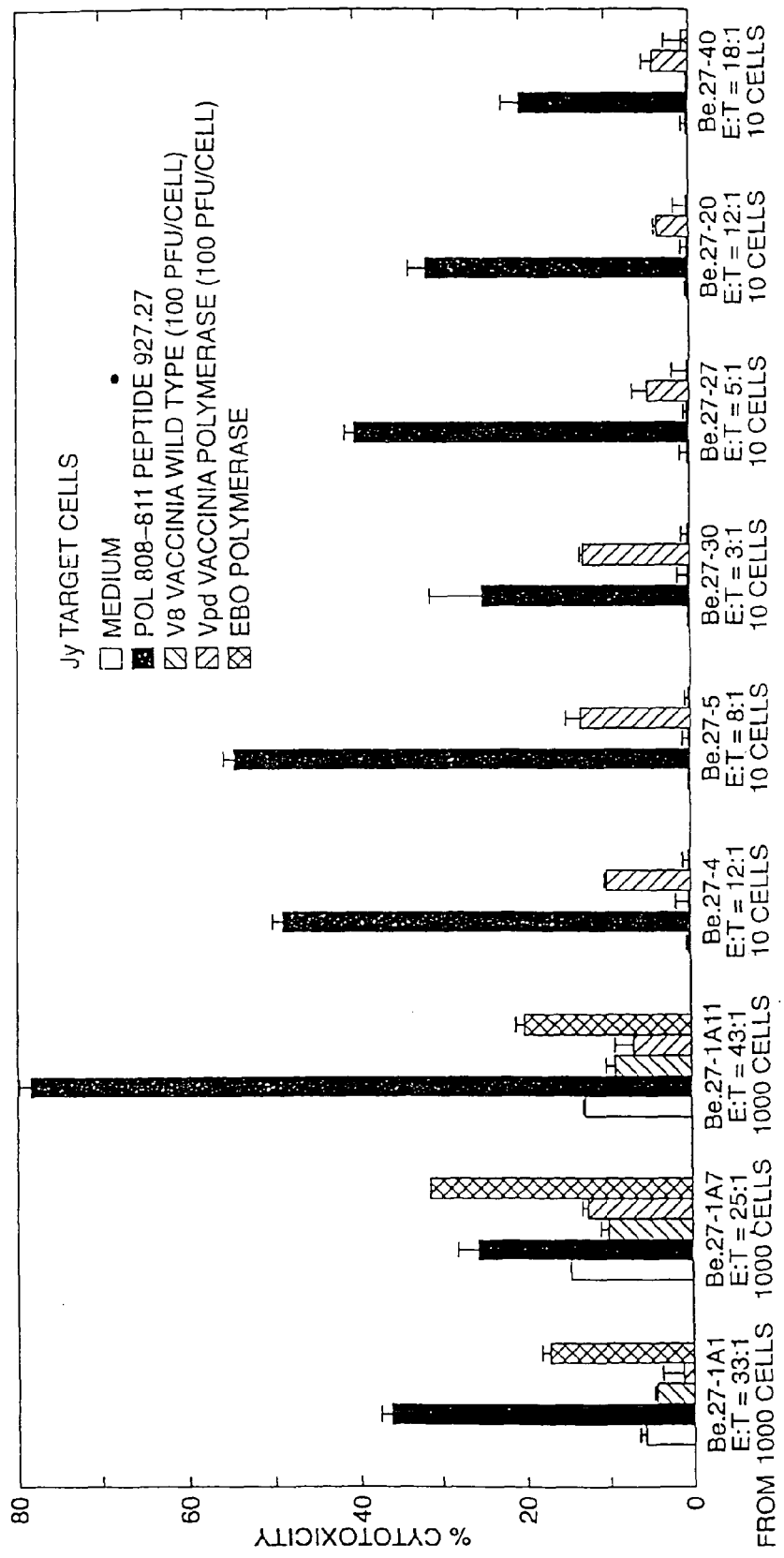
FIG. 2 shows the ability of several polymerase 803-811 peptide specific clones to recognize endogenously synthesized polymerase.

As shown in FIG. 1, both peptides HBpol$_{803-811}$ and HBpol$_{61-69}$ stimulated CTL responses in a patient (HLA-A2$^+$) using target cells pulsed with peptide, whereas other peptides 927.24 (WILRGTSFR) [Seq ID No. 23] and 927.30 (DLNLGNLNV) [Seq ID No. 24] and media controls did not stimulate the specific CTL response. The ability of the HBpol$_{803-811}$ specific clones to recognize endogenously synthesized polymerase antigen (Vpol and EBO-pol) is shown in FIG. 2. Two clones, designated Be.27-1A1 and Be.27-1A5, were identified that recognized the HBpol$_{803-811}$ peptide. As shown in FIG. 3, CTL responses to HBpol$_{61-69}$ and HBpol$_{803-811}$ were shown with target cells pulsed with homologous peptide, but only the HBpol$_{803-811}$ clone showed a response to endogenously synthesized Vpol antigen.

Example II

This example demonstrates that acutely infected patients with clinically apparent viral hepatitis develop an HLA class I restricted CTL response to multiple epitopes in the conserved functional domains of the HBV polymerase protein, while persistently infected patients with chronic hepatitis and normal uninfected controls do not.

Nine HLA-A2 positive patients with acute hepatitis B, nine patients with chronic hepatitis B and ten healthy uninfected subjects were studied (Table II). The diagnosis of acute hepatitis B was based on clinical and biochemical evidence of acute liver injury according to standard diagnostic criteria, together with serological evidence of acute HBV infection, i.e., hepatitis B surface antigen (HBsAg, hepatitis B e antigen (HBeAg) and IgM anti-HBc antibody (IgM HBc-Ab), and the absence of serologic evidence of hepatitis delta or hepatitis C virus infection. Six of the nine patients recovered completely with normalization of serum transaminases and clearance of HBsAg and HBeAg within four months of initial diagnosis; the remaining three patients were lost to follow up. All patients with chronic hepatitis B were repeatedly serologic positive for HBsAg for more than six months and displayed mildly to moderately elevated serum ALT activity. Normal controls had no clinical history of HBV infection and were serologically negative for all HBV markers.

The amino acid sequence of HBV polymerase was screened for 9-mers and 10-mers containing the HLA-A2 allele specific binding motif. This search yielded 220 candidate peptides. Out of this group 44 peptides were selected based on conservation in at least 4 of the 7 HBV adw sequences in the GenBank Database. Lyophilized peptides were reconstituted at 20 mg/ml in DMSO and diluted to 1 mg/ml with RPMI 1640 medium.

TABLE II

Characteristics of Subjects Studied

| Subject | Sex | Diagnosis | HLA class I haplotype |
|---|---|---|---|
| A-1 | Male | Acute | A2, A24, B51, B53, Cw1 |
| A-2 | Male | Acute | A2, A63, B44, B54, Cw7 |
| A-3 | Male | Acute | A2, A24, B27, B71/72, Cw1, Cw4 |
| A-4 | Female | Acute | A2, A31, B51, B6, Cw3 |
| A-5 | Male | Acute | A2, A30, B44, B35, Cw4, Cw7 |
| A-6 | Female | Acute | A2, A69, B53, Cw4 |
| A-7 | Female | Acute | A2, A74, B62, B57, Cw3, Cw6 |
| A-8 | Male | Acute | A2, A68, B58, B27, Cw1, Cw6 |
| A-9 | Male | Acute | A2, A30, B35, Cw5 |
| CH-1 | Male | Chronic | A2, A23, B44 |
| CH-2 | Male | Chronic | A2, A1, B8, B44, Cw7, Cw4 |
| CH-3 | Male | Chronic | A2, A68, B59, B44, Cw5, Cw7 |
| CH-4 | Male | Chronic | A2, B7801, B13, Cw7 |
| CH-5 | Male | Chronic | A2, A30, B44, B13, Cw6 |
| CH-6 | Male | Chronic | A2, A34, B8, B27, Cw7 |
| CH-7 | Male | Chronic | A2, A33, B62, B67, Cw8 |
| CH-8 | Male | Chronic | A2, A69, B41, B52 |
| CH-9 | Male | Chronic | A2, A25, B18, Cw6 |
| N-1 | Female | Normal | A2, A32, B18, B60, Cw3, Cw7 |
| N-2 | Male | Normal | A2, B44, Cw7 |
| N-3 | Male | Normal | A2, A1, B8, B18, Cw7 |
| N-4 | Female | Normal | A2, B44, Cw63 |
| N-5 | Male | Normal | A2, A23, B5, B58, Cw2, Cw6 |
| N-6 | Male | Normal | A2, B35, B56, Cw1, Cw3 |
| N-7 | Male | Normal | A2, A11, B8, B62, Cw4, Cw7 |
| N-8 | Female | Normal | A2, A3, B7, B60, Cw3, Cw7 |
| N-9 | Male | Normal | A2, A11, B35, B44, Cw4 |
| N-10 | Male | Normal | A2, A3, B13, B35, Cw4 |

The binding affinity of the peptides to the class I molecule was determined by competitive binding assays using the radiolabeled peptide FLPSDYFPSV [Seq ID No. 25] representing HBc18-27. The peptide was iodinated to a specific activity of 5–10×10$^7$ cpm/mol by the chloramine T method of Buus et al., Science 235: 1353 (1987), incorporated herein by reference. Purified class I molecules (10 to 50 nM) were incubated at room temp. with various doses of the peptides, together with 5 to 10 nM of the labeled peptide and 1 μM human β2-microglobulin in PBS, pH 7.0, 0.05% NP-40, 1 mM PMSF, 1.3 mM 1,10-phenanthroline, 73 μM pepstatin A, 8 mM EDTA, and 200 μM TLCK. After 48 hrs., class I-peptide complexes were separated from free peptide by gel filtration on either a TSK2000 (7.8 mm×15 cm) column eluted with PBS pH 6.5, 0.5% NP-40, 0.1% NaN$_3$, or a Sephadex G-50 column (22 ml bed volume) eluted with the same buffer at pH 7.0. Class I-bound and free radioactivity was measured and the doses of peptides yielding 50% inhibition of the binding of the labeled peptide (IC50) were calculated. Before conducting inhibition assays, purified class I molecules were titered in the presence of a fixed amount of labeled peptide to determine the concentration necessary to bind 10 to 30% of the total radioactivity added. All subsequent inhibition assays were then performed using these class I concentrations. Each peptide was tested in two to four independent experiments.

Fifteen of the peptides displayed an HLA-A2.1 binding affinity ratio greater than 0.01 (Table III), a threshold below which most peptides are not immunogenic. In addition two peptides which contain HLA-A2 restricted CTL epitopes were included for comparison, HBc18-27 and HBs335-343.

anti-CD4 coated flasks (Applied Immunosciences, Santa Clara, Calif.) and restimulated as described above.

CTL lines were established as described above and enriched in highly cytotoxic CD8+ CTLs by cloning at 10 and 3 cells per well in 96-well microwell plates in the presence of 0.5 μg/ml CD3-specific monoclonal antibody (Coulter Immunology, Hialeah, Fla.), rIL-2 (100 U/ml) and $10^5$ irra-

TABLE III

Characteristics of Peptides Tested

| Peptide | Amino Acid Sequence | Seq ID No. | Frequency in HBV subtypes | | | | Binding affinity | Acute HBV patients | | %51Cr Release | |
|---|---|---|---|---|---|---|---|---|---|---|---|
| | | | total (20) | adw (7) | ayw (5) | adr (7) | ayr (1) | | tested | Responders | Mean | Range |
| Pol527-53 | LLAQFTSAI | 26 | 19 | 6 | 5 | 7 | 1 | 9.6000 | 2 | 0 | | |
| *Pol575-583 | FLLSLGIHL | 19 | 19 | 6 | 5 | 7 | 1 | 0.5200 | 9 | 6 | 38 | 16-81 |
| *Pol816-824 | SLYADSPSV | 5 | 8 | 4 | 4 | 0 | 0 | 0.3500 | 9 | 3 | 30 | 25-32 |
| Pol502-510 | KLHLYSHPI | 27 | 19 | 6 | 5 | 7 | 1 | 0.2900 | 3 | 0 | | |
| *Pol655-665 | ALMPLYACI | 28 | 19 | 6 | 5 | 7 | 1 | 0.2000 | 5 | 2 | 19 | 17-21 |
| *Pol551-559 | YMDDVVLGA | 18 | 18 | 5 | 5 | 7 | 1 | 0.1600 | 7 | 2 | 21 | 17-25 |
| Pol504-512 | HLYSHPIIL | 29 | 16 | 4 | 4 | 7 | 1 | 0.1300 | 2 | 0 | | |
| *Pol455-463 | GLSRYVARL | 2 | 11 | 7 | 4 | 0 | 0 | 0.1200 | 9 | 6 | 57 | 20-95 |
| Pol526-535 | FLLAQFTSAI | 30 | 19 | 6 | 5 | 7 | 1 | 0.0710 | 2 | 0 | | |
| Pol149-158 | YLHTLWKAGI | 31 | 20 | 7 | 5 | 7 | 1 | 0.0560 | 3 | 0 | | |
| Pol772-780 | WILRGTSFV | 32 | 16 | 6 | 5 | 4 | 1 | 0.0180 | 4 | 0 | | |
| *Pol773-782 | ILRGTSFVYV | 3 | 16 | 6 | 5 | 4 | 1 | 0.0160 | 7 | 3 | 18 | 16-21 |
| Pol765-774 | LLGCAANWIL | 33 | 16 | 6 | 5 | 4 | 1 | 0.0140 | 2 | 0 | | |
| Pol424-432 | NLSWLSLDV | 34 | 18 | 5 | 5 | 7 | 1 | 0.0130 | 3 | 0 | | |
| *Core18-27 | FLPSDFPPSV | 35 | 9 | 5 | 4 | 0 | 0 | 1.5000 | 9 | 4 | 64 | 54-78 |
| *Env335-343 | WLSLLVPFV | 36 | 20 | 7 | 5 | 7 | | 0.7200 | 9 | 6 | 66 | 21-88 |

To stimulate PBMC with the selected synthetic peptides and rHBcAg, PBMC from patients and normal donors were separated on Ficoll-Histopaque density gradients, washed three times in Hanks Balanced Salt Solution (HBSS), resuspended in RPMI 1640 supplemented with L-glutamine (2 mM), gentamicin (10 μg/ml), and 10% heat-inactivated human AB serum and plated in a 24-well plate at $4\times10^6$ cells/well. rHBcAG (Biogen, Cambridge, Mass.) was added to the cell cultures at 1 μg/ml and the synthetic peptides at 10 μg/ml. In some of the studies with healthy uninfected blood donors rHBcAg was either omitted or replaced by 10 μg/ml tetanus toxoid (Connaught Laboratories, Swiftwater, Pa.) since these individuals had not been previously exposed to HBV and did not benefit from rHBcAg-induced T cell help. On days 3 and 10, 1 ml of RPMI with 10% human AB serum and rIL-2 at 10 U/ml final concentration was added to each well. On day 7, the cultures were restimulated with peptide, rIL-2 and irradiated (3000 rad) autologous feeder cells and they were tested for cytotoxic activity on day 14. Selected cultures that displayed peptide specific cytolytic activity were separated into CD4+ and CD8+ populations by panning onto diated (3000 rad) allogeneic PBMC. HBV specific clones were established by cloning at 1 and 0.3 cells per well in the same way. Growing cultures were tested for cytotoxic activity against peptide-primed target cells on day 17 and cytotoxic lines and clones were expanded in a 24-well plate and restimulated every 7 to 10 days as described above.

For the cytotoxicity assays, target cells consisted of either 1) allogeneic HLA-matched and mismatched B-LCL (Amer. Soc. Histocompat. Immunogenetics, Boston, Mass.), incubated overnight with synthetic peptides at 10 μg/ml; 2) stable B-LCL transfectants that express HBsAg or HBpolAg produced by transfection of the EBV-transformed B-LCL with a panel of EBV-based expression vectors that contain the corresponding coding regions of the ayw subtype (Guilhot et al., *J. Virol.* 66: 2670 (1992), incorporated herein by reference); or 3) B-LCL infected with recombinant vaccinia viruses (a recombinant vaccinia virus construct that encodes the HBV polymerase protein (Vpol) was produced by insertion of a 2766 fragment representing nucleotides 2290-1874 of the HBV genome (ayw subtype) into the Sma I site of the pSCII vector by standard techniques as described in Chakrabarti et al., *Mol. Cell. Biol.* 5: 3403 (1985), incorporated herein by reference. Vaccinia-infected targets were prepared by infection of $10^6$ cells at 50 PFU/cell on a rocking plate at room temp. for 1 h followed by a single wash and overnight incubation at 37° C. Target cells were then labeled with 100 μCi of $^{51}$Cr (Amersham Corp., Arlington Heights, Ill.) for 1 h and washed four times with HBSS. Cytolytic activity was determined in a standard 4-h $^{51}$Cr release assay using U-bottomed 96-well plates containing 5,000 targets/well. Stimulated PBMC from patients and normal controls were performed in duplicate. Percent cytotoxicity was determined from the formula 100×((experimental release−spontaneous release)/(maximum release−spontaneous release)). Maximum release was determined by lysis of targets by detergent (1% Triton X-100; Sigma Chemical Co., St. Louis, Mo.). Spontaneous release was <20% of maximal release in all assays. The assay was considered positive if the specific $^{51}$Cr release from target cells containing antigen was ≧15% higher than the nonspecific $^{51}$Cr release from antigen nonspecific $^{51}$Cr release from antigen negative target cells and the nonspecific lysis was less than 15% of maximum.

As shown in Table III, eight of the nine acutely infected patients responded to at least one of the polymerase peptides and, as can be seen from Table III, six of the peptides were recognized by at least one patient, suggesting that they represented HLA-A2 restricted epitopes. The HLA binding ratio of 5 of 6 of these peptides was greater than 0.1, supporting a direct relationship between binding affinity and immunogenicity even among this group of high affinity peptides.

The HLA-A2 binding affinity of a peptide did not appear to be the only requirement for immunogenicity since the peptide (LLAQFTSAI) [Seq ID No. 26] with the highest binding affinity (9.600) did not elicit an immune response while one with a 600-times lower affinity (0.016) did. To exclude the possibility that this extremely high affinity peptide may have triggered potentially responsive CTL precursors to undergo apoptosis, PBMC were also stimulated with lower concentrations of this peptide (0.3, 1, 3 and 10 μg/ml) without inducing a CTL response, suggesting that nonresponsiveness to this and other high affinity peptides is probably due to other mechanisms.

Figure 5:
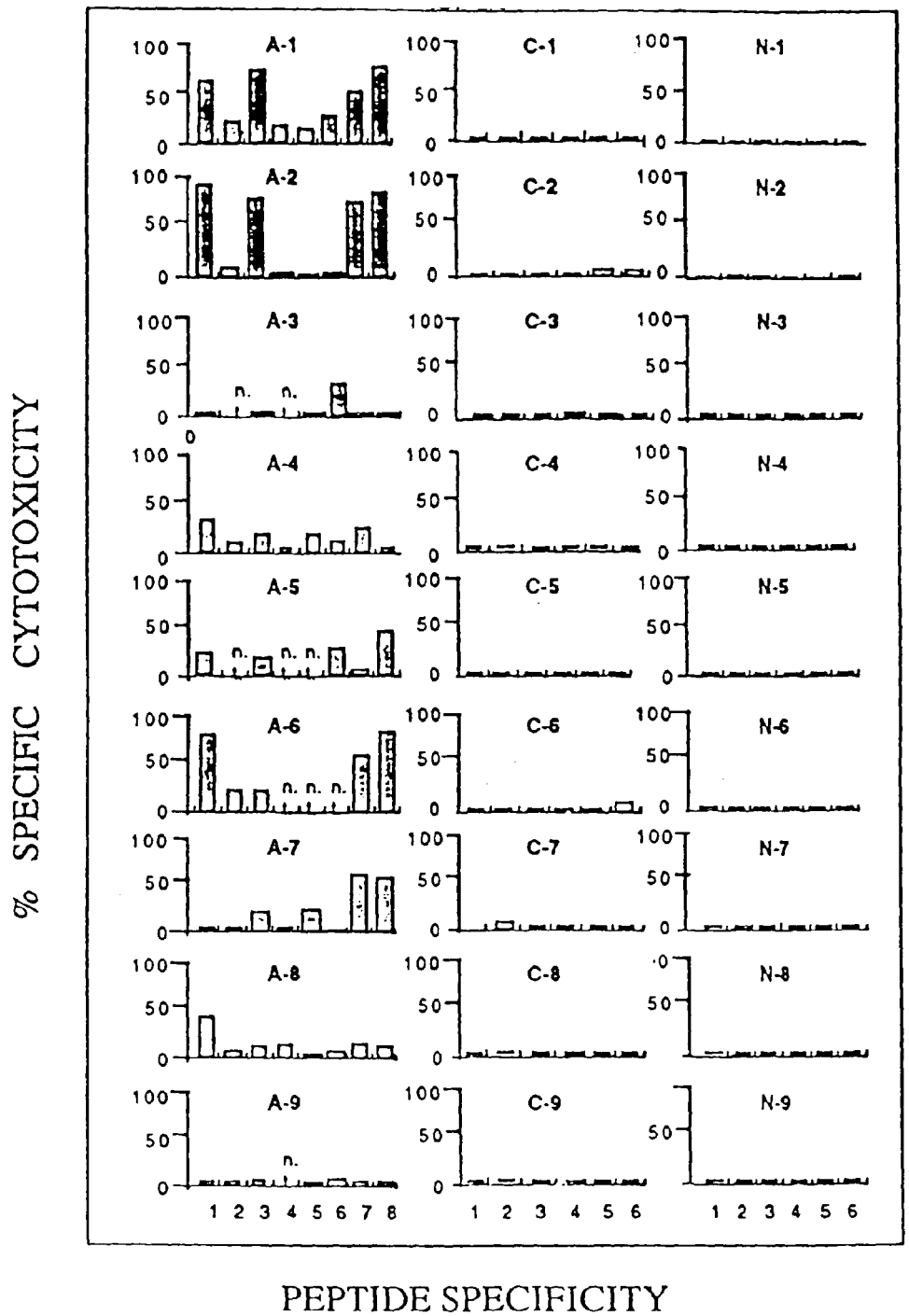
FIG. 5 shows HBV specific CTL response in patients with acute hepatitis (A-1-A-9), chronic hepatitis (C-1-C-9) and normal subjects (N-1-N-9). PBMC were stimulated with the peptides indicated for 2 weeks and tested in a 4-h $^{51}$Cr-release assay against JY target cells prepulsed overnight with the same peptide. Peptide-specific cytotoxicity was measured by subtracting the $^{51}$Cr-release by JY target cells not prepulsed with the peptide from the $^{51}$Cr-release by JY target cells prepulsed with the peptide. Results shown represent percent specific lysis in a 4 hr $^{51}$Cr-release assay at an E:T of 50:1.

The CTL responses of nine acutely infected patients who responded to one or more polymerase peptides are summarized in FIG. 5. Five of these patients also recognized the two control peptides, HBc18-27 and HBenv335-343, while one patient recognized only HBenv335-343, and one patient responded to neither. These results demonstrate the clonality and multispecificity of the CTL response against the polymerase protein during acute viral hepatitis. Importantly, nine of the 10 uninfected controls responded to any of the peptides used in this example (nine of these controls are shown in FIG. 5), suggesting that the CTL responses observed in the acutely infected patients represented in vitro secondary responses that were primed by exposure to infected cells in vivo. None of the nine patients with chronic hepatitis produced a response, suggesting that the vigor of the HBV specific CTL response has a role in determining which patients will clear the virus and which patients will not.

Figure 6:
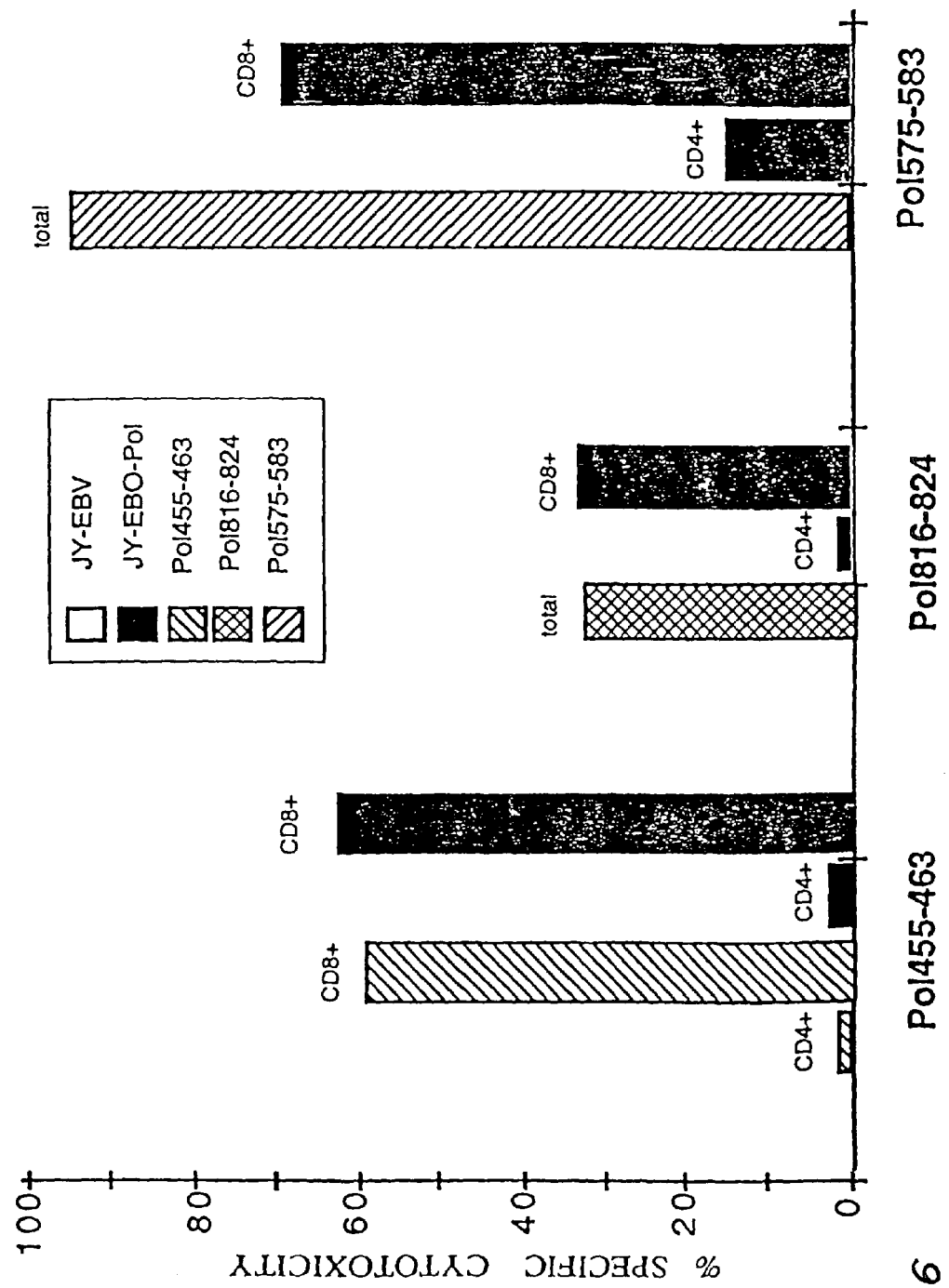
FIG. 6 shows CD8+ cells recognize endogenously synthesized antigen in target cells sharing the HLA-A2 allele (Patient A-1). Epitope-specific lines were generated by stimulating PBMC with the individual peptide for three weeks with weekly restimulation. On day 15 of CD4+ (positive selection) and CD8+ (negative selection) enriched lines were generated from the original bulk culture by panning. FACS-analysis showed an average enrichment by a factor of 3. Results shown represent percent specific lysis in a 4 hr $^{51}$Cr-release assay at an E:T of 30:1. Targets (JY-EBV) were either pulsed with the corresponding peptide overnight stably transfected with the polymerase expression vector.

Having identified two HLA-A2 patients (A-1 and A-2) with acute hepatitis who responded strongly to HBpol575-583 and HBpol455-463 and HBpol816-824 (Table III), these patients and peptides were chosen for further analysis. After two weeks of in vitro stimulation, selected cultures that displayed peptide specific CTL responses were enriched for CD4+ and CD8+ subsets by panning using positive and negative selection, respectively, and they were restimulated with peptide and tested for recognition of endogenously processed polymerase antigen after one additional week of culture. As shown in FIG. 6, the CTL response to these epitopes was mediated by CD8+ T cells since only the CD8+ fraction of each cell line recognized target cells that were either pulsed with the corresponding peptide or stably transfected with the polymerase expression vector. These results suggest that the peptides represent the native epitopes that are produced by the cellular processing of the polymerase protein, and that they are presented in the context of class I HLA molecules.

To obtain pure CD8+ cell lines and to characterize the T cell response at the clonal level, each of the three responding cell lines was cloned by limiting dilution in the presence of anti-CD3, irradiated allogeneic PBL and IL-2. All of the derivative cytotoxic lines were highly enriched in CD8+ cells as determined by FACS analysis (0.5-1.0×$10^6$ cells were washed once in PBS with 5% BSA and 0.02% sodium azide, the pelleted cells were then stained with a fluorescent probe-conjugated anti-CD4 and anti-CD8 monoclonal antibody (Leu3a or Leu2a), and similarly labeled control antibody for 30 min. at 4° C., and after 3 washes in PBS with 5% BSA and 0.02% sodium azide, cells were analyzed with a FACScan flow cytometer). Furthermore, 5 of the 6 HBpol455-463 specific CTL clones derived in this manner also consisted of CD8+ cells.

Figure 7:
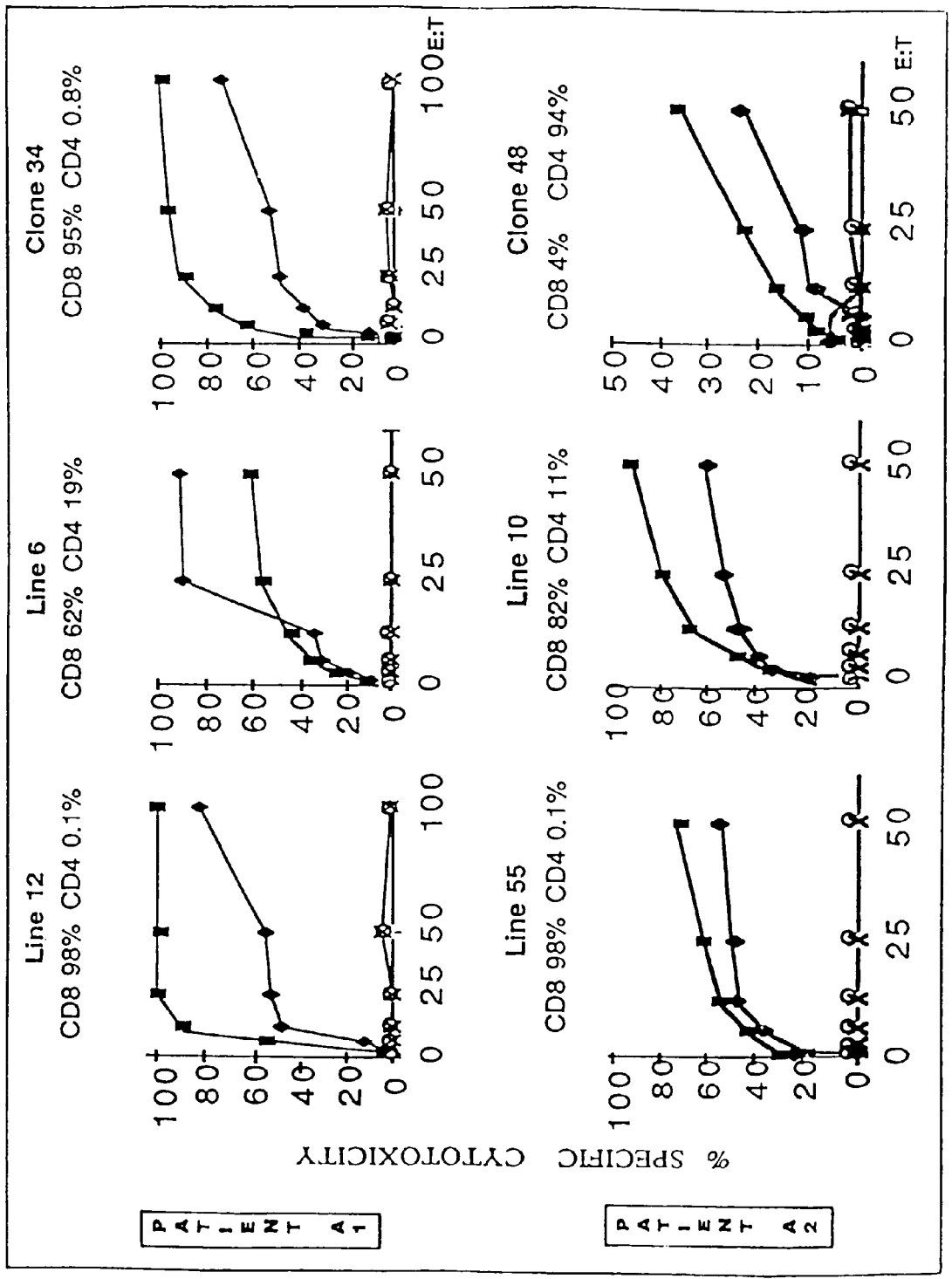
FIG. 7 shows CTL-response to Pol455-463 GLSRYVARL [Seq ID No. 2]. Epitope-specific lines and clones, generated by stimulation with Pol455-463 peptide, were tested at varying E:T ratios against targets cells (JY-EBV), pulsed with the corresponding peptide (■) overnight or infected with recombinant vaccinia virus that express the HBV polymerase polypeptide (♦), in a standard 4 hr $^{51}$Cr-release assay. Wild-type vaccinia virus (Wt) (X) or JY-EBV peptides without peptide (○) were used as a control.

Four highly cytotoxic long term CTL lines and two clones specific for HBpol455-463 pulsed targets were chosen for further analysis (FIG. 7). The strength of the cytotoxic activity was assessed by varying the amount of the peptide used to pulse the target cells and by varying the effector to target ratios. The CTL displayed peptide dose dependent cytotoxic activity that recognized targets pulsed with peptide concentrations as low as 10 nM (Table IV), and they efficiently lysed both peptide pulsed and vaccinia-pol infected targets at E:T ratios as low as 1.6:1 (FIG. 7). Target cells pulsed with no peptide or with an irrelevant peptide (Table V), which is an HLA-A2 restricted epitope in HCV-infected patients, were not lysed, now were cells infected by the control recombinant vaccinia virus that expresses the HBV envelope protein, indicating the specificity of the CTL.

TABLE IV

Recognition GLSRYVARL-pulsed JY-EBV by CTL is peptide-dose dependent [Seq ID No. 2]

| | | JY-EBV pulsed with | | | | |
|---|---|---|---|---|---|---|
| Patient | Line | 10 μM GLSRYVARL | 1 μM GLSRYVARL | 0.1 μM GLSRYVARL | 0.01 μM GLSRYVARL | no peptide |
| A-1 | 67-68 | 41% | 26% | 19% | 13% | 5% |
| A-2 | 10 | 75% | 56% | 52% | 25% | 12% |
| A-2 | 30 | 69% | 40% | 40% | 19% | 6% |

TABLE V

Induction of CTL with variant peptides to GLSRYVARL [Seq ID No. 2] and an HCV epitope KLVALGINAV [Seq ID No. 37]

| Peptide During CTL-Induction | % Specific Cytotoxicity Against JY-EBV Preincubated with | | | | |
|---|---|---|---|---|---|
| | GLSRYVARL Seq ID 2 | GLPRYVARL Seq ID 38 | SGLSRYVARL Seq ID 39 | GLSRYVARLS Seq ID 40 | KLVALGINAV Seq ID 37 |
| GLSRYVARL | 54% | 18% | 40% | 41% | 2% |
| GLPRYVARL | 1% | 0% | 1% | 0% | |
| SGLSRYVARL | 0% | 0% | 0% | 0% | |
| GLSRYVARLS | 1% | 1% | 0% | 0% | |

To identify the restriction element used by the HBpol455-463 specific CTL, cytotoxic lines and clones from patients A-1 and A-2 were tested against allogeneic EBV-B cell lines sharing individual HLA class I alleles with the effector cells. As shown in FIG. 8, not only was HLA-A2 the sole class I allele shared by these two patients, but their CTL only lyse peptide pulsed target cells that share this allele. Thus, HBpol455-463 specific CTLs from both patients are HLA-A2 restricted.

Peptides containing carboxy- and amino-terminal truncations and elongations of the HBpol455-463 sequence were synthesized to determine the optimal length and the precise termini of the epitope. As shown in FIG. 9A, truncation of Gly455 or Leu463 greatly reduced the HLA binding affinity of the peptides and totally abrogated their recognition by CTL induced by the original peptide HBpol455-463. Elongation of this peptide by adding a single Ser residue normally present upstream of the amino terminus or downstream of the carboxy-terminus of HBpol455-463 did not diminish its recognition by CTL (FIG. 9A), and may have even increased recognition, despite the fact that the HLA-A2 binding affinity of the extended peptides was reduced 4-10 fold relative to the original peptide (FIG. 9A). The Ser-extended peptides did not induce CTL, as shown in Table V.

Direct sequencing of the PCR products amplified from the serum of 5 of the 9 patients with acute hepatitis B by nested PCR demonstrated that the deduced HBV amino acid sequence was identical to GLSRYVARL [Seq ID No. 2] in these patients. The sequence is present in 7/7 and 4/5 adw and ayw subtype sequences in GenBank. The amino acid sequence of the remaining ayw isolate in the database is GVSRYVARL [Seq ID No. 41], while the sequence of 6/7 adr and 1/1 ayr isolates is GLPRYVARL [Seq ID No. 42] and the sequence of the remaining adr isolate is GLPRYVVCL [Seq ID No. 43].

Peptides containing sequences of these different viral subtypes were tested for recognition by GLSRYVARL-stimulated [Seq ID No. 2] PBMC to assess cross-reactivity of the CTL response. None of the variants was efficiently recognized by the CTL. GLSRYVVCL [Seq ID No. 44] was not recognized, even at very high peptide concentration, despite the fact that its HLA-A2.1 binding affinity was greater than the prototype peptide GLSRYVARL [Seq ID No. 2]. Thus, Ser457, Ala461 and Arg462 may represent T cell receptor contact sites (epitope residues) in this peptide. A substitution in Ser457 in GLPRYVARL [Seq ID No. 42] variant yielded more than a 10-fold reduction in its recognition by the CTL, while decreasing the HLA binding affinity 2-fold.

The GVSRYVARL [Seq ID No. 41] variant which contained the substitution at Leu456, a presumptive HLA contact site (agretope residue), was poorly recognized by the CTL, commensurate with the 9-fold reduction in its HLA-A2 binding affinity. However, the amino- and carboxy-terminally extended peptides described above were well recognized by the CTL despite the fact that they displayed comparably reduced HLA-A2 binding affinities (FIG. 9A). This suggests that Leu456 not only serves as an agretope residue, but may also influence the T cell receptor binding affinity of the peptide.

All publications, patents and patent applications mentioned in this specification are herein incorporated by reference into the specification to the same extent as if each individual publication, patent or patent application was specifically and individually indicated to be incorporated herein by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An HBV immunogenic peptide of 50 amino acids or less in length, wherein said immunogenic peptide comprises $HB_{pol}$ 526-535 (Phe-Leu-Leu-Ala-Gln-Phe-Thr-Ser-Ala-Ile; SEQ ID NO:30), and wherein said immunogenic peptide binds to an appropriate HLA molecule to form a complex recognized by cytotoxic T cells wherein said cytotoxic T cells recognize a native HBV antigen.

2. The HBV immunogenic peptide of claim 1, wherein said immunogenic peptide is 25 amino acids or less in length.

3. The HBV immunogenic peptide of claim 1, wherein said immunogenic peptide is 10 or 11 amino acids in length.

4. The HBV immunogenic peptide of claim 1, wherein said immunogenic peptide consists of $HB_{pol}$ 526-535 (Phe-Leu-Leu-Ala-Gln-Phe-Thr-Ser-Ala-Ile; SEQ ID NO:30).

5. An immunogenic composition comprising an HBV immunogenic peptide of 50 amino acids or less in length and a pharmaceutically acceptable carrier, wherein said immunogenic peptide comprises $HB_{pol}$ 526-535 (Phe-Leu-Leu-Ala-Gln-Phe-Thr-Ser-Ala-Ile; SEQ ID NO:30), and wherein said immunogenic peptide binds to an appropriate HLA molecule to form a complex recognized by cytotoxic T cells wherein said cytotoxic T cells recognize a native HBV antigen.

6. The immunogenic composition of claim 5, wherein said immunogenic peptide is 25 amino acids or less in length.

7. The immunogenic composition of claim 5, wherein said immunogenic peptide is 10 or 11 amino acids in length.

8. The immunogenic composition of claim 5, wherein said immunogenic peptide consists of $HB_{pol}$ 526-535 (Phe-Leu-Leu-Ala-Gln-Phe-Thr-Ser-Ala-Ile; SEQ ID NO:30).

9. The immunogenic composition of claim 5, wherein said peptide is in an immunogenically effective human dose and said pharmaceutically acceptable carrier is in a human dose.

10. The immunogenic composition of claim 5, wherein said pharmaceutically acceptable carrier comprises a liposome.

11. The immunogenic peptide of claim 1, wherein said peptide is located in a host cell, and is the result of expression of a recombinant nucleic acid molecule that encodes said immunogenic peptide and has been introduced into the host cell.

12. The immunogenic peptide of claim 11, wherein said recombinant nucleic acid molecule that encodes said immunogenic peptide also encodes at least one additional peptide.

13. The immunogenic composition of claim 5, wherein said composition further comprises a second immunogenic peptide.

14. The immunogenic composition of claim 13, wherein said second immunogenic peptide elicits a T-helper cell-mediated immune response.

15. The immunogenic composition of claim 13, wherein said second immunogenic peptide elicits a cytotoxic T lymphocyte response.

16. The immunogenic composition of claim 13, wherein said immunogenic peptide and said second immunogenic peptide are conjugated to form a heteropolymer.

17. The immunogenic composition of claim 5, wherein said peptide is in an immunogenically effective human dose and said pharmaceutically acceptable carrier is in a human dose.

18. The HBV immunogenic peptide of claim 1, further comprising a carrier coupled thereto.

19. The HBV immunogenic peptide of claim 1, further comprising a lipid coupled thereto.

20. A method of stimulating a cytotoxic T cell response, said method comprising administering the peptide of claim 1, or a nucleic acid encoding said peptide, to a subject.

21. A method of stimulating a cytotoxic T cell response, said method comprising administering the peptide of claim 1, or a nucleic acid encoding said peptide, to lymphocytes ex vivo.

22. The method of claim 21, further comprising administering the lymphocytes to a subject.

* * * * *

UNITED STATES PATENT AND TRADEMARK OFFICE
CERTIFICATE OF CORRECTION

PATENT NO. : 7,744,898 B2
APPLICATION NO. : 11/221470
DATED : June 29, 2010
INVENTOR(S) : Francis V. Chisari It is certified that error appears in the above-identified patent and that said Letters Patent is hereby corrected as shown below:

Column 1,
Lines 22-23, "This invention was made with government support under Contract No. AI20001 by the National" should read
--A portion of the work described herein was supported by grant number AI20001 from the National--.
Line 24, "The government has" should read --The United States Government has--.

Column 2,
Line 45 "HBpol-4-13" should read --HBpol4-13--.

Column 12,
Lines 31-32 "HBpol139-147 Tyr-Phe-Gln-Thr-Arg)" should read
--HBpol139-147 (Val-Val-Asn-His-Tyr-Phe-Gln-Thr-Arg)--.

Signed and Sealed this

Sixteenth Day of November, 2010

David J. Kappos
*Director of the United States Patent and Trademark Office*

SEQUENCE LISTING (1) GENERAL INFORMATION:

(iii) NUMBER OF SEQUENCES: 66

(2) INFORMATION FOR SEQ ID NO: 1:

(i) SEQUENCE CHARACTERISTICS:
      (A) LENGTH: 9 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

Gly Leu Tyr Ser Ser Thr Val Pro Val
1               5

(2) INFORMATION FOR SEQ ID NO: 2:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 2:

Gly Leu Ser Arg Tyr Val Ala Arg Leu
1               5

(2) INFORMATION FOR SEQ ID NO: 3:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 3:

Ile Leu Arg Gly Thr Ser Phe Val Tyr Val
1               5                   10

(2) INFORMATION FOR SEQ ID NO: 4:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 4:

Ser Leu Tyr Ala Asp Ser Pro Ser Val
1               5

(2) INFORMATION FOR SEQ ID NO: 5:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 5:

Phe Leu Leu Ser Leu Gly Ile His Leu
1               5

(2) INFORMATION FOR SEQ ID NO: 6:

(i) SEQUENCE CHARACTERISTICS:
            (A) LENGTH: 20 amino acids
            (B) TYPE: amino acid
            (C) STRANDEDNESS: <Unknown>

(D) TOPOLOGY: linear (ii) MOLECULE TYPE: peptide (xi) SEQUENCE DESCRIPTION: SEQ ID NO: 6:

Met Asp Ile Asp Pro Tyr Lys Glu Phe Gly Ala Thr Val Glu Leu Leu
1               5                   10                  15

Ser Phe Leu Pro
            20

(2) INFORMATION FOR SEQ ID NO: 7:

(i) SEQUENCE CHARACTERISTICS:
           (A) LENGTH: 20 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 7:

Pro His His Tyr Ala Leu Arg Gln Ala Ile Leu Cys Trp Gly Glu Leu
1               5                   10                  15

Met Tyr Leu Ala
            20

(2) INFORMATION FOR SEQ ID NO: 8:

(i) SEQUENCE CHARACTERISTICS:
           (A) LENGTH: 20 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 8:

Leu Leu Trp Phe His Ile Ser Cys Leu Thr Phe Gly Arg Glu Thr Val
1               5                   10                  15

Ile Glu Tyr Leu
            20

(2) INFORMATION FOR SEQ ID NO: 9:

(i) SEQUENCE CHARACTERISTICS:
           (A) LENGTH: 15 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 9:

Glu Tyr Leu Val Ser Phe Gly Val Trp Ile Arg Thr Pro Pro Ala
1               5                   10                  15

(2) INFORMATION FOR SEQ ID NO: 10:

(i) SEQUENCE CHARACTERISTICS:
           (A) LENGTH: 20 amino acids
           (B) TYPE: amino acid
           (C) STRANDEDNESS: <Unknown>
           (D) TOPOLOGY: linear (ii) MOLECULE TYPE: peptide (xi) SEQUENCE DESCRIPTION: SEQ ID NO: 10:

```
Val Ser Phe Gly Val Trp Ile Arg Thr Pro Pro Ala Tyr Arg Pro Pro
1               5                   10                  15

Asn Ala Pro Ile
            20

(2) INFORMATION FOR SEQ ID NO: 11:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Modified-site
        (B) LOCATION: 1..845
        (D) OTHER INFORMATION: /product= "OTHER"
            /note= "Xaa = any amino acid
            (<50% consensus)"

(xi) SEQUENCE DESCRIPTION: SEQ ID NO: 11:

Met Pro Leu Ser Tyr Gln His Phe Arg Lys Leu Leu Leu Asp Asp
1               5                   10                  15

Gly Thr Glu Ala Gly Pro Leu Glu Glu Glu Leu Pro Arg Leu Ala Asp
                20                  25                  30

Glu Gly Leu Asn Arg Arg Val Ala Glu Asp Leu Asn Leu Gly Asn Leu
                35                  40                  45

Asn Val Ser Ile Pro Trp Thr His Lys Val Gly Asn Phe Thr Gly Leu
50                  55                  60

Tyr Ser Ser Thr Val Pro Val Phe Asn Pro Glu Trp Gln Thr Pro Ser
65                  70                  75                  80

Phe Pro Xaa Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Asn Xaa Thr Lys Tyr Leu Pro Leu Asp
                115                 120                 125

Lys Gly Ile Lys Pro Tyr Tyr Pro Glu His Xaa Val Asn His Tyr Phe
130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Phe Gln Thr Ser Thr
                180                 185                 190

Arg His Gly Asp Glu Ser Phe Cys Ser Gln Ser Ser Gly Ile Leu Ser
                195                 200                 205

Arg Ser Pro Val Gly Pro Cys Xaa Arg Ser Gln Leu Xaa Gln Ser Arg
                210                 215                 220

Leu Gly Leu Gln Pro Gln Gln Gly Xaa Leu Ala Arg Arg Gln Gln Gly
225                 230                 235                 240

Arg Ser Gly Ser Ile Arg Ala Arg Val His Pro Thr Thr Arg Arg Xaa
                245                 250                 255

Phe Gly Val Glu Pro Ser Gly Ser Gly His Ile Asp Asn Xaa Ala Ser
                260                 265                 270

Ser Ser Ser Ser Cys Leu His Gln Ser Ala Val Arg Lys Ala Ala Tyr
                275                 280                 285
```

```
Ser His Leu Ser Thr Ser Lys Arg Gln Ser Ser Gly His Ala Val
    290                 295                 300

Glu Leu His Asn Xaa Pro Pro Asn Ser Ala Arg Ser Gln Ser Glu Gly
305                 310                 315                 320

Pro Val Phe Ser Cys Trp Trp Leu Gln Phe Arg Asn Ser Lys Pro Cys
                325                 330                 335

Ser Asp Tyr Cys Leu Xaa His Ile Val Asn Leu Leu Glu Asp Trp Gly
            340                 345                 350

Pro Cys Thr Glu His Gly Glu His Xaa Ile Arg Ile Pro Arg Thr Pro
        355                 360                 365

Ala Arg Val Thr Gly Gly Val Phe Leu Val Asp Lys Asn Pro His Asn
    370                 375                 380

Thr Thr Glu Ser Arg Leu Val Asp Phe Gln Phe Ser Arg Gly
385                 390                 395                 400

Xaa Thr Arg Val Ser Trp Pro Lys Phe Ala Val Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
        435                 440                 445

Leu Leu Val Gly Ser Ser Gly Leu Ser Arg Tyr Val Ala Arg Leu Ser
    450                 455                 460

Ser Asn Ser Arg Ile Ile Asn Xaa Gln His Gly Thr Met Gln Asn Leu
465                 470                 475                 480

His Asp Ser Cys Ser Arg Asn Leu Tyr Val Ser Leu Leu Leu Leu Tyr
                485                 490                 495

Lys Thr Phe Gly Arg Lys Leu His Leu Tyr Ser His Pro Ile Ile Leu
            500                 505                 510

Gly Phe Arg Lys Ile Pro Met Gly Val Gly Leu Ser Pro Phe Leu Leu
    515                 520                 525

Ala Gln Phe Thr Ser Ala Ile Cys Ser Val Val Arg Arg Ala Phe Pro
        530                 535                 540

His Cys Leu Ala Phe Ser Tyr Met Asp Asp Val Val Leu Gly Ala Lys
545                 550                 555                 560

Ser Val Gln His Leu Glu Ser Leu Phe Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Ser Trp Gly Thr Leu
    595                 600                 605

Pro Gln Glu His Ile Val Gln Lys Ile Lys Gln Cys Phe Arg Lys Leu
        610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ser Lys Gln Ala Phe Thr Phe Ser
            660                 665                 670

Pro Thr Tyr Lys Ala Phe Leu Cys Lys Gln Tyr Leu Asn Leu Tyr Pro
    675                 680                 685

Val Ala Arg Gln Arg Pro Gly Leu Cys Gln Val Phe Ala Asp Ala Thr
690                 695                 700
```

```
Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
                740                 745                 750

Val Val Leu Ser Arg Lys Tyr Thr Ser Phe Pro Trp Leu Leu Gly Cys
                755                 760                 765

Ala Ala Asn Trp Ile Leu Arg Gly Thr Ser Phe Val Tyr Val Pro Ser
770                 775                 780

Ala Leu Asn Pro Ala Asp Asp Pro Ser Arg Gly Arg Leu Gly Leu Tyr
785                 790                 795                 800

Arg Pro Leu Leu Arg Leu Pro Phe Arg Pro Thr Thr Gly Arg Thr Ser
                805                 810                 815

Leu Tyr Ala Val Ser Pro Ser Val Pro Ser His Leu Pro Asp Arg Val
                820                 825                 830

His Phe Ala Ser Pro Leu His Val Ala Trp Arg Pro Pro
        835                 840                 845
```

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

```
Ser Tyr Gln His Phe Arg Lys Leu Leu Leu
1               5                   10
```

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Arg Leu Lys Leu Ile Met Pro Ala Arg
1               5
```

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Val Val Asn His Tyr Phe Gln Thr Arg
1               5
```

(2) INFORMATION FOR SEQ ID NO: 15:

(i) SEQUENCE CHARACTERISTICS:

(A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

His Thr Leu Trp Lys Ala Gly Ile Leu Tyr
1               5                   10

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Thr Leu Trp Lys Ala Gly Ile Leu Tyr Lys
1               5                   10

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Leu Tyr Ser His Pro Ile Ile Leu Gly Phe
1               5                   10

(2) INFORMATION FOR SEQ ID NO: 18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Tyr Met Asp Asp Val Val Leu Gly Ala
1               5

(2) INFORMATION FOR SEQ ID NO: 19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Phe Leu Leu Ser Leu Gly Ile His Leu
1               5

(2) INFORMATION FOR SEQ ID NO: 20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Ala Leu Met Pro Leu Tyr Ala Cys Ile
1               5

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Gly Thr Asp Asn Ser Val Val Leu Ser Arg
1               5                   10

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Lys Tyr Thr Ser Phe Pro Trp Leu Leu
1               5

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Trp Ile Leu Arg Gly Thr Ser Phe Arg
1               5

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Asp Leu Asn Leu Gly Asn Leu Asn Val
1               5

(2) INFORMATION FOR SEQ ID NO: 25:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 25:

Phe Leu Pro Ser Asp Tyr Phe Pro Ser Val
1               5                   10

(2) INFORMATION FOR SEQ ID NO: 26:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 26:

Leu Leu Ala Gln Phe Thr Ser Ala Ile
1               5

(2) INFORMATION FOR SEQ ID NO: 27:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 27:

Lys Leu His Leu Tyr Ser His Pro Ile
1               5

(2) INFORMATION FOR SEQ ID NO: 28:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 28:

Ala Leu Met Pro Leu Tyr Ala Cys Ile
1               5

(2) INFORMATION FOR SEQ ID NO: 29:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 29:

His Leu Tyr Ser His Pro Ile Ile Leu
1               5

```
(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Phe Leu Leu Ala Gln Phe Thr Ser Ala Ile
1               5                   10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Tyr Leu His Thr Leu Trp Lys Ala Gly Ile
1               5                   10

(2) INFORMATION FOR SEQ ID NO: 32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Trp Ile Leu Arg Gly Thr Ser Phe Val
1               5

(2) INFORMATION FOR SEQ ID NO: 33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Leu Leu Gly Cys Ala Ala Asn Trp Ile Leu
1               5                   10

(2) INFORMATION FOR SEQ ID NO: 34:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Asn Leu Ser Trp Leu Ser Leu Asp Val
1               5
```

(2) INFORMATION FOR SEQ ID NO: 35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Phe Leu Pro Ser Asp Phe Pro Pro Ser Val
1               5                   10
```

(2) INFORMATION FOR SEQ ID NO: 36:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Trp Leu Ser Leu Leu Val Pro Phe Val
1               5
```

(2) INFORMATION FOR SEQ ID NO: 37:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Lys Leu Val Ala Leu Gly Ile Asn Ala Val
1               5                   10
```

(2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Gly Leu Pro Arg Tyr Val Ala Arg Leu
1               5
```

(2) INFORMATION FOR SEQ ID NO: 39:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Ser Gly Leu Ser Arg Tyr Val Ala Arg Leu
1               5                   10
```

```
(2) INFORMATION FOR SEQ ID NO: 40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Gly Leu Ser Arg Tyr Val Ala Arg Leu Ser
1               5                   10

(2) INFORMATION FOR SEQ ID NO: 41:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Gly Val Ser Arg Tyr Val Ala Arg Leu
1               5

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Gly Leu Pro Arg Tyr Val Ala Arg Leu
1               5

(2) INFORMATION FOR SEQ ID NO: 43:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Gly Leu Pro Arg Tyr Val Val Cys Leu
1               5

(2) INFORMATION FOR SEQ ID NO: 44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

Gly Leu Ser Arg Tyr Val Val Cys Leu
```

-continued

```
1               5
```

(2) INFORMATION FOR SEQ ID NO: 45:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 45:

```
Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Met Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Thr
            260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Gly His Ala Val Glu Phe
    290                 295                 300

His Asn Ile Pro Pro Ser Ser Ala Arg Ser Gln Ser Glu Gly Pro Ile
305                 310                 315                 320

Phe Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
```

-continued

```
                340                 345                 350
Thr Glu His Gly Glu His Asn Ile Arg Ile Pro Arg Thr Pro Ala Arg
            355                 360                 365
Val Thr Gly Gly Val Phe Leu Val Asp Lys Asn Pro His Asn Thr Thr
        370                 375                 380
Glu Ser Arg Leu Val Val Asp Phe Ser Gln Phe Ser Arg Gly Ser Thr
385                 390                 395                 400
His Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
            420                 425                 430
Ala Phe Tyr His Ile Pro Leu His Pro Ala Ala Met Pro His Leu Leu
        435                 440                 445
Val Gly Ser Ser Gly Leu Pro Arg Tyr Val Ala Arg Leu Ser Ser Thr
    450                 455                 460
Ser Arg Asn Ile Asn His Gln His Gly Ala Met Gln Asp Leu His Asp
465                 470                 475                 480
Ser Cys Ser Arg Asn Leu Tyr Val Ser Leu Leu Leu Leu Tyr Lys Thr
                485                 490                 495
Phe Gly Arg Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
    530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
                565                 570                 575
Leu Gly Ile His Leu Asn Pro Asn Lys Thr Lys Arg Trp Gly Tyr Ser
            580                 585                 590
Leu Asn Phe Met Gly Tyr Val Ile Gly Ser Trp Gly Thr Leu Pro Gln
        595                 600                 605
Glu His Ile Val Leu Lys Leu Lys Gln Cys Phe Arg Lys Leu Pro Val
    610                 615                 620
Asn Ser Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
            660                 665                 670
Tyr Lys Ala Phe Leu Cys Lys Gln Tyr Leu Asn Leu Tyr Pro Val Ala
        675                 680                 685
Arg Gln Arg Ser Gly Leu Cys Gln Val Phe Ala Asp Ala Thr Pro Thr
    690                 695                 700
Gly Trp Gly Leu Ala Ile Gly His Arg Arg Met Arg Gly Thr Phe Val
705                 710                 715                 720
Ala Pro Leu Pro Ile His Thr Ala Glu Leu Leu Ala Ala Cys Phe Ala
                725                 730                 735
Arg Ser Arg Ser Gly Ala Lys Leu Ile Gly Thr Asp Asn Ser Val Val
            740                 745                 750
Leu Ser Arg Lys Tyr Thr Ser Phe Pro Trp Leu Leu Gly Cys Ala Ala
        755                 760                 765
```

```
Asn Trp Ile Leu Arg Gly Thr Ser Phe Val Tyr Val Pro Ser Ala Leu
            770                 775                 780

Asn Pro Ala Asp Asp Pro Ser Arg Gly Arg Leu Gly Leu Tyr Arg Pro
785                 790                 795                 800

Leu Leu Leu Leu Pro Phe Arg Pro Thr Thr Gly Arg Thr Ser Leu Tyr
                805                 810                 815

Ala Val Ser Pro Ser Val Pro Ser His Leu Pro Asp Arg Val His Phe
                820                 825                 830

Ala Ser Pro Leu His Val Ala Trp Arg Pro Pro
            835                 840
```

(2) INFORMATION FOR SEQ ID NO: 46:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Modified-site
        (B) LOCATION: 16..18
        (D) OTHER INFORMATION: /product= "OTHER"
            /note= "Xaa = unknown"

(xi) SEQUENCE DESCRIPTION: SEQ ID NO: 46:

```
Met Pro Leu Ser Tyr Gln His Phe Arg Lys Leu Leu Leu Leu Asp Xaa
1               5                   10                  15

Xaa Xaa Glu Ala Gly Pro Leu Glu Glu Glu Leu Pro Arg Leu Ala Asp
            20                  25                  30

Glu Gly Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro His Ile His Leu Gln Glu Asp Ile Ile Asn Arg Cys Gln Gln
                85                  90                  95

Tyr Val Gly Pro Leu Thr Val Asn Glu Lys Arg Arg Leu Lys Leu Ile
                100                 105                 110

Met Pro Ala Arg Phe Tyr Pro Asn Leu Thr Lys Tyr Leu Pro Leu Asp
            115                 120                 125

Lys Gly Ile Lys Pro Tyr Tyr Pro Glu His Ala Val Asn His Tyr Phe
130                 135                 140

Lys Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Phe Gln Thr Ser Thr
            180                 185                 190

Arg His Gly Asp Glu Ser Phe Cys Ser Gln Ser Ser Gly Ile Leu Ser
        195                 200                 205

Arg Ser Pro Val Gly Pro Cys Val Arg Ser Gln Leu Lys Gln Ser Arg
    210                 215                 220

Leu Gly Leu Gln Pro Gln Gln Gly Ser Leu Ala Arg Gly Lys Ser Gly
225                 230                 235                 240
```

-continued

```
Arg Ser Gly Ser Ile Arg Ala Arg Val His Pro Thr Thr Arg Arg Ser
                245                 250                 255

Phe Gly Val Glu Pro Ser Gly Ser Gly His Ile Asp Asn Ser Ala Ser
            260                 265                 270

Ser Thr Ser Ser Cys Leu His Gln Ser Ala Val Arg Lys Thr Ala Tyr
        275                 280                 285

Ser His Leu Ser Thr Ser Lys Arg Gln Ser Ser Gly His Ala Val
    290                 295                 300

Glu Leu His Asn Ile Pro Pro Ser Ser Ala Arg Pro Gln Ser Glu Gly
305                 310                 315                 320

Pro Ile Leu Ser Cys Trp Trp Leu Gln Phe Arg Asn Ser Lys Pro Cys
                325                 330                 335

Ser Asp Tyr Cys Leu Thr His Ile Val Asn Leu Leu Glu Asp Trp Gly
            340                 345                 350

Pro Cys Thr Glu His Gly Glu His Asn Ile Arg Ile Pro Arg Thr Pro
        355                 360                 365

Ala Arg Val Thr Gly Gly Val Phe Leu Val Asp Lys Asn Pro His Asn
    370                 375                 380

Thr Thr Glu Ser Thr Leu Val Val Asp Phe Ser Gln Phe Ser Arg Gly
385                 390                 395                 400

Ser Thr His Val Ser Trp Pro Lys Phe Ala Val Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
        435                 440                 445

Leu Leu Val Gly Ser Ser Gly Leu Pro Arg Tyr Val Val Cys Leu Ser
    450                 455                 460

Ser Thr Ser Lys Asn Ile Asn Tyr Gln His Gly Thr Met Gln Asp Leu
465                 470                 475                 480

His Asp Ser Cys Ser Arg Asn Leu Tyr Val Ser Leu Phe Leu Leu Tyr
                485                 490                 495

Lys Thr Phe Gly Arg Lys Leu His Leu Tyr Ser His Pro Ile Ile Leu
            500                 505                 510

Gly Phe Arg Lys Ile Pro Met Gly Val Gly Leu Ser Pro Phe Leu Leu
        515                 520                 525

Ala Gln Phe Thr Ser Ala Ile Cys Ser Val Val Arg Arg Ala Phe Pro
    530                 535                 540

His Cys Leu Ala Phe Ser Tyr Met Asp Asp Val Val Leu Gly Ala Lys
545                 550                 555                 560

Ser Val Gln His Leu Glu Ser Leu Phe Thr Ser Ile Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Cys Trp Gly Thr Leu
        595                 600                 605

Pro Gln Glu His Ile Val Leu Lys Ile Lys Gln Cys Phe Arg Lys Leu
    610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655
```

```
Met Pro Leu Tyr Ala Cys Ile Gln Ser Lys Gln Ala Phe Thr Phe Ser
            660                 665                 670

Pro Thr Tyr Lys Ala Phe Leu Cys Lys Gln Tyr Leu Asn Leu Tyr Pro
            675                 680                 685

Val Ala Arg Gln Arg Ser Gly Leu Cys Gln Val Phe Ala Asp Ala Thr
            690                 695                 700

Pro Thr Gly Trp Gly Leu Ala Ile Gly His Arg Met Arg Gly Thr
705                 710                 715                 720

Phe Val Ala Pro Leu Pro Ile His Thr Ala Glu Leu Leu Ala Ala Cys
                    725                 730                 735

Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
            755                 760                 765

Ala Ala Asn Trp Ile Leu Arg Gly Thr Ser Phe Val Tyr Val Pro Ser
            770                 775                 780

Ala Leu Asn Pro Ala Asp Asp Pro Ser Arg Gly Arg Leu Gly Leu Tyr
785                 790                 795                 800

Arg Pro Leu Leu His Leu Pro Phe Arg Pro Thr Thr Gly Arg Thr Ser
                    805                 810                 815

Leu Tyr Ala Val Ser Pro Ser Val Pro Ser His Leu Pro Asp Arg Val
            820                 825                 830

His Phe Pro Ser Pro Leu His Val Ala Trp Arg Pro Pro
            835                 840                 845

(2) INFORMATION FOR SEQ ID NO: 47:

(i) SEQUENCE CHARACTERISTICS:
          (A) LENGTH: 843 amino acids
          (B) TYPE: amino acid
          (C) STRANDEDNESS: <Unknown>
          (D) TOPOLOGY: linear (ii) MOLECULE TYPE: protein (xi) SEQUENCE DESCRIPTION: SEQ ID NO: 47:

Met Pro Leu Ser Tyr Gln His Phe Arg Lys Leu Leu Leu Leu Asp Asp
1                   5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Val Leu Asn Pro Glu Ser Gln Thr Pro Ser Phe Pro
65                  70                  75                  80

Asn Ile His Leu Gln Glu Asp Ile Ile Asn Arg Cys Gln Gln Tyr Val
                    85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
            115                 120                 125

Ile Lys Pro Tyr Tyr Pro Glu His Ala Val Asn His Tyr Phe Lys Thr
            130                 135                 140

Arg His Tyr Leu His Thr Leu Trp Lys Ala Gly Ile Leu Tyr Lys Arg
145                 150                 155                 160
```

```
Glu Thr Thr Arg Ser Ala Ser Phe Cys Gly Ser Pro Tyr Ser Trp Glu
                165                 170                 175

Gln Glu Leu Arg His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Asn Gln Gly Arg Ser
225                 230                 235                 240

Gly Arg Leu Arg Ala Arg Val His Pro Thr Thr Arg Arg Ser Phe Gly
                245                 250                 255

Val Glu Pro Ser Gly Ser Gly His Ile Asp Asn Ser Ala Ser Ser Ala
            260                 265                 270

Ser Ser Cys Phe His Gln Ser Ala Val Arg Lys Thr Ala Tyr Ser His
        275                 280                 285

Leu Ser Thr Ser Lys Arg Gln Ser Ser Ser Gly His Ala Val Glu Leu
    290                 295                 300

His Asn Ile Pro Pro Ser Ser Ala Arg Ser Gln Ser Glu Gly Pro Ile
305                 310                 315                 320

Phe Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
        435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asp Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
```

-continued

```
                580                 585                 590
Leu Asn Phe Met Gly Tyr Val Ile Gly Ser Trp Gly Thr Leu Pro Gln
            595                 600                 605
Glu His Ile Val Leu Lys Leu Lys Gln Cys Phe Arg Lys Leu Pro Val
        610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
            660                 665                 670
Tyr Lys Ala Phe Leu Cys Gln Gln Tyr Leu His Leu Tyr Pro Val Ala
        675                 680                 685
Arg Gln Arg Ser Gly Leu Cys Gln Val Phe Ala Asp Ala Thr Pro Thr
690                 695                 700
Gly Trp Gly Leu Ala Ile Gly His Arg Arg Met Arg Gly Thr Phe Val
705                 710                 715                 720
Val Pro Leu Pro Ile His Thr Ala Glu Leu Leu Ala Ala Cys Phe Ala
                725                 730                 735
Arg Asp Arg Ser Gly Ala Lys Leu Ile Gly Thr Asp Asn Ser Val Val
            740                 745                 750
Leu Ser Arg Lys Tyr Thr Ser Phe Pro Trp Leu Leu Gly Cys Ala Ala
        755                 760                 765
Asn Trp Ile Leu Arg Gly Thr Ser Phe Val Tyr Val Pro Ser Ala Leu
770                 775                 780
Asn Pro Ala Asp Asp Pro Ser Arg Gly Arg Leu Gly Leu Tyr Arg Pro
785                 790                 795                 800
Leu Leu Ser Leu Pro Phe Gln Pro Thr Thr Gly Arg Thr Ser Leu Tyr
                805                 810                 815
Ala Val Ser Pro Ser Val Pro Ser His Leu Pro Asp Arg Val His Phe
            820                 825                 830
Ala Ser Pro Leu His Val Ala Trp Arg Pro Pro
        835                 840
```

(2) INFORMATION FOR SEQ ID NO: 48:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 48:

```
Met Pro Leu Ser Tyr Gln His Phe Arg Lys Leu Leu Leu Leu Asp Asp
1               5                   10                  15
Glu Ala Gly Pro Leu Glu Glu Glu Leu Pro Arg Leu Ala Asp Glu Gly
            20                  25                  30
Leu Asn Arg Arg Val Ala Glu Asp Leu Asn Leu Gly Asn Leu Asn Val
        35                  40                  45
Ser Ile Pro Trp Thr His Lys Val Gly Asn Phe Thr Gly Leu Tyr Ser
    50                  55                  60
Ser Thr Val Pro Val Phe Asn Pro Glu Trp Gln Thr Pro Ser Phe Pro
65                  70                  75                  80
Asn Ile His Leu Gln Glu Asp Ile Ile Asn Arg Cys Gln Gln Tyr Val
```

```
                85                  90                  95
Gly Pro Leu Thr Val Asn Glu Lys Arg Leu Lys Leu Ile Met Pro
            100                 105                 110

Ala Arg Phe Tyr Pro Asn Leu Thr Lys Tyr Leu Pro Leu Asp Lys Gly
            115                 120                 125

Ile Lys Pro Tyr Tyr Pro Glu His Ala Val Asn His Tyr Phe Lys Thr
            130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
            195                 200                 205

Pro Val Gly Pro Cys Ile Arg Ser Gln Leu Lys Gln Ser Arg Leu Gly
            210                 215                 220

Leu Gln Pro Gln Gln Gly Ser Leu Ala Arg Gly Lys Ser Gly Arg Ser
225                 230                 235                 240

Gly Ser Ile Trp Ala Arg Val His Pro Thr Thr Arg Arg Ser Phe Gly
                245                 250                 255

Val Glu Pro Ser Gly Ser Gly His Ile Asp Asn Ser Ala Ser Ser Ala
            260                 265                 270

Ser Ser Cys Leu Tyr Gln Ser Ala Val Arg Lys Thr Ala Tyr Ser His
            275                 280                 285

Leu Ser Thr Ser Lys Arg Gln Ser Ser Gly His Ala Val Glu Leu
            290                 295                 300

His Asn Ile Pro Pro Ser Cys Ala Arg Ser Gln Ser Glu Gly Pro Ile
305                 310                 315                 320

Ser Ser Cys Trp Trp Leu Gln Phe Arg Asn Ser Glu Pro Cys Ser Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
            355                 360                 365

Val Thr Gly Gly Val Phe Leu Val Asp Lys Asn Pro His Asn Thr Thr
370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
            450                 455                 460

Ser Arg Asn Ile Asn Tyr Gln His Gly Thr Met Gln Asp Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510
```

```
Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
        530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro His Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Leu Lys Ile Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670

Tyr Lys Ala Phe Leu Cys Lys Gln Tyr Leu His Leu Tyr Pro Val Ala
        675                 680                 685

Arg Gln Arg Ser Gly Leu Cys Gln Val Phe Ala Asp Ala Thr Pro Thr
    690                 695                 700

Gly Trp Gly Leu Ala Ile Gly Gln Ser Gly Met Arg Gly Thr Phe Val
705                 710                 715                 720

Ala Pro Leu Pro Ile His Thr Ala Glu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu His Leu Pro Phe Arg Pro Thr Thr Gly Arg Ala Ser Leu Tyr
                805                 810                 815

Ala Val Ser Pro Ser Val Pro Ser His Leu Pro Val Arg Val His Phe
            820                 825                 830

Ala Ser Pro Leu His Val Ala Trp Arg Pro Pro
        835                 840

(2) INFORMATION FOR SEQ ID NO: 49:

(i) SEQUENCE CHARACTERISTICS:
        (A) LENGTH: 730 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 49:

Met Pro Leu Ser Tyr Gln His Phe Arg Lys Leu Leu Leu Leu Asp Asp
1               5                   10                  15
```

-continued

Glu Ala Gly Pro Leu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
                100                 105                 110

Ala Arg Phe Tyr Pro Asn Leu Thr Lys Tyr Leu Pro Leu Asp Lys Gly
            115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
                180                 185                 190

Gly Asp Glu Ser Phe Cys Ser Gln Ser Ser Gly Ile Leu Ser Arg Ser
            195                 200                 205

Pro Val Gly Pro Cys Val Arg Ser Gln Leu Thr Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ala Gly Ser Gly Arg Ile Asp Asn Arg Ala Ser Ser Thr
                260                 265                 270

Ser Ser Cys Leu His Gln Ser Ala Val Arg Lys Thr Ala Tyr Ser His
            275                 280                 285

Leu Ser Thr Ser Lys Arg Gln Ser Ser Ser Gly His Ala Val Glu Leu
    290                 295                 300

His Asn Ile Pro Pro Ser Ser Ala Arg Pro Gln Ser Glu Gly Pro Ile
305                 310                 315                 320

Leu Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
                340                 345                 350

Thr Glu His Gly Glu His Asn Ile Arg Ile Pro Arg Thr Pro Ala Arg
            355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
                420                 425                 430

```
Ala Phe Tyr His Ile Pro Leu His Pro Ala Ala Met Pro His Leu Leu
        435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asp Leu His Asp
465                 470                 475                 480

Ser Cys Ser Arg Asn Leu Tyr Val Ser Leu Leu Leu Tyr Lys Thr
            485                 490                 495

Phe Gly Arg Lys Leu His Leu Tyr Ser His Pro Ile Ile Leu Gly Phe
                500                 505                 510

Arg Lys Ile Pro Met Gly Gly Leu Ser Pro Phe Leu Leu Ala Gln
    515                 520                 525

Phe Thr Ser Ala Ile Cys Ser Val Val Arg Arg Ala Phe Pro His Cys
    530                 535                 540

Leu Ala Phe Ser Tyr Met Asp Asp Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
                580                 585                 590

Leu Asn Phe Met Gly Tyr Val Ile Gly Cys Trp Gly Thr Leu Pro Gln
            595                 600                 605

Glu His Ile Val Leu Lys Ile Lys Gln Cys Phe Arg Lys Leu Pro Val
                610                 615                 620

Asn Arg Pro Ile Asp Trp Lys Val Cys Gln Arg Leu Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
                660                 665                 670

Tyr Lys Ala Phe Leu Cys Lys Gln Tyr Leu Asn Leu Tyr Pro Val Ala
        675                 680                 685

Arg Gln Arg Ser Gly Leu Cys Gln Val Phe Ala Asp Ala Thr Pro Thr
            690                 695                 700

Gly Trp Gly Leu Ala Ile Gly His Ser Arg Met Arg Gly Pro Leu Trp
705                 710                 715                 720

Leu Leu Cys Arg Ser Ile Leu Arg Asn Ser
                725                 730

(2) INFORMATION FOR SEQ ID NO: 50:

(i) SEQUENCE CHARACTERISTICS:
        (A) LENGTH: 842 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 50:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Asp
                20                  25                  30

Leu Asn Arg Arg Val Ala Glu Asp Leu Asn Leu Gly Asn Leu Asn Val
            35                  40                  45
```

-continued

```
Ser Ile Pro Trp Thr His Lys Val Gly Asn Phe Thr Gly Leu Tyr Ser
 50                  55                  60

Ser Thr Val Pro Val Phe Asn Pro Glu Trp Gln Thr Pro Ser Phe Pro
 65                  70                  75                  80

His Ile His Leu Gln Glu Asp Ile Ile Asn Arg Cys Gln Gln Tyr Val
                 85                  90                  95

Gly Pro Leu Thr Val Asn Glu Lys Arg Arg Leu Lys Leu Ile Met Pro
            100                 105                 110

Ala Arg Phe Tyr Pro Lys Leu Thr Lys Tyr Leu Pro Leu Asp Lys Gly
        115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val Pro Pro Thr Thr Arg Arg Ser Phe Gly
                245                 250                 255

Val Glu Pro Ser Gly Ser Gly His Ile Asp Asn Arg Ala Ser Ser Thr
            260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Gly His Ala Val Glu Leu
    290                 295                 300

His His Ile Ser Pro Ser Pro Ala Arg Ser Gln Ser Glu Gly Pro Ile
305                 310                 315                 320

Phe Ser Ser Trp Trp Leu Gln Phe Arg Asn Ser Lys Pro Cys Cys Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
        435                 440                 445

Val Gly Ser Ser Gly Leu Pro Arg Tyr Val Ala Arg Leu Ser Ser Thr
    450                 455                 460

Ser Arg Asn Ile Asn His Gln His Gly Thr Met Gln Asp Leu His Asp
```

```
                465                 470                 475                 480
Ser Cys Ser Arg Asn Leu Tyr Val Ser Leu Leu Leu Tyr Lys Thr
                    485                 490                 495
Phe Gly Arg Lys Leu His Leu Tyr Ser His Pro Ile Ile Leu Gly Phe
                500                 505                 510
Arg Lys Ile Pro Met Gly Gly Leu Ser Pro Phe Leu Leu Ala Gln
            515                 520                 525
Phe Thr Ser Ala Ile Cys Ser Val Arg Arg Ala Phe Pro His Cys
        530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
                565                 570                 575
Leu Gly Ile His Leu Asn Pro Asn Lys Thr Lys Arg Trp Gly Tyr Ser
                580                 585                 590
Leu Asn Phe Met Gly Tyr Val Ile Gly Ser Trp Gly Thr Leu Pro Gln
                595                 600                 605
Glu His Ile Val Leu Lys Ile Lys Gln Cys Phe Arg Lys Leu Pro Val
            610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
                660                 665                 670
Tyr Lys Ala Phe Leu Cys Lys Gln Tyr Leu His Leu Tyr Pro Val Ala
            675                 680                 685
Arg Arg Thr Ala Leu Cys Gln Val Phe Ala Asp Ala Thr Pro Thr Gly
        690                 695                 700
Trp Gly Leu Ala Ile Gly His Arg Arg Met Arg Gly Thr Phe Val Ala
705                 710                 715                 720
Pro Leu Pro Ile His Thr Ala Glu Leu Leu Ala Ala Cys Phe Ala Arg
                725                 730                 735
Ser Arg Ser Gly Ala Lys Leu Ile Gly Thr Asp Asn Ser Val Val Leu
                740                 745                 750
Ser Arg Lys Tyr Thr Ser Phe Pro Trp Leu Leu Gly Cys Ala Ala Asn
            755                 760                 765
Trp Ile Leu Arg Gly Thr Tyr Phe Val Tyr Val Pro Ser Ala Leu Asn
            770                 775                 780
Pro Ala Asp Asp Pro Ser Arg Gly Arg Leu Gly Leu Ile Arg Pro Leu
785                 790                 795                 800
Leu His Leu Arg Phe Arg Pro Thr Thr Gly Arg Thr Ser Leu Tyr Ala
                805                 810                 815
Val Ser Pro Ser Val Pro Ser His Leu Pro Asp Arg Val His Phe Ala
                820                 825                 830
Ser Pro Leu His Val Ala Trp Arg Pro Pro
                835                 840

(2) INFORMATION FOR SEQ ID NO: 51:

(i) SEQUENCE CHARACTERISTICS:
        (A) LENGTH: 842 amino acids
        (B) TYPE: amino acid
        (C) STRANDEDNESS: <Unknown>
        (D) TOPOLOGY: linear
```

(ii) MOLECULE TYPE: protein (xi) SEQUENCE DESCRIPTION: SEQ ID NO: 51:

| | | | | | | | | | | | | | | | |
|---|---|---|---|---|---|---|---|---|---|---|---|---|---|---|---|
| Met | Pro | Leu | Ser | Tyr | Gln | His | Phe | Arg | Lys | Leu | Leu | Leu | Asp | Asp |
| 1 | | | | 5 | | | | | 10 | | | | | 15 |
| Glu | Ala | Gly | Pro | Leu | Glu | Glu | Leu | Pro | Arg | Leu | Ala | Asp | Glu | Asp |
| | | | 20 | | | | | 25 | | | | | 30 | |
| Leu | Asn | Arg | Arg | Val | Ala | Glu | Asp | Leu | Asn | Leu | Gly | Asn | Leu | Asn | Val |
| | | 35 | | | | | 40 | | | | | 45 | | | |
| Ser | Ile | Pro | Trp | Thr | His | Lys | Val | Gly | Asn | Phe | Thr | Gly | Leu | Tyr | Ser |
| | 50 | | | | | 55 | | | | | 60 | | | | |
| Ser | Thr | Val | Pro | Val | Phe | Asn | Pro | Glu | Trp | Gln | Thr | Pro | Ser | Phe | Pro |
| 65 | | | | | 70 | | | | | 75 | | | | | 80 |
| His | Ile | His | Leu | Gln | Glu | Asp | Ile | Ile | Asn | Arg | Cys | Gln | Gln | Tyr | Val |
| | | | | 85 | | | | | 90 | | | | | 95 | |
| Gly | Pro | Leu | Thr | Val | Asn | Glu | Lys | Arg | Arg | Leu | Lys | Leu | Ile | Met | Pro |
| | | | 100 | | | | | 105 | | | | | 110 | | |
| Ala | Arg | Phe | Tyr | Pro | Lys | Leu | Thr | Lys | Tyr | Leu | Pro | Leu | Asp | Lys | Gly |
| | | 115 | | | | | 120 | | | | | 125 | | | |
| Ile | Lys | Pro | Tyr | Tyr | Pro | Glu | His | Ala | Val | Asn | His | Tyr | Phe | Lys | Thr |
| | 130 | | | | | 135 | | | | | 140 | | | | |
| Arg | His | Tyr | Leu | His | Thr | Leu | Trp | Lys | Ala | Gly | Ile | Leu | Tyr | Lys | Arg |
| 145 | | | | | 150 | | | | | 155 | | | | | 160 |
| Glu | Thr | Thr | Arg | Ser | Ala | Ser | Phe | Cys | Gly | Ser | Pro | Tyr | Ser | Trp | Glu |
| | | | | 165 | | | | | 170 | | | | | 175 | |
| Gln | Glu | Leu | Gln | His | Gly | Arg | Leu | Val | Phe | Gln | Thr | Ser | Thr | Arg | His |
| | | | 180 | | | | | 185 | | | | | 190 | | |
| Gly | Asp | Glu | Ser | Phe | Cys | Ser | Gln | Ser | Ser | Gly | Ile | Leu | Ser | Arg | Ser |
| | | 195 | | | | | 200 | | | | | 205 | | | |
| Pro | Val | Gly | Pro | Cys | Val | Arg | Ser | Gln | Leu | Lys | Gln | Ser | Arg | Leu | Gly |
| | 210 | | | | | 215 | | | | | 220 | | | | |
| Leu | Gln | Pro | Gln | Gln | Gly | Ser | Leu | Ala | Arg | Gly | Lys | Ser | Gly | Arg | Ser |
| 225 | | | | | 230 | | | | | 235 | | | | | 240 |
| Gly | Ser | Ile | Arg | Ala | Arg | Val | Pro | Pro | Thr | Thr | Arg | Arg | Ser | Phe | Gly |
| | | | | 245 | | | | | 250 | | | | | 255 | |
| Val | Glu | Pro | Ser | Gly | Ser | Gly | His | Ile | Asp | Asn | Arg | Ala | Ser | Ser | Thr |
| | | | 260 | | | | | 265 | | | | | 270 | | |
| Ser | Ser | Cys | Leu | His | Gln | Ser | Ala | Val | Arg | Lys | Thr | Ala | Tyr | Ser | His |
| | | 275 | | | | | 280 | | | | | 285 | | | |
| Leu | Ser | Thr | Ser | Lys | Arg | Gln | Ser | Ser | Gly | His | Ala | Val | Glu | Leu |
| | 290 | | | | | 295 | | | | | 300 | | | | |
| His | His | Ile | Ser | Pro | Ser | Pro | Ala | Arg | Ser | Gln | Ser | Glu | Gly | Pro | Ile |
| 305 | | | | | 310 | | | | | 315 | | | | | 320 |
| Phe | Ser | Ser | Trp | Trp | Leu | Gln | Phe | Arg | Asn | Ser | Lys | Pro | Cys | Ser | Asp |
| | | | | 325 | | | | | 330 | | | | | 335 | |
| Tyr | Cys | Leu | Thr | His | Ile | Val | Asn | Leu | Leu | Glu | Asp | Trp | Gly | Pro | Cys |
| | | | 340 | | | | | 345 | | | | | 350 | | |
| Thr | Glu | His | Gly | Glu | His | Asn | Ile | Arg | Ile | Pro | Arg | Thr | Pro | Ala | Arg |
| | | 355 | | | | | 360 | | | | | 365 | | | |
| Val | Thr | Gly | Gly | Val | Phe | Leu | Val | Asp | Lys | Asn | Pro | His | Asn | Thr | Thr |
| | 370 | | | | | 375 | | | | | 380 | | | | |
| Glu | Ser | Arg | Leu | Val | Val | Asp | Phe | Ser | Gln | Phe | Ser | Arg | Gly | Ser | Thr |
| 385 | | | | | 390 | | | | | 395 | | | | | 400 |

```
His Val Ser Trp Pro Lys Phe Ala Val Pro Asn Leu Gln Ser Leu Thr
            405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
            450                 455                 460

Ser Arg Asn Ile Asn His Gln His Gly Thr Met Gln Asp Leu His Asp
465                 470                 475                 480

Ser Cys Ser Arg Asn Leu Tyr Val Ser Leu Leu Leu Tyr Lys Thr
                    485                 490                 495

Phe Gly Arg Lys Leu His Leu Tyr Ser His Pro Ile Ile Leu Gly Phe
                500                 505                 510

Arg Lys Ile Pro Met Gly Gly Gly Leu Ser Pro Phe Leu Leu Ala Gln
                515                 520                 525

Phe Thr Ser Ala Ile Cys Ser Val Val Arg Arg Ala Phe Pro His Cys
            530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
                565                 570                 575

Leu Gly Ile His Leu Asn Pro Asn Lys Thr Lys Arg Trp Gly Tyr Ser
                580                 585                 590

Leu Asn Phe Met Gly Tyr Val Ile Gly Ser Trp Gly Thr Leu Pro Gln
                595                 600                 605

Glu His Ile Val Leu Lys Ile Lys Gln Cys Phe Arg Lys Leu Pro Val
            610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
                660                 665                 670

Tyr Lys Ala Phe Leu Cys Lys Gln Tyr Leu His Leu Tyr Pro Val Ala
                675                 680                 685

Arg Arg Thr Ala Leu Cys Gln Val Phe Ala Asp Ala Thr Pro Thr Gly
            690                 695                 700

Trp Gly Leu Ala Ile Gly His Arg Arg Met Arg Gly Thr Phe Val Ala
705                 710                 715                 720

Pro Leu Pro Ile His Thr Ala Glu Leu Leu Ala Ala Cys Phe Ala Arg
                725                 730                 735

Ser Arg Ser Gly Ala Lys Leu Ile Gly Thr Asp Asn Ser Val Val Leu
                740                 745                 750

Ser Arg Lys Tyr Thr Ser Phe Pro Trp Leu Leu Gly Cys Ala Ala Asn
                755                 760                 765

Trp Ile Leu Arg Gly Thr Tyr Phe Val Tyr Val Pro Ser Ala Leu Asn
            770                 775                 780

Pro Ala Asp Asp Pro Ser Arg Gly Arg Leu Gly Leu Ile Arg Pro Leu
785                 790                 795                 800

Leu His Leu Arg Phe Arg Pro Thr Thr Gly Arg Thr Ser Leu Tyr Ala
                805                 810                 815
```

```
Val Ser Pro Ser Val Pro Ser His Leu Pro Asp Arg Val His Phe Ala
            820                 825                 830

Ser Pro Leu His Val Ala Trp Arg Pro Pro
            835                 840
```

(2) INFORMATION FOR SEQ ID NO: 52:

(i) SEQUENCE CHARACTERISTICS:
        (A) LENGTH: 481 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 52:

```
Met Pro Leu Ser Tyr Gln His Phe Arg Lys Leu Leu Leu Asp Asp
1               5                   10                  15

Gly Thr Glu Ala Gly Pro Leu Glu Glu Glu Leu Pro Arg Leu Ala Asp
            20                  25                  30

Ala Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
            85                  90                  95

Phe Val Gly Pro Leu Thr Val Asn Glu Lys Arg Arg Leu Lys Leu Ile
            100                 105                 110

Met Pro Ala Arg Phe Tyr Pro Thr His Thr Lys Tyr Leu Pro Leu Asp
            115                 120                 125

Lys Gly Ile Lys Pro Tyr Tyr Pro Asp Gln Val Val Asn His Tyr Phe
            130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Ser Gln Arg His Gly Asp Glu Ser Phe
            180                 185                 190

Cys Ser Gln Ser Ser Gly Ile Pro Ser Arg Ser Ser Val Gly Pro Cys
            195                 200                 205

Ile Arg Ser Gln Leu Asn Lys Ser Arg Leu Gly Leu Gln Pro His Gln
            210                 215                 220

Gly Pro Leu Ala Ser Ser Gln Pro Gly Arg Ser Gly Ser Ile Arg Ala
225                 230                 235                 240

Arg Ala His Pro Ser Thr Arg Arg Tyr Phe Gly Val Glu Pro Ser Gly
                245                 250                 255

Ser Gly His Ile Asp His Ser Val Asn Asn Ser Ser Ser Cys Leu His
            260                 265                 270

Gln Ser Ala Val Arg Lys Ala Ala Tyr Ser His Leu Ser Thr Ser Lys
            275                 280                 285

Arg Gln Ser Ser Ser Gly His Ala Val Glu Phe His Cys Leu Ala Pro
            290                 295                 300

Ser Ser Ala Gly Ser Gln Ser Gln Gly Ser Val Ser Ser Cys Trp Trp
305                 310                 315                 320
```

```
Leu Gln Phe Arg Asn Ser Lys Pro Cys Ser Glu Tyr Cys Leu Ser His
                325                 330                 335

Leu Val Asn Leu Arg Glu Asp Trp Gly Pro Cys Asp Asp His Gly Glu
                340                 345                 350

His His Ile Arg Ile Pro Arg Thr Pro Ala Arg Val Thr Gly Gly Val
                355                 360                 365

Phe Leu Val Asp Lys Asn Pro His Asn Thr Ala Glu Ser Arg Leu Val
370                 375                 380

Val Asp Phe Ser Gln Phe Ser Arg Gly Ile Thr Arg Val Ser Trp Pro
385                 390                 395                 400

Lys Phe Ala Val Pro Asn Leu Gln Ser Leu Thr Asn Leu Leu Ser Ser
                405                 410                 415

Asn Leu Ser Trp Leu Ser Leu Asp Val Ser Ala Ala Phe Tyr His Ile
                420                 425                 430

Pro Leu His Pro Ala Ala Met Pro His Leu Leu Ile Gly Ser Ser Gly
                435                 440                 445

Leu Ser Arg Tyr Val Ala Arg Leu Ser Ser Asn Ser Arg Ile Asn Asn
                450                 455                 460

Asn Gln Tyr Gly Thr Met Gln Asn Leu His Asp Ser Cys Ser Arg Gln
465                 470                 475                 480

Leu (2) INFORMATION FOR SEQ ID NO: 53:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 53:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn His Arg Val Ala Glu Asp Leu Asn Leu Gly Asn Pro Asn Val
                35                  40                  45

Ser Ile Pro Trp Thr His Lys Val Gly Asn Phe Thr Gly Leu Tyr Ser
50                  55                  60

Ser Thr Val Pro Val Phe Asn Pro Glu Trp Gln Thr Pro Ser Phe Pro
65                  70                  75                  80

Asp Ile His Leu Gln Glu Asp Ile Val Asp Arg Cys Lys Gln Phe Val
                85                  90                  95

Gly Pro Leu Thr Val Asn Glu Asn Arg Arg Leu Lys Leu Ile Met Pro
                100                 105                 110

Ala Arg Phe Tyr Pro Asn Val Thr Lys Tyr Leu Pro Leu Asp Lys Gly
                115                 120                 125

Ile Lys Pro Tyr Tyr Pro Glu His Val Val Asn His Tyr Phe Gln Thr
                130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Asp Leu Gln His Gly Arg Leu Val Phe Gln Thr Ser Lys Arg His
```

```
                  180             185             190
Gly Asp Lys Ser Phe Cys Pro Gln Ser Pro Gly Ile Leu Pro Arg Ser
            195                 200             205
Ser Val Gly Pro Cys Ile Gln Ser Gln Leu Arg Lys Ser Arg Leu Gly
        210                 215                 220
Pro Gln Pro Thr Gln Gly Gln Leu Ala Gly Arg Pro Gln Gly Gly Ser
225                 230                 235                 240
Gly Ser Ile Arg Ala Arg Ile His Pro Ser Pro Trp Gly Thr Val Gly
                245                 250                 255
Val Glu Pro Ser Gly Ser Gly His Thr His Ile Cys Ala Ser Ser Ser
            260                 265                 270
Ser Ser Cys Leu His Gln Ser Ala Val Arg Thr Ala Ala Tyr Ser Pro
        275                 280                 285
Ile Ser Thr Ser Lys Gly His Ser Ser Ser Gly His Ala Val Glu Leu
        290                 295                 300
His His Phe Pro Pro Asn Ser Ser Arg Ser Gln Ser Gln Gly Ser Val
305                 310                 315                 320
Leu Ser Cys Trp Trp Leu Gln Phe Arg Asn Ser Lys Pro Cys Ser Glu
                325                 330                 335
Tyr Cys Leu Ser His Ile Val Asn Leu Ile Glu Asp Trp Gly Pro Cys
            340                 345                 350
Ala Glu His Gly Glu His Arg Ile Arg Thr Pro Arg Thr Pro Ala Arg
        355                 360                 365
Val Thr Gly Gly Val Phe Leu Val Asp Lys Asn Pro His Asn Thr Thr
        370                 375                 380
Glu Ser Arg Leu Val Val Asp Phe Ser Gln Phe Ser Arg Gly Asn Thr
385                 390                 395                 400
Arg Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
            420                 425                 430
Ala Phe Tyr His Leu Pro Leu His Pro Ala Ala Met Pro His Leu Leu
        435                 440                 445
Val Gly Ser Ser Gly Leu Ser Arg Tyr Val Ala Arg Leu Ser Ser Asn
        450                 455                 460
Ser Arg Ile Ile Asn His Gln His Gly Thr Met Gln Asp Leu His Asp
465                 470                 475                 480
Ser Cys Ser Arg Asn Leu Tyr Val Ser Leu Met Leu Leu Tyr Lys Thr
                485                 490                 495
Tyr Gly Trp Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
        530                 535                 540
Leu Ala Phe Ser Tyr Met Asp Asp Val Val Leu Gly Ala Lys Ser Val
545                 550                 555                 560
Gln His Leu Glu Ser Leu Tyr Ala Ala Val Thr Asn Phe Leu Leu Ser
                565                 570                 575
Leu Gly Ile His Leu Asn Pro Asn Lys Thr Lys Arg Trp Gly Tyr Ser
            580                 585                 590
Leu Asn Phe Met Gly Tyr Val Ile Gly Ser Trp Gly Thr Trp Pro Gln
        595                 600                 605
```

```
Asp His Ile Val Gln Asn Phe Lys Leu Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
                660                 665                 670

Tyr Lys Ala Phe Leu Ser Lys Gln Tyr Met Thr Leu Tyr Pro Val Ala
                675                 680                 685

Arg Gln Arg Pro Gly Leu Cys Gln Val Phe Ala Asp Ala Thr Pro Thr
690                 695                 700

Gly Trp Gly Leu Ala Ile Gly His Gln Arg Met Arg Gly Thr Phe Val
705                 710                 715                 720

Ser Pro Leu Pro Ile His Thr Ala Glu Leu Leu Ala Ala Cys Phe Ala
                725                 730                 735

Arg Ser Arg Ser Gly Ala Asn Leu Ile Gly Thr Asp Asn Ser Val Val
                740                 745                 750

Leu Ser Arg Lys Tyr Thr Ser Phe Pro Trp Leu Leu Gly Cys Ala Ala
                755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu Arg Leu Pro Tyr Arg Pro Thr Thr Gly Arg Thr Ser Leu Tyr
                805                 810                 815

Ala Asp Ser Pro Ser Val Pro Ser His Leu Pro Asp Arg Val His Phe
                820                 825                 830

Ala Ser Pro Leu His Val Ala Trp Arg Pro Pro
                835                 840

(2) INFORMATION FOR SEQ ID NO: 54:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 54:

Met Pro Leu Ser Tyr Gln His Phe Arg Lys Leu Leu Leu Leu Asp Glu
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
                35                  40                  45

Ser Ile Pro Trp Thr His Lys Val Gly Asn Phe Thr Gly Leu Tyr Ser
                50                  55                  60

Ser Thr Val Pro Cys Phe Asn Pro Lys Trp Gln Thr Pro Ser Phe Pro
65                  70                  75                  80

Asp Ile His Leu Gln Glu Asp Ile Val Asp Arg Cys Lys Gln Phe Val
                85                  90                  95

Gly Pro Leu Thr Val Asn Glu Asn Arg Arg Leu Lys Leu Ile Met Pro
                100                 105                 110
```

-continued

```
Ala Arg Phe Tyr Pro Asn Val Thr Lys Tyr Leu Pro Leu Asp Lys Gly
            115                 120                 125

Ile Lys Pro Tyr Tyr Pro Glu His Val Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Asp Leu Gln His Gly Arg Leu Val Phe Gln Thr Ser Lys Arg His
            180                 185                 190

Gly Asp Lys Ser Phe Cys Pro Gln Ser Ser Gly Ile Leu Pro Arg Ser
        195                 200                 205

Ser Val Gly Pro Cys Ile Gln Ser Gln Leu Arg Lys Ser Arg Leu Gly
    210                 215                 220

Pro Gln Pro Glu Gln Gly Gln Leu Ala Gly Arg Gln Gln Gly Gly Ser
225                 230                 235                 240

Gly Ser Ile Arg Ala Arg Val His Pro Ser Pro Trp Gly Thr Val Gly
                245                 250                 255

Val Glu Pro Ser Gly Ser Gly Pro Thr His Asn Cys Ala Ser Ser Ser
            260                 265                 270

Ser Ser Cys Leu His Gln Ser Ala Val Arg Lys Ala Ala Tyr Ser Leu
        275                 280                 285

Ile Pro Thr Ser Lys Gly His Ser Ser Ser Gly His Ala Val Glu Leu
    290                 295                 300

His His Phe Pro Pro Asn Ser Ser Arg Ser Arg Ser Gln Gly Pro Val
305                 310                 315                 320

Leu Ser Cys Trp Trp Leu Gln Phe Arg Asn Ser Glu Pro Cys Ser Glu
                325                 330                 335

Tyr Cys Leu Cys His Ile Val Asn Leu Ile Glu Asp Trp Gly Pro Cys
            340                 345                 350

Thr Glu His Gly Glu His Arg Ile Arg Thr Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Asn
    450                 455                 460

Ser Arg Ile Ile Asn Asn Gln His Arg Thr Met Gln Asn Leu His Asp
465                 470                 475                 480

Ser Cys Ser Arg Asn Leu Tyr Val Ser Leu Met Leu Leu Tyr Lys Thr
                485                 490                 495

Tyr Gly Trp Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525
```

-continued

Phe Thr Ser Ala Ile Cys Ser Val Val Arg Arg Ala Phe Pro His Cys
    530                 535                 540

Leu Ala Phe Ser Tyr Met Asp Asp Met Val Leu Gly Ala Lys Ser Val
545                 550                 555                 560

Gln His Leu Glu Ser Leu Tyr Ala Ala Val Thr Asn Phe Leu Leu Ser
                565                 570                 575

Leu Gly Ile His Leu Asn Pro His Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Met Trp Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
            660                 665                 670

Tyr Lys Ala Phe Leu Thr Lys Gln Tyr Leu Asn Leu Tyr Pro Val Ala
        675                 680                 685

Arg Gln Arg Pro Gly Leu Cys Gln Val Phe Ala Asp Ala Thr Pro Thr
    690                 695                 700

Gly Trp Gly Leu Ala Ile Gly His Gln Arg Met Arg Gly Thr Phe Val
705                 710                 715                 720

Ser Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Arg Leu Leu Tyr Arg Pro Thr Thr Gly Arg Thr Ser Leu Tyr
                805                 810                 815

Ala Asp Ser Pro Ser Val Pro Ser His Leu Pro Asp Arg Val His Phe
            820                 825                 830

Ala Ser Pro Leu His Val Ala Trp Arg Pro Pro
        835                 840

(2) INFORMATION FOR SEQ ID NO: 55:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 55:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

```
Leu Asn Arg Arg Val Ala Glu Asp Leu Asn Leu Gly Asn Leu Asn Val
             35                  40                  45

Ser Ile Pro Trp Thr His Lys Val Gly Asn Phe Thr Gly Leu Tyr Ser
         50                  55                  60

Ser Thr Val Pro Ser Phe Asn Pro Gln Trp Gln Thr Pro Ser Phe Pro
 65                  70                  75                  80

Asp Ile His Leu Gln Glu Asp Ile Ile Asn Lys Cys Lys Gln Phe Val
                     85                  90                  95

Gly Pro Leu Thr Val Asn Glu Lys Arg Leu Lys Leu Ile Met Pro
                    100                 105                 110

Ala Arg Phe Tyr Pro Asn Val Thr Lys Tyr Leu Pro Leu Asp Lys Gly
             115                 120                 125

Ile Lys Pro Tyr Tyr Pro Glu His Val Asn His Tyr Phe Gln Thr
             130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                 165                 170                 175

Gln Glu Leu Gln His Gly Arg Leu Val Leu Gln Thr Ser Thr Arg His
             180                 185                 190

Gly Asp Lys Ser Phe Arg Pro Gln Ser Ser Gly Ile Leu Ser Arg Ser
             195                 200                 205

Pro Val Gly Pro Cys Ile Gln Ser Gln Leu Arg Gln Ser Arg Leu Gly
             210                 215                 220

Pro Gln Pro Thr Gln Gly Gln Leu Ala Gly Leu Gln Gly Gly Ser
225                 230                 235                 240

Gly Ser Ile Arg Ala Gly Ile His Ser Thr Pro Trp Gly Thr Val Gly
                 245                 250                 255

Val Glu Pro Ser Ser Ser Gly His Thr His Asn Cys Ala Asn Ser Ser
                 260                 265                 270

Ser Ser Cys Leu His Gln Ser Ala Val Arg Lys Glu Ala Tyr Ser Pro
             275                 280                 285

Val Ser Thr Ser Lys Arg His Ser Ser Ser Gly Asn Ala Val Glu Leu
             290                 295                 300

His His Val Pro Pro Asn Ser Ser Arg Ser Gln Ser Gln Gly Ser Val
305                 310                 315                 320

Leu Ser Cys Trp Trp Leu Gln Phe Arg Asn Ser Lys Pro Cys Ser Glu
                 325                 330                 335

His Cys Leu Phe His Ile Val Asn Leu Ile Asp Asp Trp Gly Pro Cys
                 340                 345                 350

Ala Glu His Gly Glu His Arg Ile Arg Thr Pro Arg Thr Pro Ala Arg
             355                 360                 365

Val Thr Gly Gly Val Phe Leu Val Asp Lys Asn Pro His Asn Thr Ser
370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                 405                 410                 415

Asn Leu Leu Ser Ser Asp Leu Ser Trp Leu Ser Leu Asp Val Ser Ala
             420                 425                 430

Ala Phe Tyr His Leu Pro Leu His Pro Ala Ala Met Pro His Leu Leu
             435                 440                 445

Val Gly Ser Ser Gly Leu Ser Arg Tyr Val Ala Arg Leu Ser Ser Asn
```

-continued

```
              450                 455                 460
Ser Arg Ile Ile Asn His Gln His Arg Thr Met Gln Asn Leu His Asp
465                 470                 475                 480

Ser Cys Ser Arg Asn Leu Tyr Val Ser Leu Met Leu Leu Tyr Lys Thr
                485                 490                 495

Tyr Gly Arg Lys Leu His Leu Tyr Ser His Pro Ile Ile Leu Gly Phe
                500                 505                 510

Arg Lys Ile Pro Met Gly Val Gly Leu Ser Pro Phe Leu Leu Ala Gln
                515                 520                 525

Phe Thr Ser Ala Ile Cys Ser Val Val Arg Arg Ala Phe Pro His Cys
530                 535                 540

Leu Ala Phe Ser Tyr Met Asp Asp Val Val Leu Gly Ala Lys Ser Val
545                 550                 555                 560

Gln His Leu Glu Ser Leu Tyr Ala Ala Val Thr Asn Phe Leu Leu Ser
                565                 570                 575

Leu Gly Ile His Leu Asn Pro Gln Lys Thr Lys Arg Trp Gly Tyr Ser
                580                 585                 590

Leu Asn Phe Met Gly Tyr Val Ile Gly Ser Trp Gly Thr Leu Pro Gln
                595                 600                 605

Glu His Ile Val Leu Lys Ile Lys Gln Cys Phe Arg Lys Leu Pro Val
                610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
                660                 665                 670

Tyr Lys Ala Phe Leu Asn Lys Gln Tyr Leu Asn Leu Tyr Pro Val Ala
                675                 680                 685

Arg Gln Arg Pro Gly Leu Cys Gln Val Phe Ala Asp Ala Thr Pro Thr
                690                 695                 700

Gly Trp Gly Leu Ala Ile Gly His Gln Arg Met Arg Gly Thr Phe Val
705                 710                 715                 720

Ser Pro Leu Pro Ile His Thr Val Glu Leu Leu Ala Ala Cys Phe Ala
                725                 730                 735

Arg Ser Arg Ser Gly Ala Lys Leu Ile Gly Thr Asp Asn Ser Val Val
                740                 745                 750

Leu Ser Arg Lys Tyr Thr Ser Phe Pro Trp Leu Leu Gly Cys Ala Ala
                755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu Arg Leu Pro Tyr Arg Pro Thr Thr Gly Arg Thr Ser Leu Tyr
                805                 810                 815

Ala Asp Ser Pro Ser Val Pro Ser His Leu Pro Asp Arg Val His Phe
                820                 825                 830

Ala Ser Pro Leu His Val Ala Trp Arg Pro Pro
                835                 840
```

(2) INFORMATION FOR SEQ ID NO: 56:

(i) SEQUENCE CHARACTERISTICS:
        (A) LENGTH: 843 amino acids (B) TYPE: amino acid
(C) STRANDEDNESS: <Unknown>
(D) TOPOLOGY: linear (ii) MOLECULE TYPE: protein (xi) SEQUENCE DESCRIPTION: SEQ ID NO: 56:

```
Met Pro Leu Ser Tyr Gln His Phe Arg Lys Leu Leu Leu Leu Asp Asp
1               5                   10                  15

Glu Ala Gly Pro Leu Glu Glu Glu Leu Pro His Leu Ala Asp Glu Gly
                20                  25                  30

Leu Asn Arg Pro Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Ser Phe Asn Pro Lys Trp Gln Thr Pro Ser Phe Pro
65                  70                  75                  80

Asp Ile His Leu Gln Glu Asp Ile Ile Asn Arg Cys Glu Gln Phe Val
                85                  90                  95

Gly Pro Leu Thr Val Asn Glu Asn Arg Arg Leu Lys Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Val Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Asp Leu Gln His Gly Arg Leu Val Leu Gln Thr Ser Thr Arg His
            180                 185                 190

Gly Asp Lys Ser Phe Arg Pro Gln Ser Ser Gly Ile Leu Ser Arg Ser
        195                 200                 205

Pro Val Gly Pro Cys Ile Gln Ser Gln Leu Arg Gln Ser Arg Leu Gly
210                 215                 220

Pro Gln Pro Thr Gln Gly Gln Leu Ala Gly Leu Gln Gln Gly Gly Ser
225                 230                 235                 240

Gly Ser Ile Arg Ala Gly Ile His Ser Thr Pro Trp Gly Thr Val Gly
                245                 250                 255

Val Glu Pro Ser Ser Ser Gly His Thr His Asn Cys Ala Asn Ser Ser
            260                 265                 270

Ser Ser Cys Leu His Gln Ser Ala Val Arg Lys Glu Ala Tyr Ser Pro
        275                 280                 285

Val Ser Thr Ser Lys Arg His Ser Ser Gly His Ala Val Glu Leu
290                 295                 300

His His Val Pro Pro Asn Ser Ser Arg Ser Gln Ser Gln Gly Ser Val
305                 310                 315                 320

Leu Ser Cys Trp Trp Leu Gln Phe Arg Asn Ser Lys Pro Cys Ser Glu
                325                 330                 335

His Cys Leu Phe His Ile Val Asn Leu Ile Glu Asp Trp Gly Pro Cys
            340                 345                 350

Ala Glu His Gly Glu His Arg Ile Arg Thr Pro Arg Thr Pro Ala Arg
        355                 360                 365

Val Thr Gly Gly Val Phe Leu Val Asp Lys Asn Pro His Asn Thr Thr
370                 375                 380
```

```
Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
            405                 410                 415

Asn Leu Leu Ser Ser Asp Leu Ser Trp Leu Ser Leu Asp Val Ser Ala
            420                 425                 430

Ala Phe Tyr His Leu Pro Leu His Pro Ala Ala Met Pro His Leu Leu
            435                 440                 445

Val Gly Ser Ser Gly Leu Ser Arg Tyr Val Ala Arg Leu Ser Ser Asn
450                 455                 460

Ser Arg Ile Ile Asn His Gln His Arg Thr Met Gln Asn Leu His Asp
465                 470                 475                 480

Ser Cys Ser Arg Asn Leu Tyr Val Ser Leu Met Leu Leu Tyr Lys Thr
                485                 490                 495

Tyr Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
530                 535                 540

Leu Ala Phe Ser Tyr Met Asp Asp Val Val Leu Gly Ala Lys Ser Val
545                 550                 555                 560

Gln His Leu Glu Ser Leu Tyr Ala Ala Val Thr Asn Phe Leu Leu Ser
                565                 570                 575

Leu Gly Ile His Leu Asn Pro Gln Lys Thr Lys Arg Trp Gly Tyr Ser
            580                 585                 590

Leu Asn Phe Met Gly Tyr Val Ile Gly Ser Trp Gly Thr Leu Pro Gln
            595                 600                 605

Glu His Ile Val Leu Lys Leu Gln Cys Phe Arg Lys Leu Pro Val
610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
            660                 665                 670

Tyr Lys Ala Phe Leu Thr Lys Gln Tyr Leu Asn Leu Tyr Pro Val Ala
            675                 680                 685

Arg Gln Arg Pro Gly Leu Cys Gln Val Phe Ala Asp Ala Thr Pro Thr
690                 695                 700

Gly Trp Gly Leu Ala Ile Gly His Gln Arg Met Arg Gly Thr Phe Val
705                 710                 715                 720

Ser Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
            755                 760                 765

Asn Trp Ile Leu Arg Gly Thr Ser Phe Val Tyr Val Pro Ser Ala Leu
            770                 775                 780

Asn Pro Ala Asp Asp Pro Ser Arg Gly Arg Leu Gly Leu Tyr Arg Pro
785                 790                 795                 800
```

-continued

```
Leu Leu Arg Leu Pro Tyr Arg Pro Thr Thr Gly Arg Thr Ser Leu Tyr
            805                 810                 815

Ala Asp Ser Pro Ser Val Pro Ser Arg Leu Pro Asp Arg Val His Phe
            820                 825                 830

Ala Ser Pro Leu His Val Ala Trp Arg Pro Pro
            835                 840

(2) INFORMATION FOR SEQ ID NO: 57:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 57:

Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
                20                  25                  30

Ala Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                  55                  60

Tyr Ser Ser Thr Ala Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Thr His Thr Lys Tyr Leu Pro Leu Asp
                115                 120                 125

Lys Gly Ile Lys Pro Tyr Tyr Pro Asp Gln Val Val Asn His Tyr Phe
    130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
                180                 185                 190

Arg His Gly Asp Glu Ser Phe Cys Ser Gln Pro Ser Gly Ile Leu Ser
                195                 200                 205

Arg Ser Ser Val Gly Pro Cys Ile Arg Ser Gln Leu Lys Gln Ser Arg
    210                 215                 220

Leu Gly Leu Gln Pro His Gln Gly Pro Leu Ala Ser Ser Gln Pro Gly
225                 230                 235                 240

Arg Ser Gly Ser Ile Arg Ala Arg Val His Pro Ser Thr Arg Arg Cys
                245                 250                 255

Phe Gly Val Glu Pro Ser Gly Ser Gly His Val Asp Pro Ser Val Asn
                260                 265                 270

Asn Ser Ser Ser Cys Leu Arg Gln Ser Ala Val Arg Lys Ala Ala Tyr
    275                 280                 285

Ser His Leu Ser Thr Ser Lys Arg Gln Ser Ser Ser Gly His Ala Val
    290                 295                 300
```

-continued

```
Glu Phe His Cys Leu Pro Pro Ser Ser Ala Arg Pro Gln Ser Gln Gly
305                 310                 315                 320

Ser Val Phe Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Arg Gly
            340                 345                 350

Pro Cys Asp Glu His Gly Glu His His Ile Arg Ile Pro Arg Thr Pro
        355                 360                 365

Ala Arg Val Thr Gly Gly Val Phe Leu Val Asp Lys Asn Pro His Asn
370                 375                 380

Thr Ala Glu Ser Arg Leu Val Val Asp Phe Ser Gln Phe Ser Arg Gly
385                 390                 395                 400

Ile Thr Arg Val Ser Trp Pro Lys Phe Ala Ile Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
        435                 440                 445

Leu Leu Ile Gly Ser Ser Gly Leu Ser Arg Tyr Val Ala Arg Leu Ser
450                 455                 460

Ser Asn Ser Arg Ile Asn Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
            500                 505                 510

Gly Phe Arg Lys Ile Pro Met Gly Val Gly Leu Ser Pro Phe Leu Leu
        515                 520                 525

Ala Gln Phe Thr Ser Ala Ile Cys Ser Val Val Arg Arg Ala Phe Pro
530                 535                 540

His Cys Leu Ala Phe Ser Tyr Met Asp Asp Val Val Leu Gly Ala Lys
545                 550                 555                 560

Ser Val Gln His Arg Glu Phe Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Ser Trp Gly Thr Leu
        595                 600                 605

Pro Gln Asp His Ile Val Gln Lys Ile Lys His Cys Phe Arg Lys Leu
610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
        675                 680                 685

Val Ala Arg Gln Arg Pro Gly Leu Cys Gln Val Phe Ala Asp Ala Thr
690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
```

-continued

```
                725                 730                 735
Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
            755                 760                 765

Ala Ala Asn Trp Ile Leu Arg Gly Thr Ser Phe Val Tyr Val Pro Ser
            770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
            805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
            835                 840                 845
```

(2) INFORMATION FOR SEQ ID NO: 58:

(i) SEQUENCE CHARACTERISTICS:
        (A) LENGTH: 845 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 58:

```
Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
            20                  25                  30

Ala Asp Leu His Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
            85                  90                  95

Phe Val Gly Pro Leu Thr Val Asn Glu Lys Arg Arg Leu Lys Leu Ile
            100                 105                 110

Met Pro Ala Arg Phe Tyr Pro Thr His Thr Lys Tyr Leu Pro Leu Asp
            115                 120                 125

Lys Gly Ile Lys Pro Tyr Tyr Pro Asp Gln Val Val Asn His Tyr Phe
            130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
            165                 170                 175

Trp Glu Gln Glu Leu Gln His Gly Arg Leu Val Ile Lys Thr Ser Gln
            180                 185                 190

Arg His Gly Asp Glu Ser Phe Cys Ser Gln Ser Ser Gly Ile Leu Ser
            195                 200                 205

Arg Ser Ser Val Gly Pro Cys Ile Arg Ser Gln Leu Lys Gln Ser Arg
            210                 215                 220

Leu Gly Leu Gln Pro Arg Gln Gly Arg Leu Ala Ser Ser Gln Pro Ser
```

```
              225                 230                 235                 240
        Arg Ser Gly Ser Ile Arg Ala Lys Ala His Pro Ser Thr Arg Arg Tyr
                        245                 250                 255
        Phe Gly Val Glu Pro Ser Gly Gly His Ile Asp His Ser Val Asn
                    260                 265                 270
        Asn Ser Ser Ser Cys Leu His Gln Ser Ala Val Arg Lys Ala Ala Tyr
                    275                 280                 285
        Ser His Leu Ser Thr Ser Lys Arg Gln Ser Ser Gly His Ala Val
            290                 295                 300
        Glu Phe His Cys Leu Pro Pro Asn Ser Ala Gly Ser Gln Ser Gln Gly
        305                 310                 315                 320
        Ser Val Ser Ser Cys Trp Trp Leu Gln Phe Arg Asn Ser Lys Pro Cys
                        325                 330                 335
        Ser Glu Tyr Cys Leu Ser His Leu Val Asn Leu Arg Glu Asp Trp Gly
                        340                 345                 350
        Pro Cys Asp Glu His Gly Glu His His Ile Arg Ile Pro Arg Thr Pro
                    355                 360                 365
        Ala Arg Val Thr Gly Gly Val Phe Leu Val Asp Lys Asn Pro His Asn
            370                 375                 380
        Thr Ala Glu Ser Arg Leu Val Val Asp Phe Ser Gln Phe Ser Arg Gly
        385                 390                 395                 400
        Ile Ser Arg Val Ser Trp Pro Lys Phe Ala Val Pro Asn Leu Gln Ser
                        405                 410                 415
        Leu Thr Asn Leu Leu Ser Ser Asn Leu Ser Trp Leu Ser Leu Asp Val
                    420                 425                 430
        Ser Ala Ala Phe Tyr His Ile Pro Leu His Pro Ala Ala Met Pro His
                    435                 440                 445
        Leu Leu Ile Gly Ser Ser Gly Leu Ser Arg Tyr Val Ala Arg Leu Ser
            450                 455                 460
        Ser Asn Ser Arg Ile Asn Asn Asn Gln Tyr Gly Thr Met Gln Asn Leu
        465                 470                 475                 480
        His Asp Ser Cys Ser Arg Gln Leu Tyr Val Ser Leu Met Leu Leu Tyr
                        485                 490                 495
        Lys Thr Tyr Gly Trp Lys Leu His Leu Tyr Ser His Pro Ile Val Leu
                    500                 505                 510
        Gly Phe Arg Lys Ile Pro Met Gly Val Gly Leu Ser Pro Phe Leu Leu
            515                 520                 525
        Ala Gln Phe Thr Ser Ala Ile Cys Ser Val Val Arg Arg Ala Phe Pro
            530                 535                 540
        His Cys Leu Ala Phe Ser Tyr Met Asp Asp Val Val Leu Gly Ala Lys
        545                 550                 555                 560
        Ser Val Gln His Arg Glu Ser Leu Tyr Thr Ala Val Thr Asn Phe Leu
                        565                 570                 575
        Leu Ser Leu Gly Ile His Leu Asn Pro Asn Lys Thr Lys Arg Trp Gly
                    580                 585                 590
        Tyr Ser Leu Asn Phe Met Gly Tyr Ile Ile Gly Ser Trp Gly Thr Leu
                    595                 600                 605
        Pro Gln Asp His Ile Val Gln Lys Ile Lys His Cys Phe Arg Lys Leu
            610                 615                 620
        Pro Val Asn Arg Pro Ile Asp Trp Lys Val Cys Gln Arg Ile Val Gly
        625                 630                 635                 640
        Leu Leu Gly Phe Ala Ala Pro Phe Thr Gln Cys Gly Tyr Pro Ala Leu
                        645                 650                 655
```

-continued

```
Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
            675                 680                 685

Val Ala Arg Gln Arg Pro Gly Leu Cys Gln Val Phe Ala Asp Ala Thr
            690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
                740                 745                 750

Val Val Leu Ser Arg Lys Tyr Thr Ser Phe Pro Trp Leu Leu Gly Cys
                755                 760                 765

Thr Ala Asn Trp Ile Leu Arg Gly Thr Ser Phe Val Tyr Val Pro Ser
            770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
                805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
            835                 840                 845

(2) INFORMATION FOR SEQ ID NO: 59:

(i) SEQUENCE CHARACTERISTICS:
        (A) LENGTH: 843 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 59:

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Val Phe Asn Pro Asp Trp Lys Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
            115                 120                 125

Ile Lys Pro Tyr Tyr Pro Glu Tyr Ala Val Asn His Tyr Phe Lys Thr
            130                 135                 140

Arg His Tyr Leu His Thr Leu Trp Lys Ala Gly Ile Leu Tyr Lys Arg
145                 150                 155                 160
```

```
Glu Thr Thr Arg Ser Ala Ser Phe Cys Gly Ser Pro Tyr Ser Trp Glu
                165                 170                 175
Gln Glu Leu Gln His Gly Arg Leu Val Phe Gln Thr Ser Thr Arg His
            180                 185                 190
Gly Asp Glu Ser Phe Cys Ser Gln Ser Ser Gly Ile Leu Ser Arg Ser
        195                 200                 205
Pro Val Gly Pro Cys Val Arg Ser Gln Leu Lys Gln Ser Arg Leu Gly
    210                 215                 220
Leu Gln Pro Gln Gln Gly Ser Leu Ala Arg Gly Lys Ser Gly Arg Ser
225                 230                 235                 240
Gly Ser Ile Trp Ser Arg Val His Pro Thr Thr Arg Arg Pro Phe Gly
                245                 250                 255
Val Glu Pro Ser Gly Ser Gly His Ile Asp Asn Thr Ala Ser Ser Thr
            260                 265                 270
Ser Ser Cys Leu His Gln Ser Ala Val Arg Lys Thr Ala Tyr Ser His
        275                 280                 285
Leu Ser Thr Ser Lys Arg Gln Ser Ser Gly His Ala Val Glu Leu
    290                 295                 300
His Asn Ile Pro Pro Ser Ser Ala Arg Ser Gln Ser Glu Gly Pro Ile
305                 310                 315                 320
Phe Ser Cys Trp Trp Leu Gln Phe Arg Asn Ser Lys Pro Cys Ser Asp
                325                 330                 335
Tyr Cys Leu Thr His Ile Val Asn Leu Leu Glu Asp Trp Gly Pro Cys
            340                 345                 350
Thr Glu His Gly Glu His Asn Ile Arg Ile Pro Arg Thr Pro Ala Arg
        355                 360                 365
Val Thr Gly Gly Val Phe Leu Val Asp Lys Asn Pro His Asn Thr Thr
    370                 375                 380
Glu Ser Arg Leu Val Val Asp Phe Ser Gln Phe Ser Arg Gly Ser Thr
385                 390                 395                 400
His Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
            420                 425                 430
Ala Phe Tyr His Ile Pro Leu His Pro Ala Ala Met Pro His Leu Leu
        435                 440                 445
Val Gly Ser Ser Gly Leu Pro Arg Tyr Val Ala Arg Leu Ser Ser Thr
    450                 455                 460
Ser Arg Asn Ile Asn Tyr Gln His Gly Thr Met Gln Asn Leu His Asp
465                 470                 475                 480
Ser Cys Ser Arg Asn Leu Tyr Val Ser Leu Leu Leu Leu Tyr Lys Thr
                485                 490                 495
Phe Gly Arg Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
    530                 535                 540
Leu Ala Phe Ser Tyr Met Asp Asp Val Val Leu Gly Ala Lys Ser Val
545                 550                 555                 560
Gln His Leu Glu Ser Leu Phe Thr Ser Ile Thr Asn Phe Leu Leu Ser
                565                 570                 575
```

-continued

```
Leu Gly Ile His Leu Asn Pro Asn Lys Thr Lys Arg Trp Gly Tyr Ser
            580                 585                 590
Leu Asn Phe Met Gly Tyr Val Ile Gly Ser Trp Gly Thr Leu Pro Gln
        595                 600                 605
Glu His Ile Val Gln Lys Leu Lys Gln Cys Phe Arg Lys Leu Pro Val
    610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
            645                 650                 655
Leu Tyr Ala Cys Ile Gln Ser Lys Gln Ala Phe Thr Phe Ser Pro Thr
        660                 665                 670
Tyr Lys Ala Phe Leu Cys Lys Gln Tyr Leu Asn Leu Tyr Pro Val Ala
    675                 680                 685
Arg Gln Arg Ser Gly Leu Cys Gln Val Phe Ala Asp Ala Thr Pro Thr
690                 695                 700
Gly Trp Gly Leu Ala Ile Gly His Arg Arg Met Arg Gly Thr Phe Val
705                 710                 715                 720
Ala Pro Leu Pro Ile His Thr Ala Glu Leu Leu Ala Ala Cys Phe Ala
            725                 730                 735
Arg Ser Arg Ser Gly Ala Lys Leu Ile Gly Thr Asp Asn Ser Val Val
        740                 745                 750
Leu Ser Arg Lys Tyr Thr Ser Phe Pro Trp Leu Leu Gly Cys Ala Ala
    755                 760                 765
Asn Trp Ile Leu Arg Gly Thr Ser Phe Val Tyr Val Pro Ser Ala Leu
770                 775                 780
Asn Pro Ala Asp Asp Pro Ser Arg Gly Arg Leu Gly Leu Tyr Arg Pro
785                 790                 795                 800
Leu Leu His Leu Pro Phe Arg Pro Thr Thr Gly Arg Thr Ser Leu Tyr
            805                 810                 815
Ala Val Ser Pro Ser Val Pro Ser His Leu Pro Asp Arg Val His Phe
        820                 825                 830
Ala Ser Pro Leu His Val Ala Trp Arg Pro Pro
    835                 840
```

(2) INFORMATION FOR SEQ ID NO: 60:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 60:

```
Met Pro Leu Ser Tyr Gln His Phe Arg Arg Leu Leu Leu Leu Asp Asp
1               5                   10                  15
Glu Ala Gly Pro Leu Glu Glu Glu Leu Pro Arg Leu Ala Asp Glu Gly
            20                  25                  30
Leu Asn Arg Arg Val Ala Glu Asp Leu Asn Leu Gly Asn Leu Asn Val
        35                  40                  45
Ser Ile Pro Trp Thr His Lys Val Gly Asn Phe Thr Gly Leu Tyr Ser
    50                  55                  60
Ser Thr Val Pro Val Phe Asn Pro His Trp Lys Thr Pro Ser Phe Pro
65                  70                  75                  80
```

```
Asn Ile His Leu His Gln Asp Ile Ile Lys Lys Cys Glu Gln Phe Val
            85                  90                  95
Gly Pro Leu Thr Val Asn Glu Lys Arg Arg Leu Gln Leu Ile Met Pro
            100                 105                 110
Ala Arg Phe Tyr Pro Lys Val Thr Lys Tyr Leu Pro Leu Asp Lys Gly
            115                 120                 125
Ile Lys Pro Tyr Pro Glu His Leu Val Asn His Tyr Phe Gln Thr
130                 135                 140
Arg His Tyr Leu His Thr Leu Trp Lys Ala Gly Ile Leu Tyr Lys Arg
145                 150                 155                 160
Glu Thr Thr His Ser Ala Ser Phe Cys Gly Ser Pro Tyr Ser Trp Glu
            165                 170                 175
Gln Asp Leu Gln His Gly Ala Glu Ser Phe His Gln Ser Ser Gly
            180                 185                 190
Ile Leu Ser Arg Pro Pro Val Gly Ser Ser Leu Gln Ser Lys His Arg
            195                 200                 205
Lys Ser Arg Leu Gly Leu Gln Ser Gln Gln Gly His Leu Ala Arg Arg
210                 215                 220
Gln Gln Gly Arg Ser Trp Ser Ile Arg Ala Gly Phe His Pro Thr Ala
225                 230                 235                 240
Arg Arg Pro Phe Gly Val Glu Pro Ser Gly Ser Gly His Thr Thr Asn
            245                 250                 255
Phe Ala Ser Lys Ser Ala Ser Cys Leu His Gln Ser Pro Val Arg Lys
            260                 265                 270
Ala Ala Tyr Pro Ala Val Ser Thr Phe Glu Lys His Ser Ser Ser Gly
            275                 280                 285
His Ala Val Glu Phe His Asn Leu Pro Pro Asn Ser Ala Arg Ser Gln
            290                 295                 300
Ser Glu Arg Pro Val Phe Pro Cys Trp Trp Leu Gln Phe Arg Asn Ser
305                 310                 315                 320
Lys Pro Cys Ser Asp Tyr Cys Leu Ser Leu Ile Val Asn Leu Leu Glu
            325                 330                 335
Asp Trp Gly Pro Cys Ala Glu His Gly Glu His Ile Arg Ile Pro
            340                 345                 350
Arg Thr Pro Ser Arg Val Thr Gly Gly Val Phe Leu Val Asp Lys Asn
            355                 360                 365
Pro His Asn Thr Ala Glu Ser Arg Leu Val Val Asp Phe Ser Gln Phe
            370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
            405                 410                 415
Leu Asp Val Ser Ala Ala Phe Tyr His Leu Pro Leu His Pro Ala Ala
            420                 425                 430
Met Pro His Leu Leu Val Gly Ser Ser Gly Leu Ser Arg Tyr Val Ala
            435                 440                 445
Arg Leu Ser Ser Asn Ser Arg Ile Leu Asn Asn Gln His Gly Thr Met
            450                 455                 460
Pro Asp Leu His Asp Tyr Cys Ser Arg Asn Leu Tyr Val Ser Leu Leu
465                 470                 475                 480
Leu Leu Tyr Gln Thr Phe Gly Arg Lys Leu His Leu Tyr Ser His Pro
            485                 490                 495
Ile Ile Leu Gly Phe Arg Lys Ile Pro Met Gly Val Gly Leu Ser Pro
```

```
                500             505             510
Phe Leu Leu Ala Gln Phe Thr Ser Ala Ile Cys Ser Val Val Arg Arg
        515                 520                 525
Ala Phe Pro His Cys Leu Ala Phe Ser Tyr Met Asp Asp Val Val Leu
        530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu Asn Phe Met Gly Tyr Val Ile Gly Cys Tyr
            580                 585                 590
Gly Ser Leu Pro Gln Glu His Ile Ile Gln Lys Ile Lys Glu Cys Phe
            595                 600                 605
Arg Lys Leu Pro Ile Asn Arg Pro Ile Asp Trp Lys Val Cys Gln Arg
        610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ser Lys Gln Ala Phe
                645                 650                 655
Thr Phe Ser Pro Thr Tyr Lys Ala Phe Leu Cys Lys Gln Tyr Leu Asn
                660                 665                 670
Leu Tyr Pro Val Ala Arg Gln Arg Pro Gly Leu Cys Gln Val Phe Ala
            675                 680                 685
Asp Ala Thr Pro Thr Gly Trp Gly Leu Val Met Gly His Gln Arg Met
        690                 695                 700
Arg Gly Thr Phe Ser Ala Pro Leu Pro Ile His Thr Ala Glu Leu Leu
705                 710                 715                 720
Ala Ala Cys Phe Ala Arg Ser Arg Ser Gly Ala Asn Ile Ile Gly Thr
                725                 730                 735
Asp Asn Ser Val Val Leu Ser Arg Lys Tyr Thr Ser Phe Pro Trp Leu
                740                 745                 750
Leu Gly Cys Ala Ala Asn Trp Ile Leu Arg Gly Thr Ser Phe Val Tyr
            755                 760                 765
Val Pro Ser Ala Leu Asn Pro Ala Asp Asp Pro Ser Arg Gly Arg Leu
770                 775                 780
Gly Leu Ser Arg Pro Leu Leu Arg Leu Pro Phe Arg Pro Thr Thr Gly
785                 790                 795                 800
Arg Thr Ser Leu Tyr Ala Asp Ser Pro Ser Val Pro Ser His Leu Pro
                805                 810                 815
Asp Arg Val His Phe Ala Ser Pro Leu His Val Ala Trp Arg Pro Pro
            820                 825                 830

(2) INFORMATION FOR SEQ ID NO: 61:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 61:

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
```

-continued

```
                 20                  25                  30
Leu Asn Arg Val Ala Glu Asp Leu Asn Leu Gly Asn Leu Asn Val
             35                  40                  45
Ser Ile Pro Trp Thr His Lys Val Gly Asn Phe Thr Gly Leu Tyr Ser
 50                  55                  60
Ser Thr Val Pro Val Phe Asn Pro His Trp Lys Thr Pro Ser Phe Pro
 65                  70                  75                  80
Asn Ile His Leu His Gln Asp Ile Ile Lys Cys Glu Gln Phe Val
                 85                  90                  95
Gly Pro Leu Thr Val Asn Glu Lys Arg Arg Leu Gln Leu Ile Met Pro
                100                 105                 110
Ala Arg Phe Tyr Pro Asn Val Thr Lys Tyr Leu Pro Leu Asp Lys Gly
             115                 120                 125
Ile Lys Pro Tyr Tyr Pro Glu Tyr Leu Val Asn His Tyr Phe Gln Thr
         130                 135                 140
Arg His Tyr Leu His Thr Leu Trp Lys Ala Gly Ile Leu Tyr Lys Arg
145                 150                 155                 160
Glu Thr Thr His Ser Ala Ser Phe Cys Gly Ser Pro Tyr Ser Trp Glu
                165                 170                 175
Gln Glu Leu Gln His Gly Ala Glu Ser Phe His Gln Ser Ser Gly
             180                 185                 190
Ile Leu Ser Arg Pro Pro Val Gly Ser Ser Leu Gln Ser Lys His Arg
         195                 200                 205
Lys Ser Arg Leu Gly Leu Gln Ser Gln Gln Gly His Leu Ala Arg Arg
210                 215                 220
Gln Gln Gly Arg Ser Trp Ser Ile Arg Ala Gly Ile His Pro Thr Thr
225                 230                 235                 240
Arg Arg Pro Phe Gly Val Glu Pro Ser Gly Ser Gly His Thr Arg Asn
                245                 250                 255
Val Ala Ser Lys Ser Ala Ser Cys Leu Tyr Gln Ser Pro Val Arg Lys
             260                 265                 270
Ala Ala Tyr Pro Ala Val Ser Thr Phe Glu Lys His Ser Ser Ser Gly
         275                 280                 285
His Ala Val Glu Leu His Asn Leu Pro Pro Asn Ser Ala Arg Ser Gln
    290                 295                 300
Ser Glu Arg Pro Val Phe Pro Cys Trp Trp Leu Gln Phe Arg Asn Ser
305                 310                 315                 320
Lys Pro Cys Ser Asp Tyr Cys Leu Ser His Ile Val Asn Leu Leu Glu
                325                 330                 335
Asp Trp Gly Pro Cys Ala Glu His Gly Glu His His Ile Arg Ile Pro
             340                 345                 350
Arg Thr Pro Ala Arg Val Thr Gly Gly Val Phe Leu Val Asp Lys Asn
         355                 360                 365
Pro His Asn Thr Ala Glu Ser Arg Leu Val Val Asp Phe Ser Gln Phe
    370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Val Ser Ala Ala Phe Tyr His Leu Pro Leu His Pro Ala Ala
             420                 425                 430
Met Pro His Leu Leu Val Gly Ser Ser Gly Leu Ser Arg Tyr Val Ala
         435                 440                 445
```

-continued

```
Arg Leu Ser Ser Asn Ser Arg Ile Phe Asn Tyr Gln His Gly Thr Met
    450                 455                 460
Gln Asn Leu His Asp Ser Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                485                 490                 495
Ile Ile Leu Gly Phe Arg Lys Ile Pro Met Gly Val Gly Leu Ser Pro
            500                 505                 510
Phe Leu Leu Ala Gln Phe Thr Ser Ala Ile Cys Ser Val Val Arg Arg
        515                 520                 525
Ala Phe Pro His Cys Leu Ala Phe Ser Tyr Met Asp Asp Val Val Leu
    530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu His Phe Met Gly Tyr Val Ile Gly Cys Tyr
            580                 585                 590
Gly Ser Leu Pro Gln Asp His Ile Ile Gln Lys Ile Lys Glu Cys Phe
        595                 600                 605
Arg Lys Leu Pro Val Asn Arg Pro Ile Asp Trp Lys Val Cys Gln Arg
    610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ser Lys Gln Ala Phe
                645                 650                 655
Thr Phe Ser Pro Thr Tyr Lys Ala Phe Leu Cys Lys Gln Tyr Leu Asn
            660                 665                 670
Leu Tyr Pro Val Ala Arg Gln Arg Pro Gly Leu Cys Gln Val Phe Ala
        675                 680                 685
Asp Ala Thr Pro Thr Gly Trp Gly Leu Val Met Gly His Gln Arg Met
    690                 695                 700
Arg Gly Thr Phe Leu Ala Arg Leu Pro Ile His Thr Ala Glu Leu Leu
705                 710                 715                 720
Ala Ala Cys Phe Ala Arg Ser Arg Ser Gly Ala Asn Ile Leu Gly Thr
                725                 730                 735
Asp Asn Ser Val Val Leu Ser Arg Lys Tyr Thr Ser Tyr Pro Trp Leu
            740                 745                 750
Leu Gly Cys Ala Ala Asn Trp Ile Leu Arg Gly Thr Ser Phe Val Tyr
        755                 760                 765
Val Pro Ser Ala Leu Asn Pro Ala Asp Asp Pro Ser Arg Gly Arg Leu
    770                 775                 780
Gly Leu Ser Arg Pro Leu Leu Arg Leu Pro Phe Arg Pro Thr Thr Gly
785                 790                 795                 800
Arg Thr Ser Leu Tyr Ala Asp Ser Pro Ser Val Pro Ser His Leu Pro
                805                 810                 815
Asp Arg Val His Phe Ala Ser Pro Leu His Val Ala Trp Arg Pro Pro
            820                 825                 830
```

(2) INFORMATION FOR SEQ ID NO: 62:

(i) SEQUENCE CHARACTERISTICS:
        (A) LENGTH: 832 amino acids
        (B) TYPE: amino acid (C) STRANDEDNESS: <Unknown>
        (D) TOPOLOGY: linear (ii) MOLECULE TYPE: protein (xi) SEQUENCE DESCRIPTION: SEQ ID NO: 62:

Met Pro Leu Ser Tyr Gln His Phe Arg Arg Leu Leu Leu Leu Asp Asp
1               5                   10                  15

Glu Ala Gly Pro Leu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50              55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Lys Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
            195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Phe His Pro Thr Ala
225                 230                 235                 240

Arg Arg Pro Phe Gly Val Glu Pro Ser Gly Ser Gly His Thr Thr Asn
                245                 250                 255

Phe Ala Ser Lys Ser Ala Ser Cys Leu His Gln Ser Pro Val Arg Lys
            260                 265                 270

Ala Ala Tyr Pro Ser Val Ser Thr Phe Glu Lys His Ser Ser Ser Gly
        275                 280                 285

His Ala Val Glu Leu His Asn Leu Pro Pro Asn Ser Ala Arg Ser Gln
    290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ser Arg Val Thr Gly Gly Val Phe Leu Val Asp Lys Asn
        355                 360                 365

Pro His Asn Thr Ala Glu Ser Arg Leu Val Val Asp Phe Ser Gln Phe
    370                 375                 380

```
Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
            405                 410                 415

Leu Asp Val Ser Ala Ala Phe Tyr His Leu Pro Leu His Pro Ala Ala
        420                 425                 430

Met Pro His Leu Leu Val Gly Ser Ser Gly Leu Ser Arg Tyr Val Ala
        435                 440                 445

Arg Leu Ser Ser Asn Ser Arg Ile Leu Asn His Gln His Gly Thr Met
    450                 455                 460

Pro Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Tyr Met Asp Asp Val Val Leu
    530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu Asn Phe Met Gly Tyr Val Ile Gly Cys Tyr
            580                 585                 590

Gly Ser Leu Pro Gln Glu His Ile Ile Gln Lys Ile Lys Glu Cys Phe
        595                 600                 605

Arg Lys Leu Pro Val Asn Arg Pro Ile Asp Trp Lys Val Cys Gln Arg
    610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Gly Gln Arg Pro Gly Leu Cys Gln Val Phe Ala
        675                 680                 685

Asp Ala Thr Pro Thr Gly Trp Gly Leu Ala Met Gly His Gln Arg Met
    690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Ile Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
    770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
```

```
                805                 810                 815
Asp Leu Val His Phe Ala Ser Pro Leu His Val Ala Trp Arg Pro Pro
                820                 825                 830

(2) INFORMATION FOR SEQ ID NO: 63:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 63:

Met Pro Leu Ser Tyr Gln His Phe Arg Arg Leu Leu Leu Asp Asp
1               5                   10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Phe Tyr Ser
    50                  55                  60

Ser Thr Val Pro Val Phe Asn Pro His Trp Glu Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Lys Val Thr Lys Tyr Leu Pro Leu Asp Lys Gly
            115                 120                 125

Ile Lys Pro Tyr Tyr Pro Glu His Leu Val Asn His Tyr Phe Gln Thr
            130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Ile His Gln Ser Ser Gly
            180                 185                 190

Ile Leu Ser Arg Pro Pro Val Gly Ser Ser Leu Gln Ser Lys His Arg
            195                 200                 205

Lys Ser Arg Leu Gly Leu Gln Ser Gln Gln Gly His Leu Ala Arg Arg
        210                 215                 220

Gln Gln Gly Trp Ser Trp Ser Ile Arg Ala Gly Thr His Pro Thr Ala
225                 230                 235                 240

Arg Arg Pro Phe Gly Val Glu Pro Ser Gly Ser Gly His Thr Thr His
                245                 250                 255

Arg Ala Ser Lys Ser Ala Ser Cys Leu Tyr Gln Ser Pro Asp Arg Lys
            260                 265                 270

Ala Thr Tyr Pro Ser Val Ser Thr Phe Glu Arg His Ser Ser Ser Gly
            275                 280                 285

Arg Ala Val Glu Leu His Asn Phe Pro Pro Asn Ser Ala Arg Ser Gln
        290                 295                 300

Ser Glu Arg Pro Ile Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
```

-continued

```
                325                 330                 335
Asp Trp Gly Pro Cys Asp Glu Tyr Gly His His Ile Arg Ile Pro
                340                 345                 350

Arg Thr Pro Ala Arg Val Thr Gly Gly Val Phe Leu Val Asp Lys Asn
                355                 360                 365

Pro His Asn Thr Ala Glu Ser Arg Leu Val Val Asp Phe Ser Gln Phe
            370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Gly Phe Tyr His Leu Pro Leu His Pro Ala Ala
                420                 425                 430

Met Pro His Leu Leu Val Gly Ser Gly Val Ser Arg Tyr Val Ala
            435                 440                 445

Arg Leu Ser Ser Asn Ser Arg Asn Asn Asn Gln Tyr Gly Thr Met
        450                 455                 460

Gln Asn Leu His Asp Ser Cys Ser Arg Gln Leu Tyr Val Ser Leu Met
465                 470                 475                 480

Leu Leu Tyr Gln Asn Phe Gly Trp Lys Leu His Leu Tyr Ser His Pro
                485                 490                 495

Ile Val Leu Gly Phe Arg Lys Ile Pro Met Gly Val Gly Leu Ser Pro
                500                 505                 510

Phe Leu Leu Ala Gln Phe Thr Ser Ala Ile Cys Ser Val Val Arg Arg
                515                 520                 525

Ala Phe Pro His Cys Leu Ala Phe Ser Tyr Met Asp Asp Val Val Leu
            530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu His Phe Met Gly Tyr Val Ile Gly Cys Tyr
            580                 585                 590

Gly Ser Leu Pro Gln Glu His Ile Ile Gln Lys Ile Lys Glu Cys Phe
        595                 600                 605

Arg Lys Val Pro Val Asn Arg Pro Ile Asp Trp Lys Val Cys Gln Arg
            610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Phe Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
        675                 680                 685

Asp Ala Thr Pro Thr Gly Trp Gly Leu Gly Met Gly His Gln Arg Met
            690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Leu Gly Thr
                725                 730                 735

Asp Asn Ser Val Val Leu Ser Arg Lys Tyr Thr Ser Phe Pro Trp Leu
            740                 745                 750
```

```
Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
        770                 775                 780

Gly Leu Ser Arg Pro Leu Cys Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
                820                 825                 830

(2) INFORMATION FOR SEQ ID NO: 64:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 64:

Met Pro Leu Ser Tyr Gln His Phe Arg Arg Leu Leu Leu Leu His Asp
1               5                   10                  15

Glu Ala Gly Pro Leu Glu Glu Glu Leu Pro Arg Leu Pro Asp Gln Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Leu Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
            195                 200                 205

Lys Ser Arg Leu Gly Leu Gln Ser Gln Gln Gly His Leu Ala Arg Arg
        210                 215                 220

Gln Gln Gly Arg Ser Trp Ser Ile Arg Ala Gly Phe His Pro Thr Ala
225                 230                 235                 240

Arg Arg Ser Phe Gly Val Glu Pro Ser Gly Ser Gly His Thr Thr Tyr
                245                 250                 255

Arg Ala Ser Lys Ser Ala Ser Cys Leu Tyr Gln Ser Pro Val Arg Lys
            260                 265                 270
```

```
Ala Ala Tyr Pro Ser Val Ser Thr Phe Glu Lys His Ser Ser Gly
        275                 280                 285
His Ala Val Glu Leu His Asn Leu Pro Pro Asn Ser Ala Arg Ser Gln
290                 295                 300
Ser Glu Arg Pro Val Phe Pro Cys Trp Trp Leu Gln Phe Arg Asn Ser
305                 310                 315                 320
Lys Pro Cys Ser Asp Tyr Cys Leu Ser Leu Ile Val Asn Leu Arg Glu
                325                 330                 335
Asp Trp Gly Pro Cys Thr Glu His Gly Glu His His Ile Arg Ile Pro
            340                 345                 350
Arg Thr Pro Ala Arg Val Thr Gly Gly Val Phe Leu Val Asp Lys Asn
        355                 360                 365
Pro His Asn Thr Ala Glu Ser Arg Leu Val Val Asp Phe Ser Gln Phe
    370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Val Ser Ala Ala Phe Tyr His Leu Pro Leu His Pro Ala Ala
            420                 425                 430
Met Pro His Leu Leu Val Gly Ser Ser Gly Leu Ser Arg Tyr Val Ala
        435                 440                 445
Arg Leu Ser Ser Asn Ser Arg Ile Phe Asn Asn Gln His Gly Thr Met
    450                 455                 460
Gln Asn Leu His Asp Ser Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                485                 490                 495
Ile Ile Leu Gly Phe Arg Lys Ile Pro Met Gly Val Gly Leu Ser Pro
            500                 505                 510
Phe Leu Leu Ala Gln Phe Thr Ser Ala Ile Cys Ser Val Val Arg Arg
        515                 520                 525
Ala Phe Pro His Cys Leu Ala Phe Ser Tyr Met Asp Asp Val Val Leu
    530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                565                 570                 575
Arg Trp Gly Tyr Ser Leu Asn Phe Met Gly Tyr Ile Ile Gly Ser Trp
            580                 585                 590
Gly Thr Leu Pro Gln Asp His Ile Val Gln Lys Ile Lys Glu Cys Phe
        595                 600                 605
Arg Lys Leu Pro Val Asn Arg Pro Ile Asp Trp Lys Val Trp Gln Arg
    610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ala Lys Gln Ala Phe
                645                 650                 655
Thr Phe Ser Pro Thr Tyr Lys Ala Phe Leu Ser Lys Gln Tyr Met Asn
            660                 665                 670
Leu Tyr Pro Val Ala Arg Gln Arg Pro Gly Leu Cys Gln Val Phe Ala
        675                 680                 685
```

```
Asp Ala Thr Pro Thr Gly Trp Gly Leu Ala Ile Gly Asn Gln Arg Met
            690             695             700

Arg Gly Thr Ile Val Ala Pro Leu Pro Ile His Thr Ala Glu Leu Leu
705             710             715             720

Ala Ala Cys Phe Ala Arg Ser Arg Ser Gly Ala Lys Leu Ile Gly Thr
                725             730             735

Asp Asn Ser Val Val Leu Ser Arg Lys Tyr Thr Ser Phe Pro Trp Leu
                740             745             750

Leu Gly Cys Thr Ala Asn Trp Ile Leu Arg Gly Thr Ser Phe Val Tyr
            755             760             765

Val Pro Ser Ala Leu Asn Pro Ala Asp Asp Pro Ser Arg Gly Arg Leu
            770             775             780

Gly Leu Ser Arg Pro Leu Leu Arg Leu Pro Phe Gln Pro Thr Thr Gly
785             790             795             800

Arg Thr Ser Leu Tyr Ala Val Ser Pro Ser Val Pro Ser His Leu Pro
                805             810             815

Val Arg Val His Phe Ala Ser Pro Leu His Ile Ala Trp Arg Pro Pro
                820             825             830

(2) INFORMATION FOR SEQ ID NO: 65:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 65:

Leu Ser Arg Tyr Val Ala Arg Leu
1               5

(2) INFORMATION FOR SEQ ID NO: 66:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 66:

Gly Leu Ser Arg Tyr Val Ala Arg
1               5
```